United States Patent
Labib et al.

(10) Patent No.: US 10,512,523 B2
(45) Date of Patent: Dec. 24, 2019

(54) APPARATUS AND METHODS FOR HYGIENE TESTING A MEDICAL DEVICE

(71) Applicant: Novaflux, Inc., Princeton, NJ (US)

(72) Inventors: Mohamed E. Labib, Yardley, PA (US); Stanislav S. Dukhin, Goldens Bridge, NY (US); Jeffrey C. Robertson, Rochester, NY (US); Peter Materna, Metuchen, NJ (US); Ching-Yue Lai, Pennington, NJ (US); Yacoob Tabani, Basking Ridge, NJ (US)

(73) Assignee: Novaflux, Inc., Yardley, PA (US)

( * ) Notice: Subject to any disclaimer, the term of this patent is extended or adjusted under 35 U.S.C. 154(b) by 0 days.

(21) Appl. No.: 15/685,410

(22) Filed: Aug. 24, 2017

(65) Prior Publication Data
US 2018/0125606 A1    May 10, 2018

Related U.S. Application Data

(60) Provisional application No. 62/378,922, filed on Aug. 24, 2016.

(51) Int. Cl.
*A61L 2/28*     (2006.01)
*A61L 2/00*     (2006.01)
(Continued)

(52) U.S. Cl.
CPC .......... *A61B 90/70* (2016.02); *A61B 1/00057* (2013.01); *A61B 1/125* (2013.01);
(Continued)

(58) Field of Classification Search
CPC combination set(s) only.
See application file for complete search history.

(56) References Cited

U.S. PATENT DOCUMENTS

| 4,397,945 A | 8/1983 | Lemonnier |
| 5,020,543 A | 6/1991 | Rothenberg et al. |
(Continued)

FOREIGN PATENT DOCUMENTS

| DE | 102011050765 A1 | 12/2012 |
| JP | 2009022643 A | 2/2009 |
(Continued)

OTHER PUBLICATIONS

International Search Report and Written Opinion dated Nov. 28, 2017 for PCT Application No. PCT/US2017/048401.

*Primary Examiner* — Brandi N Hopkins
(74) *Attorney, Agent, or Firm* — Moser Taboada

(57) ABSTRACT

Provided among other things is a sampling system for determining an amount or type of contamination a narrow, elongated passageway in a medical device, said sampling system comprising: (a) a fluid supply system that supplies to said passageway a sampling liquid for flowing through said passageway and a gas for flowing through said passageway; and (b) a receiving container that receives liquid from said passageway, wherein said sampling liquid is sterile, wherein said sampling liquid is configured to allow recovery of viable pathogens from the passageway, and wherein said sampling liquid comprises an amount and selection of surfactant effective to enhance the dislodgement of *Enterococcus faecalis* and *Pseudomonas aeruginosa* bacteria from the narrow passageways.

12 Claims, 22 Drawing Sheets

(51) Int. Cl.
*G01N 1/38* (2006.01)
*G01N 1/22* (2006.01)
*G01N 1/10* (2006.01)
*A61B 90/70* (2016.01)
*A61B 1/00* (2006.01)
*A61B 1/12* (2006.01)
*G01N 1/20* (2006.01)
*G01N 33/48* (2006.01)

(52) U.S. Cl.
CPC ............... *G01N 1/20* (2013.01); *G01N 33/48* (2013.01); *A61B 2090/701* (2016.02); *A61B 2090/702* (2016.02)

(56) References Cited

U.S. PATENT DOCUMENTS

| | | | |
|---|---|---|---|
| 5,091,316 A | 2/1992 | Monthony et al. | |
| 5,405,755 A | 4/1995 | Markus et al. | |
| 5,407,807 A | 4/1995 | Markus | |
| 5,462,063 A | 10/1995 | Kist et al. | |
| 5,923,432 A | 7/1999 | Kral | |
| 6,027,572 A | 2/2000 | Labib et al. | |
| 6,197,574 B1 | 3/2001 | Miyamoto et al. | |
| 6,286,527 B1 * | 9/2001 | Stanley | A01N 37/16 134/169 C |
| 6,326,340 B1 | 12/2001 | Labib et al. | |
| 6,394,111 B1 | 5/2002 | Jacobs et al. | |
| 6,428,746 B1 | 8/2002 | Muscarella et al. | |
| 6,454,871 B1 | 9/2002 | Labib et al. | |
| 6,454,874 B1 | 9/2002 | Jacobs et al. | |
| 6,465,206 B1 | 10/2002 | Collins | |
| 6,516,818 B2 | 2/2003 | Jacobs et al. | |
| 6,619,302 B2 | 9/2003 | Labib et al. | |
| 6,699,331 B1 | 3/2004 | Kritzler | |
| 6,793,880 B2 | 9/2004 | Kippenhan | |
| 6,857,436 B2 | 2/2005 | Labib et al. | |
| 6,945,257 B2 | 9/2005 | Tabani et al. | |
| 7,183,048 B2 | 2/2007 | Felkner et al. | |
| 7,322,370 B2 | 1/2008 | Aulbers et al. | |
| 7,367,346 B2 | 5/2008 | Tabani et al. | |
| 7,393,694 B1 | 7/2008 | Schlein et al. | |
| 7,485,262 B2 | 2/2009 | DiCesare et al. | |
| 7,524,673 B2 | 4/2009 | Gonzalez et al. | |
| 7,862,660 B2 | 1/2011 | Murawski et al. | |
| 7,879,289 B2 | 2/2011 | Williams | |
| 8,083,861 B2 | 12/2011 | Labib et al. | |
| 8,084,247 B2 | 12/2011 | Cregger et al. | |
| 8,110,112 B2 | 2/2012 | Alburty et al. | |
| 8,114,221 B2 * | 2/2012 | Labib | B08B 9/032 134/22.1 |
| 8,226,774 B2 | 7/2012 | Labib et al. | |
| 8,292,825 B2 | 10/2012 | Brewer et al. | |
| 8,476,064 B2 | 7/2013 | Salter et al. | |
| 8,490,235 B2 | 7/2013 | Soetermans et al. | |
| 8,584,535 B2 | 11/2013 | Page et al. | |
| 8,747,569 B2 | 6/2014 | Labib et al. | |
| 9,354,182 B2 | 5/2016 | Rochette et al. | |
| 9,388,451 B2 | 7/2016 | Ramachandran et al. | |
| 9,492,853 B2 | 11/2016 | Labib et al. | |
| 9,541,557 B2 | 1/2017 | Perrett et al. | |
| 2006/0102200 A1 | 5/2006 | Esquenet et al. | |
| 2006/0269445 A1 | 11/2006 | Basile et al. | |
| 2009/0229632 A1 | 9/2009 | Labib et al. | |
| 2012/0234357 A1 | 9/2012 | Labib et al. | |
| 2012/0285488 A1 * | 11/2012 | Labib | B08B 9/0325 134/22.12 |
| 2012/0315627 A1 | 12/2012 | Aojula et al. | |
| 2016/0010139 A1 | 1/2016 | Mackay et al. | |

FOREIGN PATENT DOCUMENTS

| | | |
|---|---|---|
| KR | 20010099452 A | 11/2001 |
| KR | 20100011884 A | 2/2010 |
| WO | WO-2014138043 A1 | 9/2014 |
| WO | WO-2017091385 A1 | 6/2017 |

* cited by examiner

APPARATUS AND METHODS FOR HYGIENE TESTING A MEDICAL DEVICE

This application claims the priority of U.S. Ser. No. 62/378,922, filed Aug. 24, 2016, the content of which is incorporated herein in its entirety.

Embodiments of the invention pertain to extraction, recovery and sampling apparatus and methods for luminal medical devices such as endoscopes and other confined passageways, to quantify organic soils, bioburden, biofilms and residues in such devices.

In medical practice, endoscopes and similar medical devices are typically inserted through incisions or natural body orifices, and can provide visual imaging of internal organs and tissues in a subject patient, or can also be used to perform surgery and other procedures. A flexible endoscope, comprising a long, flexible hollow member, has a distal tip, through which an optical system can illuminate an area around the distal tip, and through which the optical system can receive an image of the patient organ or tissues proximal the tip. Many endoscopes also have internal channels or tubes connected to ports in the distal tip, through which the clinician can inject fluids into the area near the distal tip, and remove by suction any fluids or other materials near the distal tip. In some endoscopes the suction channel can be large enough to allow the insertion of tools for excising and extracting biopsy samples or for performing other procedures including surgery.

The possible contamination or inadequate cleaning of endoscopes is a significant problem that has resulted in illnesses and even fatalities in patients over the years with many cases documented by the Centers for Disease Control and other health authorities. The construction and materials of modern endoscopes generally preclude the use of high temperature steam for sterilization, and the long length and the small cross-sectional size of the various internal tubing channels causes fundamental difficulties in cleaning, disinfecting, and sterilizing these channels. Current cleaning processes include manual cleaning, cleaning with liquid disinfectants, cleaning with two-phase flow, and other methods and combinations of these methods. Most of the current cleaning techniques and methods have limitations, and there are no reliable and reproducible methods to detect or assess the cleanliness or the residual contamination levels of endoscopes used on patients at the present time. Furthermore, several new investigations revealed that even after endoscopes are high-level disinfected, more than 75% of such endoscopes still contain live organisms that can infect patients. Concrete evidence now shows that biofilms are implicated and that this biofilm arises from residual organisms remaining in the endoscopes even after high-level disinfection.

Thus, there still remains need for improvement to minimize the risk of patient infection. Specifically, with whatever cleaning method(s) are used, there is a need for tests or systems or methods that will reproducibly assess or verify whether an already-reprocessed medical device such as an endoscope is adequately clean and safe for its next use on patients. Accordingly, there is an urgent need for reliable easy to use extraction, recovery and sampling apparatus and methods that can facilitate wider testing and surveillance of luminal medical devices and passageways employed in healthcare, pharmaceutical and other critical industries.

SUMMARY

Provided is a sampling system for determining an amount or type of contamination a narrow, elongated passageway in a medical device, said sampling system comprising: (a) a fluid supply system that supplies to said passageway a sampling liquid for flowing through said passageway and a gas for flowing through said passageway; and (b) a receiving container that receives liquid from said passageway, wherein said sampling liquid is sterile, wherein said sampling liquid is configured to allow recovery of viable pathogens from the passageway, and wherein said sampling liquid comprises an amount and selection of surfactant effective to enhance the dislodgement of *Enterococcus faecalis* and *Pseudomonas aeruginosa* bacteria from the narrow passageways.

Further provided is a method for determining an extent or nature of contamination of an endoscope having two or more narrow elongated channels, said method comprising: (A) supplying a sampling liquid for flowing through the channels of said endoscope, wherein said sampling liquid comprises a sterile aqueous composition that is essentially free of surfactant; (B) supplying clean compressed air for flowing through said channels or said interiors of said endoscope, wherein said sampling liquid flows through said channels as part of a two-phase flow; (C) collecting fluid exiting said channels in one or more receiving containers; and (D) analyzing contaminant contents of said receiving containers.

Also provided is a system for determining an extent or nature of contamination of a medical device, said sampling system comprising: (1) a flow supply system configured to supply two-phase flow; (2) a connector for interfacing with a surface of said device; (3) a nozzle for directing a flow of said two-phase flow at said surface; and (4) a receiving container for receiving flow that has been directed at said surface.

Additionally provided is a system for determining an extent or nature of contamination of an endoscope, said system comprising: (I) a flow supply system for supplying flow of a sampling fluid to said endoscope; (II) a receiving container, in fluid communication with a distal end of said endoscope, for receiving said flow of said sampling fluid from said endoscope; (III) a brush or swab for brushing an interior of a channel that can accept said brush or said swab, said brush or said swab being connected to a drive mechanism; and (IV) a mechanism for disconnecting or cutting or detaching said brush or said swab or a portion thereof from said drive mechanism while said receiving container is in fluid communication with said distal end of said endoscope, wherein said disconnected brush or the disconnected swab or portion thereof can be deposited into said receiving container while said receiving container is in fluid communication with said endoscope.

Further provided are methods using the systems described.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1:
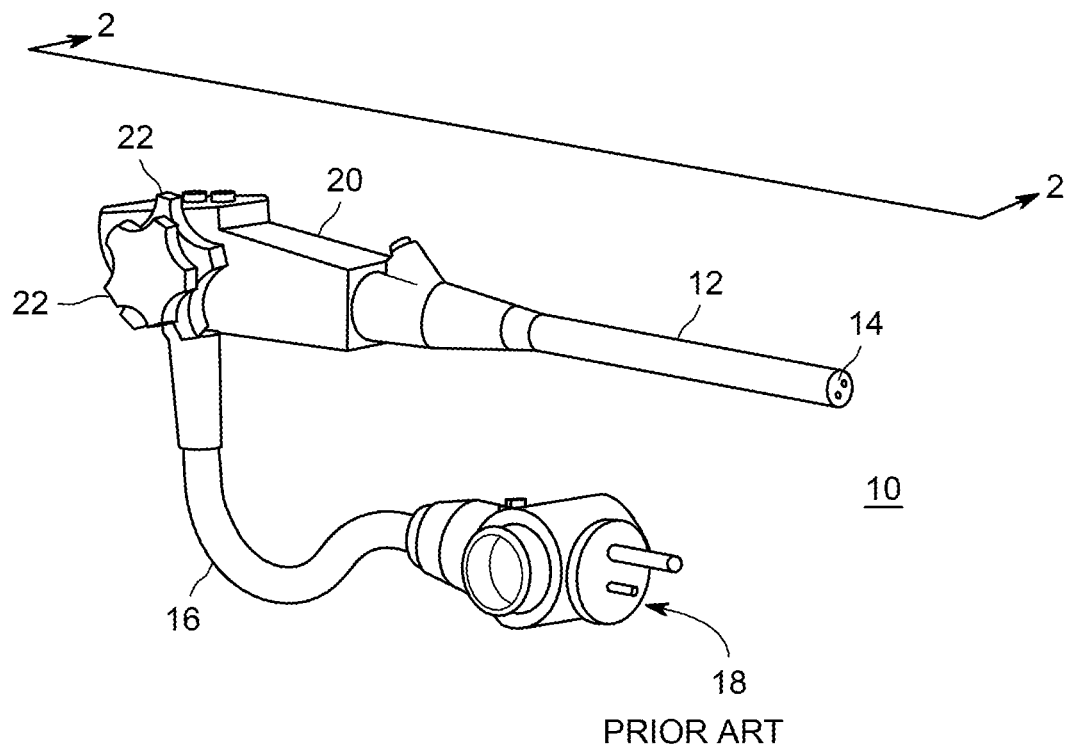
FIG. 1 is an external view of a typical endoscope, from an oblique perspective.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

As an initial matter, it is useful to describe the nature of contaminants that can exist on or inside medical devices. First, live bacteria can contaiminate. The bacteria can be isolated single cells, unattached to a solid surface and able to move around in water, and such bacteria are called planktonic bacteria. Also, there can be live bacteria that can be embedded in biofilm. Biofilm can form on solid surfaces such as the interior surface of a channel or on the external surface of an endoscope including on the elevator section of ERCP (Endoscopic Retrograde Cholangiopancreatography) endoscopes. Biofilm is believed to comprise a matrix of polysaccharides, and it can form strong structures with high cohesion forces and can have strong adhesion to solid surfaces. Bacteria can be embedded in and can grow in biofilm, where they are more resistant to dislodgment and the effects of biocides. Collectively, the planktonic and biofilm forms of bacterial contamination are referred to as bioburden. Bioburden can include both dead bacteria and live bacteria. It can be noted that even dead bacteria can be harmful, and it can be appropriate to remove even the dead bacteria from internal passageways. Yet another category of contaminants is organic soil. Organic soil can include any one or more of a variety of substances such as proteins, carbohydrates, hemoglobin, albumin, serum, human cells and generally blood or any components of blood, whether unclotted or clotted. Yet another category of contaminants is viruses. Yet another category is prions such as are associated with bovine spongiform encephalitis (mad cow disease). It is desirable to recover, quantitate and reliably assess residual bioburden including biofilm and organic soil remaining in endoscopes or similar medical devices.

Contaminants of interest in endoscopes and other luminal devices can be classified into several classes depending on their adhesion to the surface, their cohesion forces that hold the bulk of the contaminant together, and the ease of removing them from a surface, as follows;

Class 1: Organic soils and organic residues: Such contaminants can be recovered with simple liquid including sterile reverse osmosis water (SRO), saline solution, buffers and surfactant solutions (e.g., Tween 20 to Tween 80 or similar surfactants). In this case, the recovered sample can be analyzed for residual protein, carbohydrates and hemoglobin using standard analytical methods. Alternatively, total organic carbon (TOC) of the recovered sample can be measured by established TOC techniques as described in the AAMI Technical Information Report TIR 30:2011 "A compendium of processes, materials, test methods, and acceptance criteria for cleaning reusable medical devices" (Association for the Advancement of Medical Instrumentation, 2011; ISBN 1-57020-419-5).

Class 2: Planktonic bacteria and loose organisms (other than biofilms) that possess low adhesion to the surface: These contaminants can be removed by the same liquids as described in Class 1. Recovered organisms can be quantitated by culture methods or by molecular methods including DNA- or RNA-based methods or the like. In some cases, ATP-based methods can be employed to detect viable organisms above some concentration as is known in the field.

Class 3: Biofilms both traditional and built up forms: Biofilms represents are the most difficult contaminant to remove form a surface. Biofilms can be divided into at least three types that show varying difficulty in removal from a surface:

Type 1: Young and fragile biofilms: This is the most easy-to-remove biofilm where the extracellular polysaccharide matrix is immature and still weak and its molecules are not well entangled. The organisms of this biofilm type are not very well established within the matrix and can be easily dispersed into single cells by small to moderate mechanical action. This mechanical action can be characterized by a small to moderate hydrodynamic detachment forces which can be generated by turbulent liquid flow or by application of a gas-liquid mixture which is otherwise known as two-phase flow. It is estimated that the application of shear stress of about 1 to 5 Pa (perhaps in some cases up to 10 Pa) may be the necessary to remove this type of biofilm.

Type II: Built up crosslinked biofilms: This is the most difficult type of biofilm to remove from a surface. It can be formed over time where it accumulates and becomes entangled and crosslinked, including by disinfectant such as glutaraldehyde. In this older mature biofilm, the extracellular polysaccharide matrix becomes fibrillated and entangled, and the organisms become strongly entrenched into the matrix. Built up biofilms have high adhesion to surfaces as well as high cohesion and strength where the bulk of biofilm behaves as a viscoelastic body with finite yield stress which can be as high as 50 Pa. In order to remove the built up biofilms, high shear stress can help but abrasion and erosion of the biofilm matrix are usually required. Accordingly, much of this biofilm type may not be removed by turbulent liquid flow even in the presence of surfactants. Other means of removing this mature biofilm can include erosion in addition to mechanical shear stress as described elsewhere herein.

Type III: Intermediate strength traditional biofilms: These biofilms have intermediate properties between Type I and Type II as described above. They may be removed by turbulent liquid flow sometimes but not always, because the biofilm can vary in adhesion and strength. Type III biofilms may require the application high forces and erosion processes to reliably remove them from the surface.

Methods to sample an endoscope, medical devices or otherwise a critical surface require recovering residues from the surfaces, extracting the residues from the recovered sample, and then analyzing the recovered sample to determine the amount and nature of residues removed from the surface.

Sampling an external surface of a device is normally done by the application of a special swab to a known surface area, which is normally done according to an accepted protocol. The amount of residue removed per unit area (e.g., $cm^2$) is determined by subsequently extracting the residue from the swab with a liquid and then analyzing the residue using appropriate analytical techniques. For organic residues or organic soil, the results are normally expressed in units of microgram/$cm^2$. The total amount of organic residues can also be determined by the total organic carbon of the extracted sample as it is normally practiced in validated cleaning in the pharmaceutical industry. That industry has arbitrarily adopted some benchmark values to indicate that a surface is adequately cleaned. Current benchmarks set for devices such as endoscopes are: protein <6.4 µg/$cm^2$; carbohydrates <1.8 µg/$cm^2$ and hemoglobin <2.2 µg/$cm^2$.

If it is necessary to measure the amount of bioburden (organisms), the organisms on the swab or recovered liquid sample are typically subjected to a mechanical force such as vortexing or sonication in an appropriate liquid. The extracted sample is normally analyzed by culture methods or by molecular techniques including DNA, RNA, ATP and other specialized methods as is known in the art. Culture results are typically expressed in cfu/$cm^2$ or other informative units. Recovery of organisms can be more reliable if the organisms are in the planktonic form and when they have low adhesion to the surface. Recovery can be more difficult if the biological contaminants are in the form of biofilm as discussed elsewhere herein.

Sampling a channel or lumen surface such as in the case of endoscopes presents a challenge because it is difficult to access entire surface area of such geometry, especially when such lumen is part of a complex medical device. There are limitations to employ a brush or a swab in channels due to dimensional and geometric limitations. For example, the suction/biopsy channel of an endoscope can be brushed to some extent and in this case it is possible to have direct contact with the majority (but not all) of the channel surface. On the other hand, the narrow air/water and other auxiliary channels such as water jet, irrigation, CO2, and elevator wire channels of endoscopes cannot be brushed due to their small inside diameters (about 0.5 to 1.4 mm ID). For the latter, proper recovery and sampling of the channels is very challenging and difficult.

Accordingly, residues and contaminants in the wider suction/biopsy channels can be recovered by a method that includes Flush/Brush/Flush steps. The collected liquid sample and the brush tip can be used to quantitate the organic residues and organism as it is known in the art. On the other hand, currently the narrow channels can only be sampled by liquid flushing methods which are normally referred to as Flush/Flush. The collected liquid sample is then analyzed by accepted methods to quantify organic residues and organisms as discussed elsewhere herein.

Although the above methods are used in the industry, they are tedious, cumbersome, time consuming, labor intensive and impractical to use or apply on a large scale. For example, it may take a full day of trained microbiologist time to recover and sample two endoscopes per day, which is cumbersome and impractical. Additional current methods are helpful in some cases, but they cannot provide reliable data sufficient to protect patients from infection during repeated use of medical devices such as endoscopes. There is an urgent need for more reliable and automated methods so that sampling of medical devices can become the standard of care to protect patients from dangerous and sometimes fatal infections.

Figure 2A:
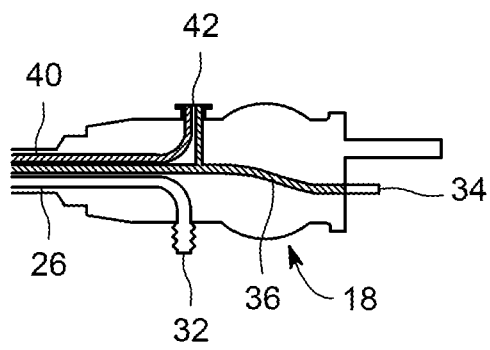
FIGS. 2A to 2C are lateral cross-sectional views of portions of the endoscope of FIG. 1, particularly the umbilical end (2A), handle portion (2B), and distal portion (2C), respectively.
Figure 2B:
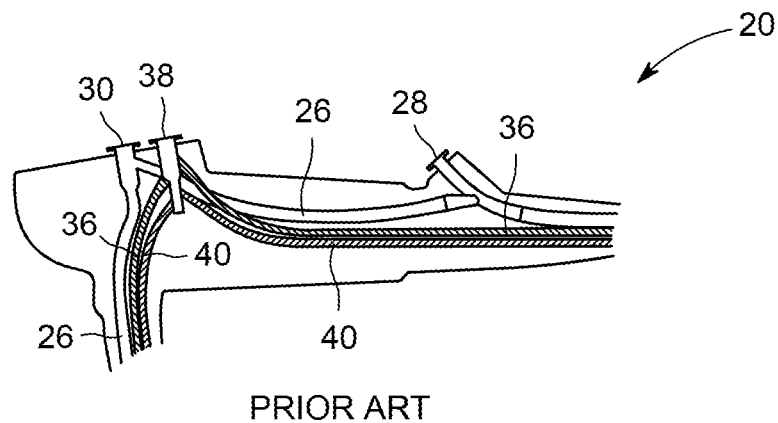
Figure 2C:
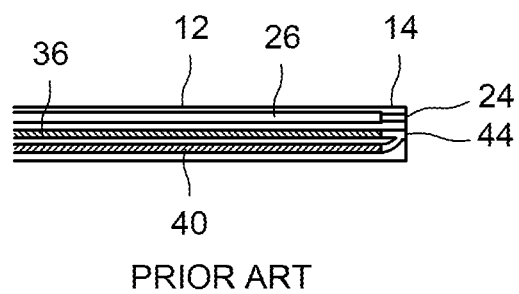

It can also be useful at this point to describe the design and construction of a typical endoscope such as a flexible endoscope. Referring now to FIGS. 1-2A to 2C, there is illustrated a typical endoscope 10, which can be utilized for procedures such as bronchoscopy, colonoscopy, enteroscopy, laryngoscopy, or upper gastrointestinal endoscopy. FIG. 1 is an external view, in which for illustrative purposes, the endoscope is shown foreshortened as a result of the viewing direction. FIGS. 2A to 2C show a cross-section of the endoscope of FIG. 1.

With reference to FIGS. 1 and 2A to 2C, endoscope 10 can have an elongated flexible distal portion 12 (insertion tube), which can terminate in distal tip 14 at a first end, and which can be connected to handle 20 at a second end. There can also be an umbilical portion 16, which can connect to handle 20, and can terminate at umbilical end 18. Controls 22 on handle 20 can operate control wires within distal portion 12, allowing the clinician to steer distal tip 14 in two mutually orthogonal directions.

With continued reference to FIGS. 1 and 2A to 2C, there can be various channels extending through all or part of the length of the endoscope for particular purposes. One channel that can be particularly complicated in terms of access points is a channel called the suction/biopsy channel 26, also referred to as a working channel. Such a channel can have as many as four access points. At the distal end of the endoscope, this channel can of course have a port 24 for interacting with the body part or bodily cavity being examined. Moving proximally, there is often provided a port 28, which can join the suction/biopsy channel at an oblique angle, through which a biopsy sampling device can be inserted and a biopsy sample can be removed. Continuing on, there can be a spool valve 30 that controls or turns on and off a flowpath through that channel, such as a flowpath for suction. Finally, at the umbilical end of the endoscope, the suction/biopsy channel can have a connection port at the most proximal end of the suction/biopsy channel. The connection point at the proximal end of the umbilical can be a fluid connection point such as for suction.

FIGS. 2A to 2C illustrate the various portions of suction tube 26. A first portion can connect suction port 24 in distal tip 14 to biopsy port fitting 28 on handle 20. A second portion can connect biopsy port fitting 28 to suction cylinder 30, which is also located on handle 20. A third portion can connect suction cylinder 30 and thence can continue on to suction fitting 32 on umbilical end 18. The suction tube 26 can commonly be an extruded tube manufactured from a thermoplastic resin such as a polyethylene or polypropylene or a fluoropolymer such as polytetrafluoroethylene (Teflon®), with a nominal inside diameter of for example approximately 3 millimeters. Most endoscope manufacturers use fluoropolymers as the preferred material for the tubing for internal channels. During endoscopic procedures, a vacuum source and collection vessel can be connected to suction fitting 32, a cap can be installed on biopsy port fitting 28, and a spool valve can be inserted in suction cylinder 30. By operating the spool valve inserted into suction cylinder 30, the clinician is able to suction materials proximal to distal tip 14 through suction port 24, into the collection vessel connected to suction fitting 32. If necessary, the cap on biopsy port fitting 28 can be removed, and surgical tools can be inserted there-through, going through the first section of suction tube 26, and extending through suction port 24 in distal tip 14, to allow the clinician to excise and retrieve tissue samples for the purpose of biopsy.

Also in FIGS. 2A to 2C, there is illustrated an air channel that can receive air at a slight positive pressure through air fitting 34 on umbilical end 18, and can conduct this air through an air tube 36, to air/water cylinder 38 in handle 20. A branch in air tube 36 can connect to air/water fitting 42 on umbilical end 18 and can supply pressurized air to a water bottle (not shown) connected to air/water fitting 42, which in turn can supply water through air/water fitting 42 to a first section of water tube 40, connected between air/water fitting 42 on umbilical end 18, and air/water cylinder 38 in handle 20. Second sections of air tube 36 and water tube 42 extend from air/water cylinder 38, through distal portion 12 of endoscope 10, toward distal tip 14. As illustrated, the second sections of air tube 36 and water tube 40 can merge with each other at or near distal tip 14, such that a single combined air/water channel can be formed emerging as air/water port 44 in distal tip 14.

Typically air tubes 36 and water tubes 40 are manufactured by extruding a thermoplastic resin such as a polyethylene or polypropylene or a fluoropolymer, in the form of a hollow tube or channel having a nominal inside diameter of for example approximately 1.2 millimeters. (To the extent that reference is made below to the suction tube 26, air tube 36, or water tube 40, reference can be made to FIGS. 2A-2C.)

A spool valve (not shown), which can be inserted into air/water cylinder 38 in handle 20, can allow the clinician to selectively inject air or water through air/water port 44 into the space near the distal tip 14 for the purpose of rinsing or flushing patient tissues to remove any material or debris that can preclude the capture of definitive diagnostic images. Such valving controls can serve to open or close the flow passage. Such valves can be spool valves, having a geometry of a cylindrical bore in which a slidable spool can be located. In such a geometry, the spool can be slidable along the axial direction of the cylinder. Such sliding of the spool can open or close certain openings in the cylindrical wall thereby opening or closing certain flow paths. The sliding nature of the spool valve can provide the surgeon the opportunity to open or close a flowpath or various flowpaths by the appropriate pushing of a button. In some endoscopes both an air channel and a water channel can be valved by different portions of the same spool valve.

Some endoscopes can have a mechanism mounted externally on distal tip 14 for the purpose of deflecting or steering a biopsy probe or other surgical tool, when the surgical tool is extended through a suction port or biopsy port in the endoscope tip. Such a hinged elevator component can control the angle or tilt of a component such as a biopsy device that can pass through one of the other channels of the endoscope. This mechanism is typically actuated by means of a control wire that passes through a control channel extending from handle 20 through distal tip 14. This can be referred to as an elevator channel. The elevator channel, if present, can contain a cable to operate a hinged elevator component at the distal tip of the endoscope. Experience has shown that the region near an elevator channel at the tip of an endoscope is especially difficult to clean.

An endoscope can further comprise various optical components (not illustrated). Such components can take the form of a coherent optical fiber bundle, running from umbilical end to the distal tip, for the purpose of illuminating the space near the distal tip, with the coherent optical fiber bundle transmitting an image of the area back to the umbilical end. Alternatively, the optical components can comprise a light source such as an LED and a miniaturized digital camera mounted at or near the distal end of the endoscope.

It can also be useful to initially describe typical reprocessing procedures for endoscopes. For a typical endoscope used in a medical procedure, a typical reprocessing can comprise a multistep process, performed by a certified technician. Such a procedure can be specific to a particular model of endoscope. Commonly, a series of rinse agents, cleaners, disinfectants and sterilants are sent through all of the internal channels of the endoscope, in an attempt to remove any biofilm that may have formed on the interior surfaces of the channels, and in an attempt to kill any micro-organisms that may be present in the channels. Sometimes a brush or swab, disposed at the end of a long flexible shaft, can be inserted through a channel that is wide enough to accept such a brush or swab. For example, such a brush or swab can be inserted into biopsy port fitting 28, and can be extended through the first section of suction tube 26, until it exits suction port 24 of distal tip 14, to assist with cleaning that portion of the suction channel. Typically the suction/biopsy channel has a larger inside diameter than other channels, so it may be the channel that is most likely to able to be cleaned or sampled using a brush or swab. Also, the suction/biopsy channel can have a greater extent or likelihood of containing contamination that needs to be removed. It is also possible that some other channels can be cleaned with a brush or swab if their inside diameter is appropriate, such as greater than about 1.8 mm or 2 mm.

In an endoscope that has a spool valve for control of flow, the spool valve itself can have small corners and seals and similar features that can be possible locations for contaminants to reside in. Accordingly, it is common for components such as the spool of a spool valve to be removable so that they can be cleaned while they are apart from the body of the valve, and also so that the nearby parts of the flowpath and valve body can be cleaned without the spool being present.

Also during typical reprocessing, the exterior surfaces of the endoscope can be cleaned with similar chemicals. Also, the internal channels and exterior surfaces can be thoroughly rinsed, and all remaining liquids can be purged from the internal channels. Finally, the re-processed endoscope can be dried, and placed in storage until its next usage.

In most current practice for most endoscopes, if any processes are performed for the sampling/testing of the cleaned endoscope to assess its cleanliness, those processes are usually manual processes. Such a procedure is time-consuming and typically is performed by a trained microbiologist, which makes the procedure costly. Also, the process lacks consistency and repeatability because it depends on the operator to perform the cleaning or the sampling/testing substantially the same way every time. Currently, because of the narrowness and length of certain channels, if the process includes a step of causing liquid to flow through the channel, typically that liquid is injected by syringe, and typically injecting the liquid requires a large amount of force from the technician or operator to inject liquid and cause the liquid to flow through the channel for sampling. Depending upon the preference of the doctor or technician, a sampling/testing/assessment can be performed immediately after cleaning, or it can be performed at a separate time such as after high-level disinfection or after storage or immediately before the endoscopic procedures. Some healthcare facilities recommend periodic sampling and surveillance of endoscopes used in their facilities perhaps one time per month. For endoscopes used in some invasive procedures such as ERCP, it is now recommended that endoscopes be sampled and certified before performing each such procedure. These new requirements became mandatory after the death of patients after ERCP procedures at the UCLA hospital and in other parts of the world. The culprit in these deaths has been referred to as a "superbug," which is resistant to antibiotics. The industry now needs new devices, methods and systems to reliably and efficiently sample endoscopes before they are used on patients so as to avoid infection, transmission of disease and death of patients who undergo endoscopic procedures.

Description Common to Various Embodiments

Referring now to embodiments of the invention, there can be provided systems, apparatus and methods to assess the cleanliness of an endoscope, such as to verify or certify that an endoscope is safe for upcoming use on a patient in a medical procedure, such as to assess the efficacy of an endoscope re-processing procedure. Various embodiments of the invention are presented herein. Embodiments can include systems, apparatus or methods or their combination. The invention, and embodiments thereof, can be used with any medical device having elongated, narrow passageways, which are passageways that are not cleanable with an ordinary sponge.

In embodiments of the invention, no matter what method may have been used to clean or to disinfect the endoscope during reprocessing, there can be provided a system or apparatus for performing the sampling or assessment using any of several types of procedures. Although variations among details are possible for embodiments of the invention, some of the components that are common to various of the embodiments are: kits, cartridges, components and accessories, which can be one-time-use components, which are provided in a sterile condition with appropriate packaging to maintain sterility; and components that are part of a durable machine that may be re-used. In embodiments, the durable machine can have automation that is capable of causing steps of the procedure to be performed repeatedly in a substantially identical manner. Avoiding cross-contamination (i.e., transfer of contamination from one endoscope to another) during recovery and sampling is important and can be maintained according to embodiments of the present invention.

Some of the embodiments provide a flow through the endoscope channels, for purposes of recovering and sampling, wherein the flow is a two-phase flow of liquid and gas. At times this flow can remove contaminants that can be present, such as contaminants that may have survived the previous reprocessing procedure, or may have grown and expanded in the form of biofilm after reprocessing, including after high-level disinfection. Such contaminants can be collected in the recovered sample, and follow-up analysis of recovered liquid would reveal the endoscope as being non-sterile, as well as revealing the nature and the level or concentration of the contamination. Contaminants detectable according to the invention include organic soil, bacteria, viruses, yeast and fungi and prions, and possibly other materials including immunogens and endotoxins.

Some other embodiments provide flow of only a liquid through the endoscope channels, for purposes of recovery and sampling of residual contamination. In embodiments, flow of only a liquid could not dislodge or recover contaminants from channels as vigorously as would occur with two-phase flow of a liquid and a gas, but still such liquid-only flow may be sufficient for assessment of endoscope with respect to assessing the level of the above contaminants. Such liquid is referred to herein as a sampling liquid, although it can accomplish either or both of sampling and recovering of contaminants, microorganisms, etc. The liquid component of a two-phase flow is also referred to herein as a sampling liquid.

In order to achieve better recovery of contaminants and residues from long and narrow passageways, another technique based on using a mixture of a liquid and a gas has shown to provide much better recovery results. This technique is referred to as two-phase flow. In "two phase flow," a mixture of liquid and gas is formed in situ inside the channel by supplying a liquid and gas at predetermined flow rate and pressures at the entrance of the channel. The gas to liquid ratio can be selected to make various forms of two-phase flow patterns inside the channel. A suitable range of gas to liquid ratio is from about 50:1 to about 1000:1. During at least a portion of the two-phase flow, the gas-liquid mixture is made to flow in the turbulent regime which provides very vigorous interaction between the liquid and the channel wall during flow. For example 10 ml of liquid will require 10,000 ml (10 liters) of gas to form the two phase flow mixture a 1000:1 gas-liquid ratio. If the volume of the channel is 10 milliliters, the number of volume changes (turnover volumes) of the two-phase mixture that will flow through the channel will be 1000 times. This means that the surface of the channel will be exposed to 1000 times its volume of the two phase flow mixture. This extensive contact between the liquid, propelled by the gas flow, provides tremendous interaction between the recovery liquid and the channel wall during recovery with the two phase flow technique. This extensive interaction of the recovery liquid with channel wall provides very high overall mass transfer rate for extracting and removing contaminants and residues from the passageway. There are also mechanical forces that can be generated at the channel wall during two-phase flow, and such forces can assist the recovery of adhering contaminants such as biofilms. Accordingly better recovery can be achieved with two-phase flow compared to conventional liquid flow recovery methods.

It should be noted that any embodiment that uses two phase flow can also use fluid without two phase flow.

Recovered liquid is liquid that has already passed through an endoscope channel, either once or more than once, and is then recovered and retained in a container. Recovered liquid can be either the liquid of a liquid-only flow or the liquid component of a two-phase flow. After any of these procedures, recovered liquid can be subjected to biological or biochemical testing. Such testing can comprise testing for the presence of organic soil, non-pathogens, pathogens, or can comprise culturing under specified conditions to promote the growth and multiplying of pathogens, followed by testing. Testing can include identifying the identity or strains of recovered pathogens, and quantifying their amounts or concentration. DNA-based techniques or other organism typing methods including mass spectrometry or other forms of spectroscopy can be used for identification according to the present invention, without limitation. Mass spectrometer measurements can be used to measure the Molecular Weight of DNA and RNA fragments, because even those measurements will be unique and can help to identify substances. It is also possible for organic soil to be assessed or analyzed by optical or spectroscopic techniques. One can also test for the presence of ATP (adenosine triphosphate) as an indicator of the presence of live microorganisms.

It can be noted that in some embodiments, if contamination is present, the method and apparatus can simply indicate that contamination is present somewhere in the endoscope, thereby demonstrating a need for the endoscope to be reprocessed again before use on a patient. In other embodiments, if contamination is present, the results not only indicate the presence of a contaminant but also indicate which channel contains contamination, or at least indicate a subset of channels among which the contamination is located. In still other cases, this sampling and recovery can indicate that the structural integrity of the endoscope was compromised and that the endoscope needs to be repaired before it is used again to treat patients.

In embodiments of the invention, if the endoscope is disinfected or sterilized prior to the described endoscope sampling procedure, the endoscope would remain disinfected or sterile as a result of the endoscope sampling procedure. In this case, the endoscope can be quarantined until the test results of recovered sample are completed before the endoscope can be used to treat patients. If the endoscope is found to be contaminated, it will need to be reprocessed or sent out for repair.

In some embodiments of the invention, if the endoscope is contaminated, the procedure would indicate the presence of contaminant without spreading such contaminant elsewhere such as to other channels or other surfaces of the endoscope. In some other embodiments, if the endoscope is contaminated, the procedure would indicate the presence of contaminant, but in so doing could spread contaminants within the endoscope to locations or channels within the endoscope other than where such contamination was originally located. At any rate, such a procedure would still serve the primary goal of detecting such contamination and preventing use of a contaminated endoscope on a patient. Following such an indication of contamination, repeated or further reprocessing of the endoscope would be required anyway, and would presumably remove all such contamination from either the original site or other sites, and would render the endoscope truly clean. After performing this second cleaning procedure, such cleanliness could then be verified by another performance of an endoscope sampling procedure of an embodiment of the invention.

In embodiments of the invention, there is provided a durable part of the system and one or more one-time use parts of the system.

The durable part of the system can for example generally be clean but not internally sterile, and can include apparatus that is not directly in contact with fluid that is delivered to or circulated through or received from the endoscope. For example, the durable part can include portions of pumps or compressors, such as the powered portions or associated surfaces, that are not directly in contact with fluid that is delivered to or circulated through or received from the endoscope or other medical device.

Separate from the durable part of the system, there can be a one-time-use module, kit or cartridge which can be assembled to the durable part of the system. The one-time-use module can be entirely sterile or can at least include some parts that are sterile. The one-time-use module can include parts that are in contact with fluid that is delivered to or circulated through or received from the endoscope. The one-time-use module can include parts that interface with the portions of pumps or compressors that are located in the durable part of the system. The use of a sterile single-use kit can be helpful for minimizing the possibility of false positive indications of contamination in endoscopes. The one-time-use sterile module can include a desired quantity of a sterile sampling liquid which is a one-time-use liquid.

A number of exemplary particular embodiments of systems of the invention are presented. These are provided to represent the main systems envisioned; however, combinations and hybrid combinations of systems are also contemplated according the present invention. Corresponding methods of use are also contemplated.

In the first exemplary embodiment (FIGS. 3-8), two-phase flow of air and liquid is caused to flow through the endoscope. The liquid fraction of the two-phase mixture only flows through the endoscope once, while the air can be filtered to make it organism-free and recirculated through the endoscope multiple times.

In the second exemplary embodiment (FIG. 9), two-phase flow of air and liquid is caused to flow through the endoscope. The air is supplied from an external source, and the sterile liquid is supplied from a sterile container. The air only flows through the endoscope one time and can be provided in a sterile condition, such as may be provided by a hospital-based source of clean air. In this sense, the air used in the recovery should not introduce organisms or contaminants that could compromise the sample collected from the endoscope. So, in this second embodiment, both the liquid and the air are one-time-flow-through.

In the third exemplary embodiment (FIG. 10), the sampling fluid is a single phase liquid only, and the liquid flows through the endoscope only once.

In the fourth exemplary embodiment (FIG. 11), the sampling fluid is a single-phase liquid only, and the liquid is circulated through the endoscope multiple times. In a fifth exemplary embodiment, the sampling fluid is a single-phase liquid only, and the liquid is circulated through the endoscope multiple times, but in between passes of the liquid it is filtered so as to remove the contaminants from the liquid and optionally to concentrate them.

Figure 3:
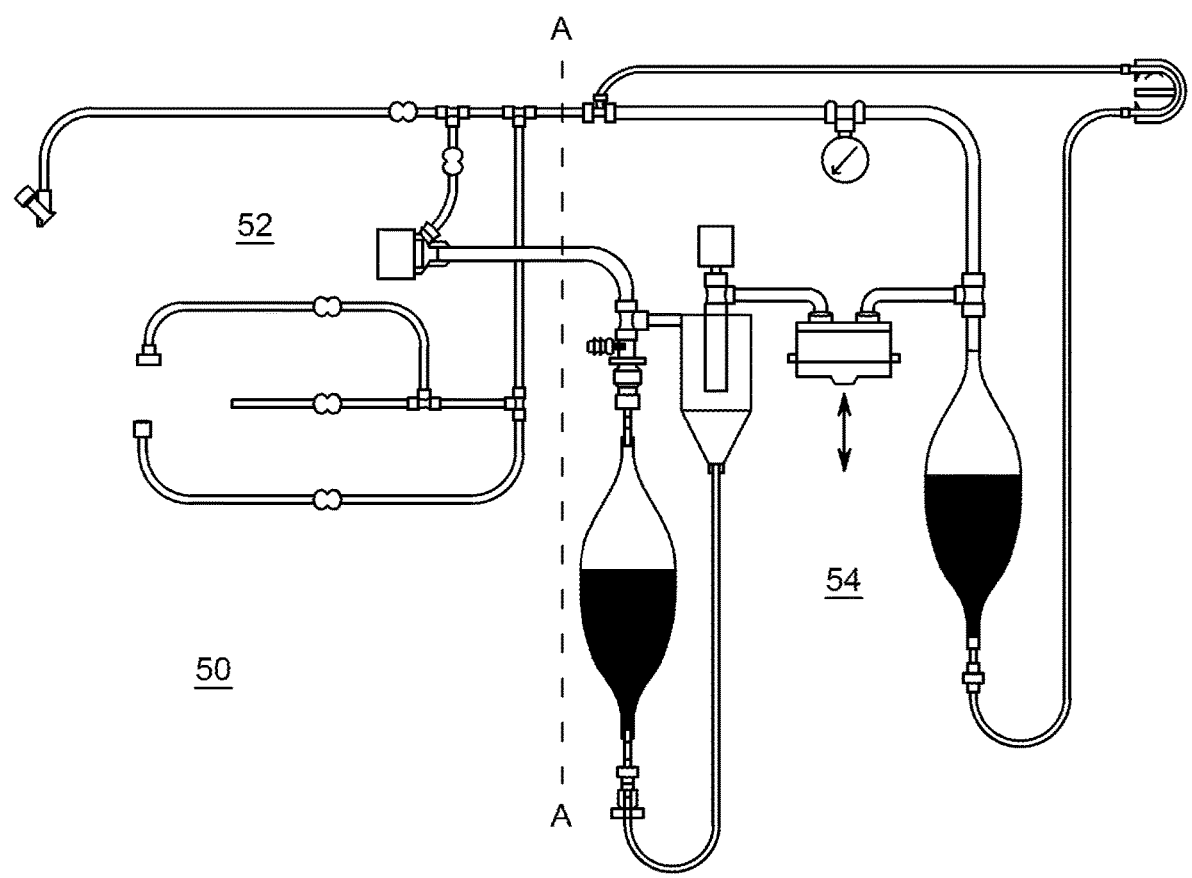
FIG. 3 is a lateral view of a first embodiment of an apparatus for testing endoscopes.

Reference is now made to the first exemplary embodiment of the invention as illustrated in FIGS. 3-8. In this embodiment, the air is filtered and is recirculated through the endoscope multiple times, while the liquid fraction only flows through the endoscope once. Referring now to FIG. 3, there is illustrated the system without showing the actual endoscope. There can be an endoscope test apparatus 50, which can be a sterile single-use kit or cartridge or cassette.

The endoscope test apparatus 50 can comprise an endoscope connectivity portion 52, which is shown to the left of the dotted line A-A in FIG. 3. Endoscope connectivity portion 52 can comprise various tubing and fittings and can be for example manufactured specific to the make and model of endoscope to be tested. Tubing and conduits that are used in the recovery and sampling kit for endoscopes can be supplied in a sterile condition. Any reliable method of sterilization can be used to sterilize the kits of the invention, as is known in the art of sterilization.

There is also shown a fluid handling portion 54, which is shown to the right of the dotted line in FIG. 3. The fluid handling portion 54 can comprise various containers, tubing, fittings and apparatus to the right of Line A-A.

Figure 4:
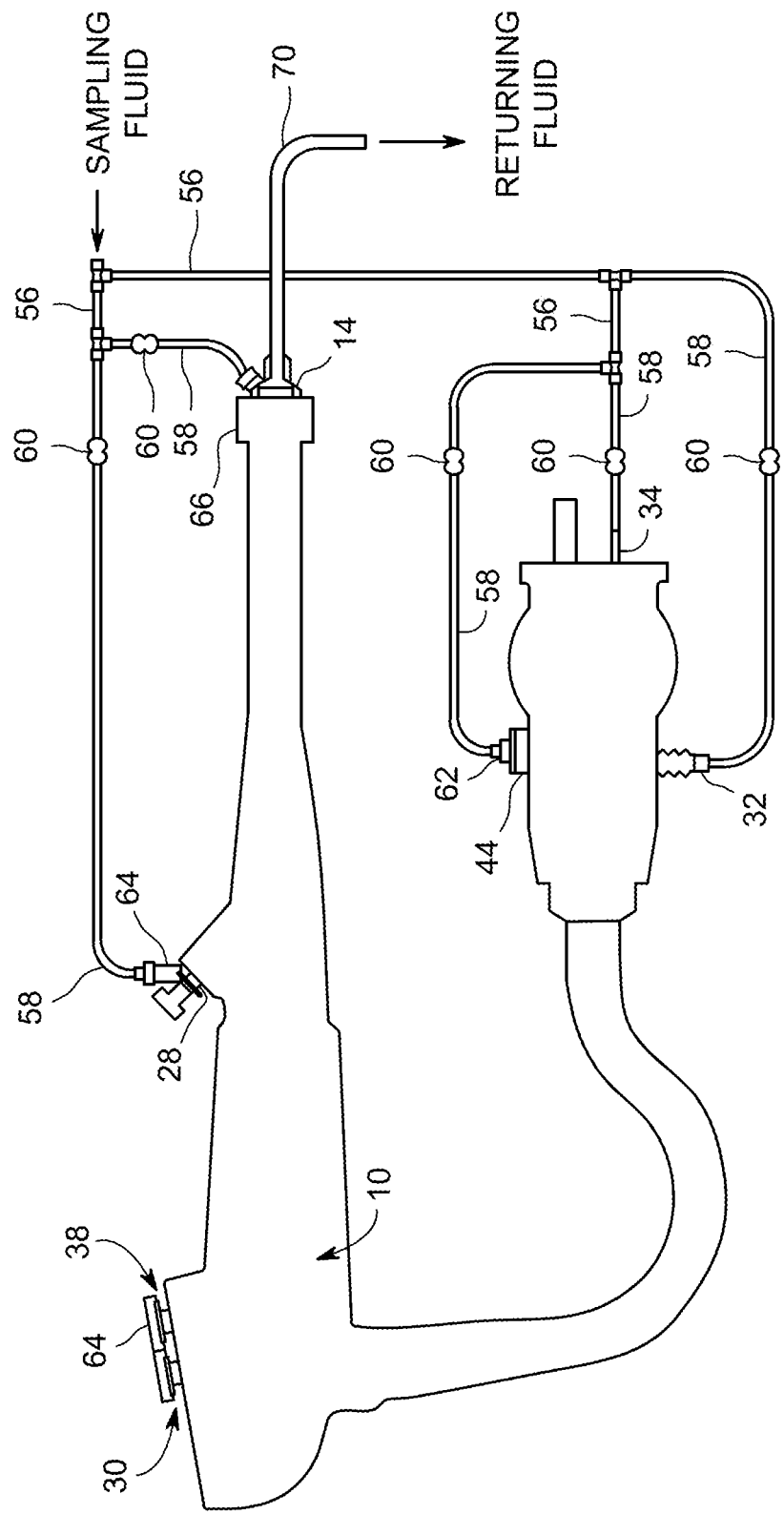
FIG. 4 is a lateral cross-sectional view of the endoscope of FIG. 1 with endoscope test apparatus connectivity portion attached.

Referring now to FIG. 4, the endoscope of FIG. 1 is shown with the connectivity portion 52 of endoscope test apparatus 50 attached to the endoscope 10. Connectivity portion 52 can comprise a plurality of interconnected distribution tubes 56 and connector tubes 58. The connector tubes 58 can have pinch valves 60, and can be configured so as to be able to selectively deliver a sampling fluid to appropriate fittings on endoscope 10 in a manner to cause the sampling fluid to pass through desired portions of or through the entire length of the channels in endoscope 10. Pinch valves 60 are illustrated as manually operated pinch valves, but alternatively these valves can be valves that are operated and controlled by an automated system. Connector tubes 58 can connect directly to endoscope fittings such as suction fitting 32, herein depicted as a barbed tubing fitting, or to connections such as air fitting 34, herein depicted as a straight rigid tube. Clamps can be utilized on these fittings to insure that the connection is secure. Other connector tubes 58 can terminate in a custom designed adaptor, such as adaptor 60 forming the connection to air/water fitting 44, or biopsy port adaptor 66 forming the connection to biopsy port fitting 28. A cylinder cap 64 can seal the open tops of suction cylinder 30 and air/water cylinder 38. In the illustration, the spools of the valves are not present. Thus it may be provided that all sampling fluid passing through the various endoscope channels exits only through distal tip 14.

Figure 5:
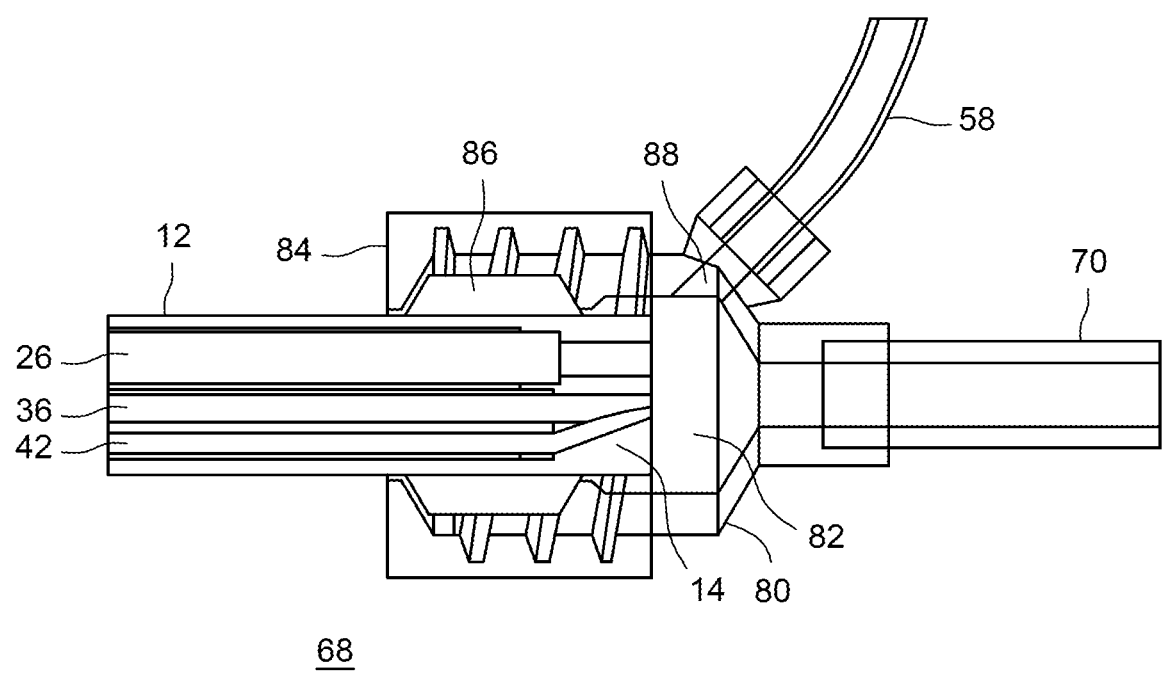
FIG. 5 is a partial lateral cross-sectional view of the endoscope of FIG. 4, illustrating the distal connector.

Referring now to FIG. 5, there is shown a close-up view of distal connector 68. Distal connector 68 can comprise a distal connector body 80. Distal connector body 80 can generally fit closely around the distal tip 14 of endoscope 10 and can receive fluids (either gas and liquid or both) flowing out of channels of the endoscope 10. Distal connector body 80 can have an internal collection chamber 82, a compression sleeve 86, and a compression nut 84. Distal connector 68 can also comprise a tip sampling port 88 such as in situations in which the endoscope to be tested has external mechanisms such as an elevator mechanism affixed to distal tip 14, or generally if distal tip 14 has features that can make cleaning especially difficult. During use, distal tip 14 of the endoscope 10 can be inserted into distal connector 68, through the center of compression nut 84, and through the center of compression sleeve 86, to a position partially within collection chamber 82. Compression nut 84 can then be tightened, squeezing compression sleeve 86 into contact with distal portion 12 and distal tip 14, to form a seal. Two-phase flow or sampling fluid, sent through the internal channels of the endoscope, can pass through distal portion 12 within internal tubes, such as suction tube 26, air tube 36, or water tube 42 as illustrated, and can exit distal tip 14, into collection chamber 82. Further, such fluid can exit collection chamber 82 through tube 70 to connectivity portion 52 of endoscope test apparatus 50.

An additional feature that can for example be built into distal connector 68 is a possible spray or jet that can be directed at the distal tip 14 of the endoscope 10. Such a spray or jet can be of particular interest for endoscopes that have elevators at their distal ends, because the elevator mechanism has been found to be particularly difficult to disinfect and is believed to be the source of unwanted transmission of infections in clinical use. If distal connector 68 has a tip sampling port 88, then a quantity of sampling fluid can be delivered via connector tube 58, to be directed through tip sampling port 88, to impinge on distal tip 14, and then exit through tube 70 to connectivity portion 52 of endoscope test apparatus 50. The orientation of tip sampling port 88 can be chosen to be appropriate to direct a fluid jet at hard-to-clean places associated with the distal tip 14 of endoscope 10. If desired, there can be provided a design feature to ensure that distal connector 68 can only be connected to endoscope distal end 14 at a particular angular orientation with respect to rotation around the longitudinal axis of the distal portion of endoscope 10. Such constrained angular orientation can be such that the fluid jet is directed in a desired orientation with respect to endoscope features such as the elevator mechanism or elevator channel. If desired, such impinging can be performed while the elevator mechanism is being moved through a range of positions.

Figure 6:
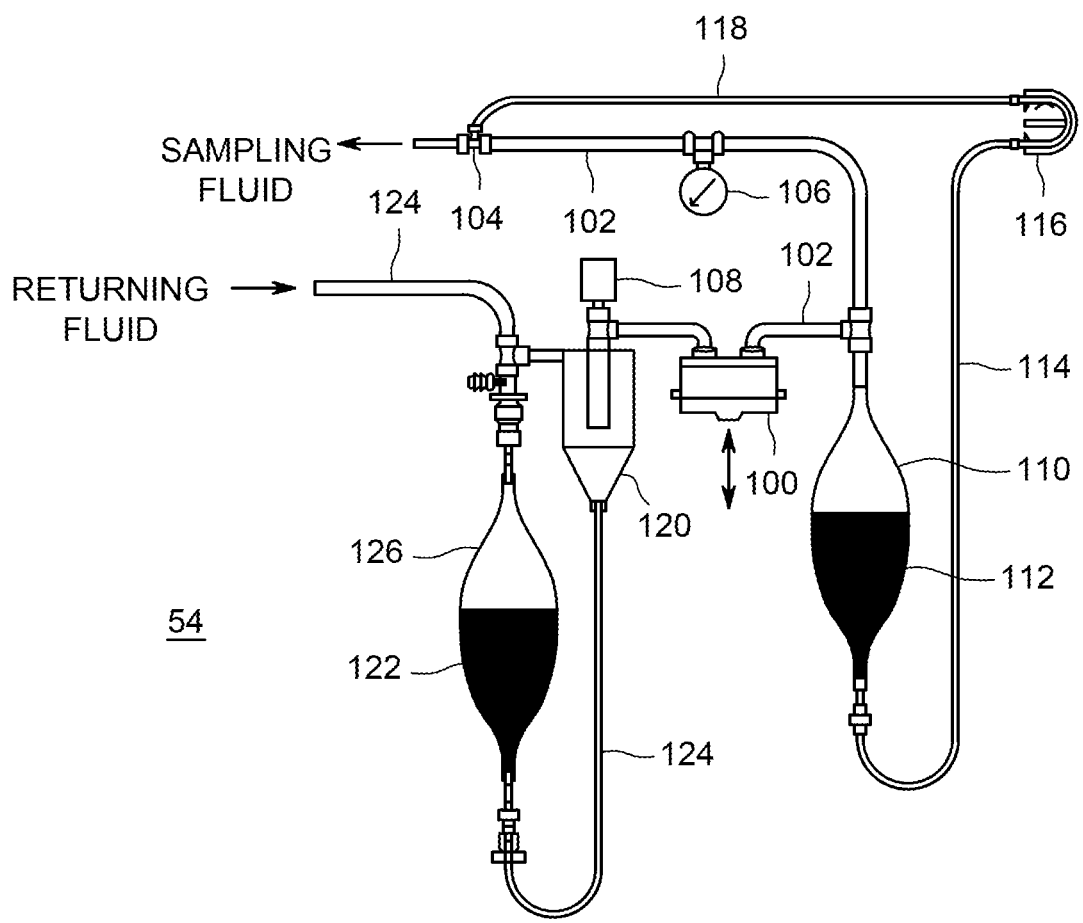
FIG. 6 is a lateral cross-sectional view of a first embodiment of a fluid handling portion of an endoscope test apparatus.

Referring now to FIG. 6, there are shown details of a fluid handling portion 54 of the endoscope test apparatus 50 of FIG. 3. Fluid handling portion 54 can generate and deliver to endoscope connectivity portion 52 a two-phase flow of air and liquid. An air pump 100 can force air through air tube 102, to mixing nozzle 104. It is intended that the term air pump 100 include compressors, pumps, blowers, and generally any mechanism that moves air or gas from a lower pressure region to a higher pressure region. A pressure measuring sensor 106 can be incorporated into air tube 102 and can provide feedback for controlling air pump 100 if desired.

A liquid pump 116 can move an appropriate quantity of sampling liquid 112 out of liquid supply chamber 110. Liquid pump 116 can be a peristaltic pump, as illustrated, but other types of pumps (such as piston pumps, motor-driven syringe pump, etc.) as are known in the art can also be used. Liquid pump 116 can be a metering pump in that it can be able to produce a relatively steady volumetric flow that is directly related to its rotation. Liquid that is pumped by liquid pump 116 can pass through metering pump input tube 114, through liquid pump 116, and through metering pump output tube 118 to mixing nozzle 104. At mixing nozzle 104, the sampling liquid 112 can combine with moving air to form a two-phase flow, which continues on to endoscope connectivity portion 52.

As illustrated in FIG. 6, there can be a connection from the output of air pump 100 to one end of the liquid supply chamber 110 containing sampling liquid 112. This connection can provide an elevated reference pressure for the sampling liquid 112 in the liquid supply chamber 110. The existence of this elevated reference pressure can mean that liquid pump 116 does not have to pump across a pressure difference that is the full pressure generated by air pump 100, but rather would only have to pump across a smaller pressure difference. Peristaltic pumps, in particular, have some limitations as to the achievable pressure difference. Because of this elevated pressure experienced within liquid supply chamber 110, in embodiments, the liquid supply chamber 110 can be surrounded by a structural chamber (not illustrated). Such structural chamber can be made in parts so that it can be opened or disassembled for installation or removal of liquid supply chamber 110. Alternatively, liquid supply chamber 110 can be provided without a connector tube, or the connector tube can be closed off. In such case, liquid supply chamber 110 can be made with greater inherent strength. It is also possible that an elevated reference pressure can be achieved not by delivering the output of air pump 100 to the interior of liquid supply chamber 110, but rather merely exposing the exterior of liquid supply chamber 110 to an elevated pressure such as the output of air pump 100. This can be done if liquid supply chamber 110 is deformable, such as a bag. Such a deformable liquid supply chamber can be surrounded by or enclosed in a structural chamber (not illustrated).

After flow has flowed through the endoscope 10, two-phase flow exiting from the endoscope connectivity portion 52 can enter separator 120, where the liquid portion of the two phase fluid is separated from the air. Separator 120 can be a cyclone type of separator, for example. In embodiments the separator and possibly a filter adequately remove contaminants from the air so that the air can be recycled through the endoscope. The air can be returned to air pump 100, and sample liquid 122 can be drained from separator 120 through sample tube 124, into receiving container 126. A make-up air filter 108 can allow atmospheric air to enter or system air to exhaust, so as to maintain air pressure within separator 120 at approximately atmospheric pressure or slightly above atmospheric pressure.

Liquid supply container 110 and receiving container 126 can be rigid containers made from polymers or glass, or they can be flexible containers as are commonly used in the healthcare industry. Flexible containers are commonly manufactured by heat welding thermoplastic films to form a sealed bag structure.

At the beginning of the endoscope sampling procedure, liquid supply container 110 can be full of sampling liquid 112, and receiving container 126 can be empty. At the completion of testing the majority of sampling liquid 112 can have been sent through the various channels of endoscope 10 and returned as recovered liquid 122, stored in receiving container 126. Receiving container 126 can then be disconnected from fluid handling portion 54 of endoscope test apparatus 50, closed off, and sent to an appropriate test facility wherein sample liquid 122 can be analyzed for the presence of any pathogens. The remainder of endoscope test apparatus 50 can be discarded.

In embodiments of the invention, endoscope test apparatus 50, subcomponents of air pump 100 and pressure measuring sensor 106, that are not in direct contact with the gas being circulated through endoscope test apparatus 50 can be consolidated into a durable, reusable module. Likewise, subcomponents of liquid pump 116 that are not in direct contact with sampling liquid 112, can be consolidated into the durable, reusable module of permanent equipment. Separate from the durable reusable module, there can be a one-time-use module to which the balance of endoscope test apparatus 50 is assembled for use.

Figure 7:
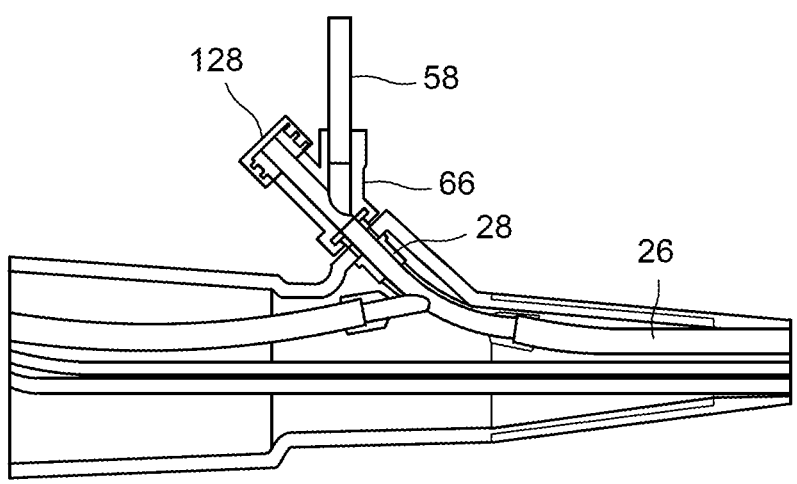
FIG. 7 is a partial lateral cross-sectional view of the endoscope of FIG. 4, illustrating the biopsy port adaptor.

FIG. 7 is a close-up view of the biopsy port adaptor 66 connected to biopsy port fitting 28 of the endoscope. During a portion of the endoscope testing procedure, two-phase flow or sampling fluid can be delivered through connector tube 58, and can pass through biopsy port adaptor 66, and through biopsy fitting 28, and through suction tube 26.

Some endoscope reprocessing procedures can include the use of a small brush or swab disposed on the end of a long flexible shaft. Such a procedure can be useful for a channel such as the suction/biopsy channel. In a typical endoscope that has a suction/biopsy channel, the suction/biopsy channel typically has a larger inside diameter than the other channels of the endoscope, and therefore such channel is more likely to allow a brush or swab to pass a brush through it. At the same time, the suction/biopsy channel is also more likely than other channels to be contaminated with pathogens. Therefore, the suction/biopsy channel can be a candidate to be cleaned with a brush or swab during endoscope reprocessing. Passage of a brush or swab through the channel can be driven by a drive mechanism.

Because a channel such as the suction/biopsy channel can be capable of allowing a brush or swab to pass through it during endoscope reprocessing, it can also be useful to pass a brush or swab through such a channel during the endoscope sampling or recovery procedure of embodiments of the invention. Such a brush or swab can be an effective device for picking up at least a sample of any contaminants that may remain inside that channel, or to make the recovery more efficient or more complete. If a brush or swab is passed through a channel during endoscope sampling, it can be desirable that the brush or swab be subjected to bacteriological or biochemical testing similarly to performance of testing on the collected fluid. It is believed, although it is not wished to be limited to this explanation, that if contamination or microorganisms are present in the endoscope, such a brush or swab can capture or retain a notable amount of such contamination or microorganisms. Accordingly, it can be desirable to provide, in the endoscope sampling system, a means for separating the brush or swab from its drive shaft so that the brush or swab can become part of the recovered material needed for sampling. The brush or swab can then be included in the contents of whatever is sent to a laboratory for testing. Before culturing or analyzing the recovered material, the tip of the brush or swab as well as the recovered liquid can be sonicated or vortexed or both to detach and disperse the recovered organisms and organic soil.

Accordingly, there can be provided a cut-off knife 142 (FIG. 8), which can be slidably mounted in cut-off knife channel 144 near a channel through which the brush or its driving shaft can pass. Such cut-off knife 142 and cut-off knife channel 144 can be located near the entrance to receiving container 126. Other components or mechanisms functioning similarly to a knife can also be provided. Such components or mechanisms may be designed in cooperation with the design of the attachment between the driving shaft and the brush or swab.

Figure 8:
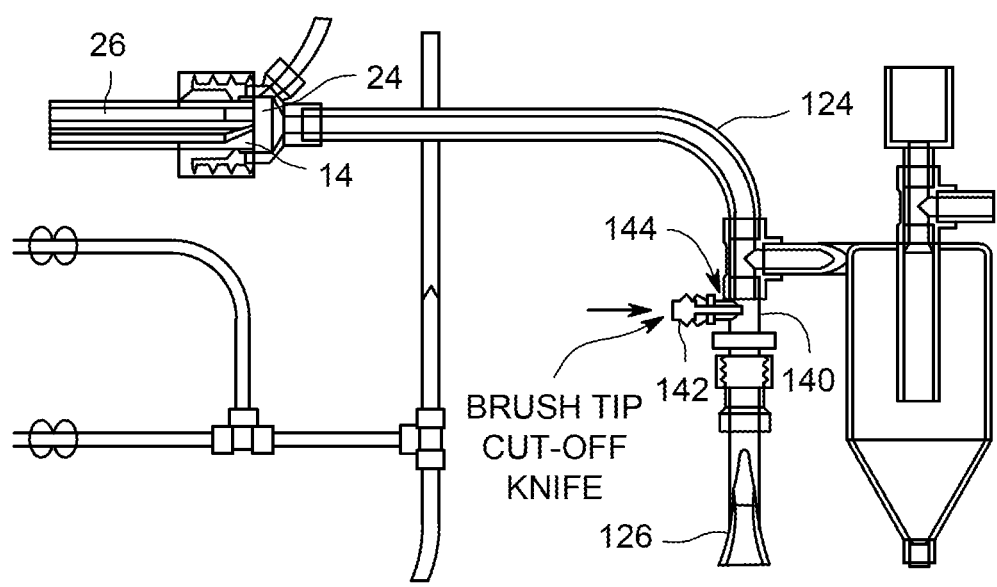
FIG. 8 is a partial lateral cross-sectional view of an endoscope with attached endoscope test apparatus, illustrating a brush tip cut-off knife.

When such a step is performed, referring now to FIG. 8, the brush or swab (not shown) can be extended beyond the endoscope channel until the brush tip or swab passes through suction port 24 in distal tip 14, through tube 70. The cut-off knife 142 can then be actuated in the direction indicated by the arrow in FIG. 8, so as to sever or detach the brush or the swab from the long flexible shaft that drives the brush or swab. The brush or swab can then deposit into the sample container 126, which also contains (or will contain) the liquid that has flowed through the endoscope for sampling purposes. The remainder of the shaft can then be withdrawn through biopsy port adaptor 66. Biopsy adaptor cap 128 can then be placed back on biopsy port adaptor 66. It is further possible, after this step, that additional sampling fluid can be sent through the channel that the brush or swab has passed through, in order to flush any remaining loose materials into receiving container 126.

In embodiments of the invention that used mixed-phase flow of gas and liquid, it is possible to use a variety of fluid flow regimes and ratios of gas flow to liquid flow. Generally, there may be a larger gas fraction than liquid fraction (on a volumetric basis), so that at least some of the liquid exists in discrete entities such as droplets or rivulets and is moved along by the velocity of the flowing gas, which may have a fairly large velocity. For example, in embodiments of the invention, the volumetric gas to liquid ratio may be at least 50:1. Related methods and apparatus are described in the following patents by some of the same inventors: U.S. Pat. Nos. 9,492,853; 8,747,569; 8,226,774; 8,114,221; 8,083,861; 7,862,660; 7,367,346; 6,945,257; 6,857,436; 6,619,302; 6,454,871; 6,326,340; 6,027,572, which are incorporated herein by reference in their entirety.

Figure 9:
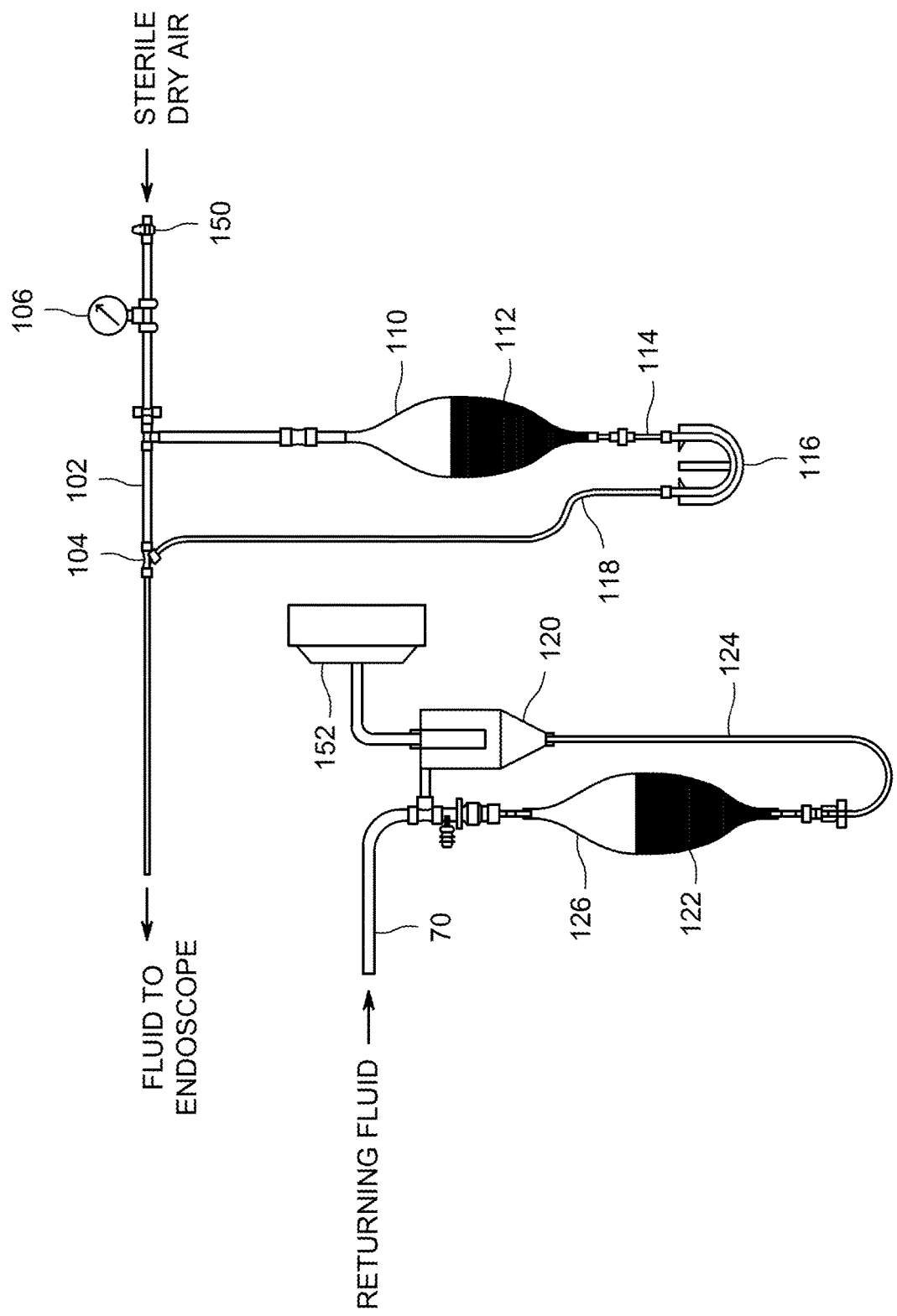
FIG. 9 is a lateral cross-sectional view of a second embodiment of a fluid handling portion of an endoscope test apparatus.

A second exemplary embodiment of the invention is illustrated in FIG. 9. FIG. 9 depicts a second embodiment of a connectivity portion of an endoscope test apparatus. In this embodiment, sterile, dry compressed air can be supplied from an external source, as can be available in many hospitals. The externally supplied air is assumed to be sterile, based on the properties of the supply system that supplies the air. In this embodiment, both the liquid and the air are one-time-flow-through the endoscope. In this embodiment, the air only flows through the endoscope one time and then, after passage through a separator or filter, is discharged to the atmosphere. A suitable HEPA (High Efficiency Particulate Arresting) filter can be used to ensure that the air used in the test is free of organisms. In this embodiment, the liquid only flows through the endoscope once and then is collected in the receiving container 126.

Similarly to what is described in other embodiments, pressure regulator 150, pressure measuring device 106, and portions of liquid pump 116 that are not in direct contact with sampling fluid 112, can be incorporated into a durable, reusable module. The supply of incoming air can connect to the durable reusable module.

Air can enter mixing nozzle 104, and simultaneously liquid pump 116 can move an appropriate quantity of sampling liquid 112 from liquid supply chamber 110, through metering pump input tube 114, through liquid pump 116, and continuing through metering pump output tube 118 to mixing nozzle 104. At mixing nozzle 104, the gas flow and the liquid flow can be combined to form a two-phase fluid, which can be delivered to the endoscope.

Two-phase fluid can be delivered to the endoscope at relatively high pressure, consistent with pressure limits imposed on the endoscope for structural reasons. It can be expected that most of the pressure drop downstream of fluid delivery to the endoscope occurs along the length of the passageways inside the endoscope. It can be expected that two-phase fluid leaves the endoscope at approximately atmospheric pressure or only slightly above atmospheric pressure.

Two-phase flow received from the endoscope can enter separator 120. In separator 120, the liquid portion of the two-phase fluid can be separated from the air. The air can be exhausted through air discharge filter 152, and sample liquid 122 can be drained from separator 120 through sample tube 124, into receiving container 126.

Figure 10:
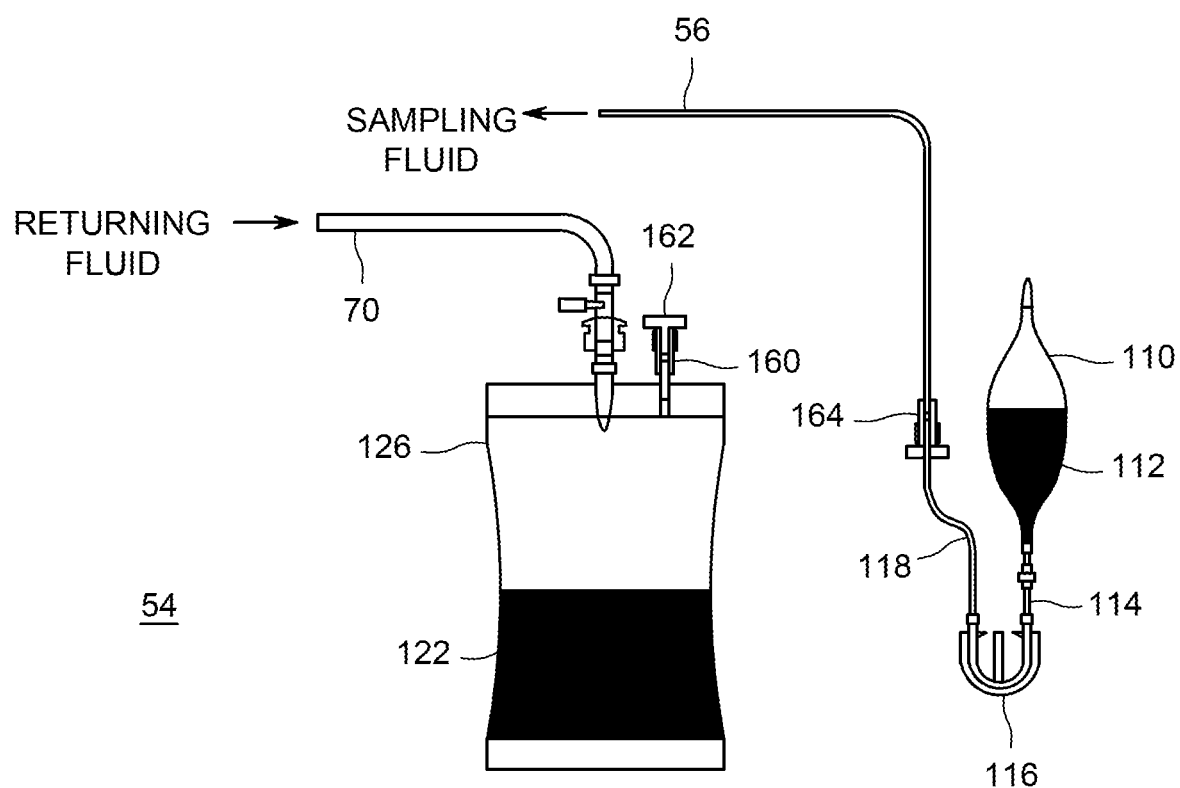
FIG. 10 is a lateral cross-sectional view of a third embodiment of a fluid handling portion of an endoscope test apparatus.

A third exemplary embodiment of a fluid handling portion 54 of an endoscope test apparatus 50 is illustrated in FIG. 10. In this embodiment, the sampling fluid can be a single-phase liquid only, and liquid pump 116 can move sampling liquid 112 from liquid supply chamber 110, through metering pump input tube 114, and through metering pump output tube 118 to distribution tube 56 of endoscope connectivity portion 52 of endoscope test apparatus 50.

Fluid returned from endoscope connectivity portion 52 through tube 70 can be deposited into receiving container 126.

At the completion of the testing procedure, when receiving container 126 has been emptied, liquid supply chamber 110 can be disconnected at supply connector 164, and can be discarded. A syringe containing air, or some other source of sterile air, can be connected at supply connector 164, and can be used to purge all sample fluid from endoscope connectivity portion 52, and endoscope 10. Vent cap 162 can be removed from vent fitting 160, to allow any air to escape from receiving container 126.

After the completion of flowing fluids through the endoscope, receiving container 126 can be disconnected from fluid handling portion 54 of endoscope test apparatus 50, closed off, and sent to an appropriate test facility where sample liquid 122 can be analyzed for the presence of any pathogens. The remainder of endoscope test apparatus 50 can be discarded.

Figure 11:
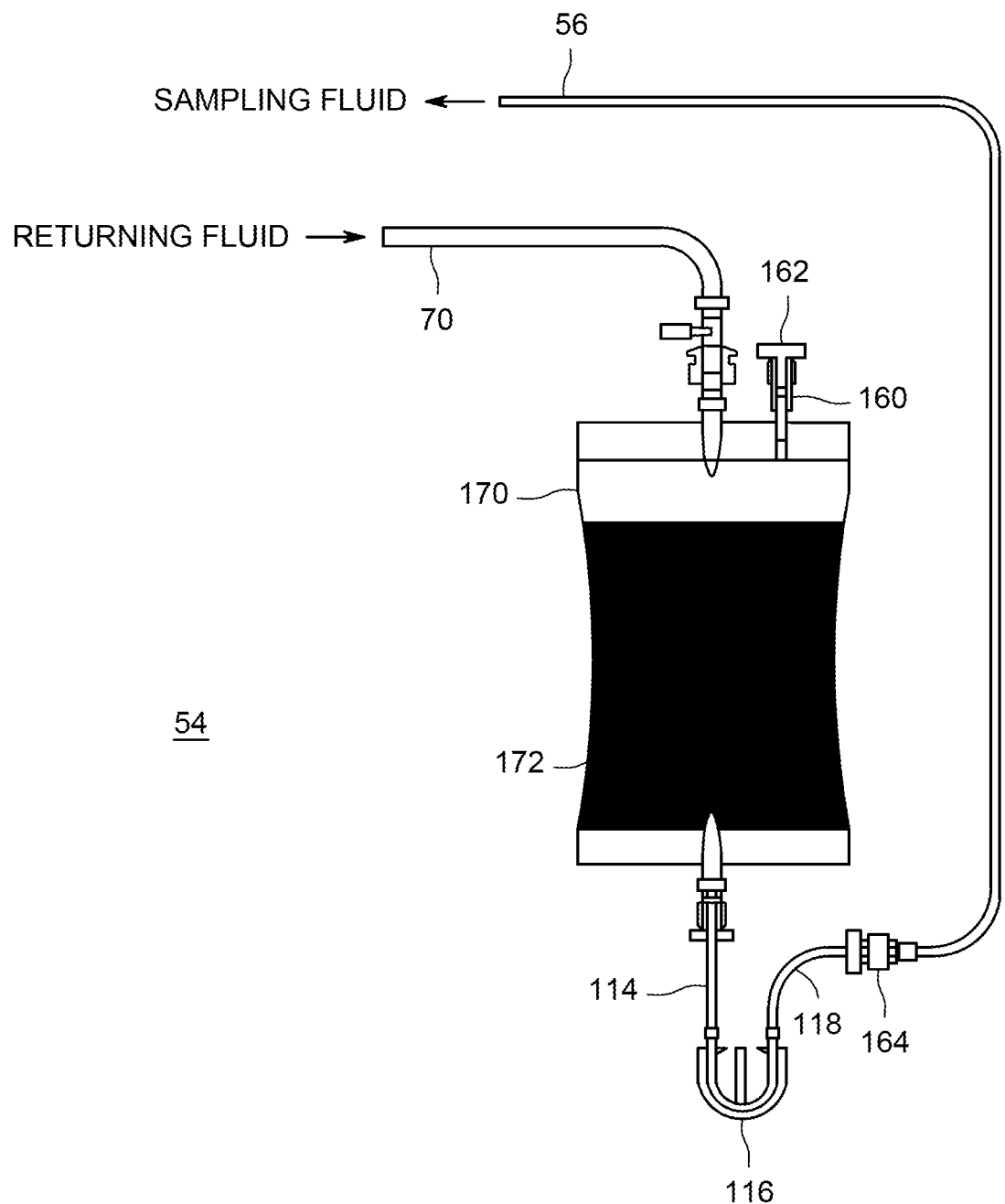
FIG. 11 is a lateral cross-sectional view of a fourth embodiment of a fluid handling portion of an endoscope test apparatus.

A fourth exemplary embodiment of a fluid handling portion 54 of an endoscope test apparatus 50 is illustrated in FIG. 11. In this embodiment, the sampling liquid can be a single-phase liquid only, and liquid pump 116 can move test solution 172 from test solution container 170, through metering pump input tube 114, and through metering pump output tube 118 to distribution tube 56 of endoscope connectivity portion 52 of endoscope test apparatus 50.

Fluid that is returned from endoscope connectivity portion 52 through tube 70 can be deposited back into test solution container 170. In this embodiment, test solution 172 can be circulated through endoscope connectivity portion 52 and endoscope 10 multiple times, allowing the use of a smaller quantity of test solution, and increasing the concentration of collected contaminants or microorganisms in the test solution. It can be advantageous to recirculate liquid, in that the use of recirculation can cause the liquid to collect more contaminants and achieve a larger concentration of contaminants in the liquid, compared to the situation in which the liquid only passes through the endoscope one time. This is true for both liquid-only and two-phase flow systems. However, if contamination is present in only one channel, such recirculation could spread the contamination to other channels (except in a system provided under the invention that directs fluid separately to each channel).

At the completion of the testing procedure, distribution tube 56 can be disconnected at supply connector 164. A syringe containing air, or another sterile air source, can be connected at supply connector 164, and used to purge all sample fluid from endoscope connectivity portion 52, and endoscope 10. Vent cap 162 can be removed from vent fitting 160, to allow any air to escape from test solution container 170.

Test solution container 170 can then be disconnected from fluid handling portion 54 of endoscope test apparatus 50, and can be closed off and sent to an appropriate test facility wherein test solution 172 can be analyzed for the presence of any pathogens. The remainder of endoscope test apparatus 50 can be discarded.

Receiving Container

Figure 12:
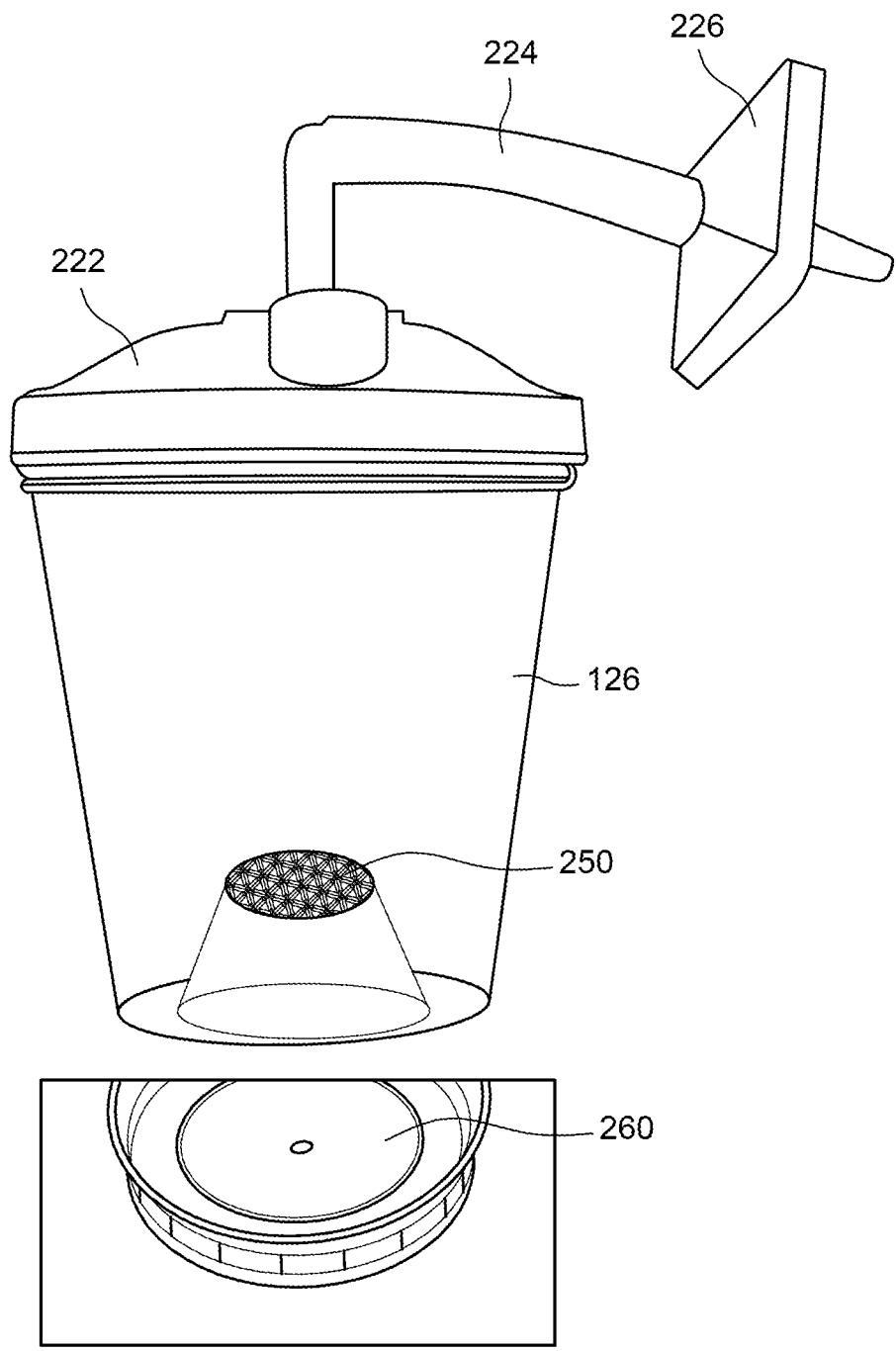
FIG. 12 shows a receiving container that can receive fluids that have passed through an endoscope during a sampling procedure. The receiving container includes a filter.

Referring now to FIG. 12, in an embodiment of the invention, there can be provided a receiving container 126. Receiving container 126 can be suitable to retain contaminants that can be extracted from the medical device during the testing/assessment procedure, and to keep those contaminants isolated from the environment until microbiological testing and other analyses can be performed. The receiving container 126 can, for example, have an internal volume that is in the range of approximately 20 milliliters to 1000 milliliters. The receiving container 126 can be provided in a sterile condition and can be packaged appropriately to maintain its sterility until use.

Receiving container 126 can comprise two ports. One of the ports can be designated an inflow port 222 and the other can be designated an outflow port 224. In use, the inflow port 222 can be connected so as to receive material that has passed through the medical device, such as material carried along by a fluid flowing through the medical device. Outlet port 224 can comprise a filter through which exiting air can pass.

Material that enters the receiving container 126 can comprise any one or more of gas, liquid, or their mixtures, and can be or include a suspension including semisolid or solid components. Liquid or solid components can include contaminants/microorganisms, organic soil components including protein, carbohydrate, patient materials and others, as well as the liquid in which the contaminants/microorganisms are contained. Upstream of the outflow port 224, there can be provided a filter or gas-liquid separator 120 to separate and retain non-gaseous material that has exited from the medical device that is being tested or cleaned. The receiving container and system can be such that gaseous material exiting from the medical device is able to pass through the filter or separator 120, while exiting material that is non-gaseous, such as liquid or solid, is completely or mostly retained in either the receiving container 126 or the filter 226 or both. The filter 226 can, for example, be a High Efficiency Particulate Arresting (HEPA) filter. A separator 120 can comprise a centrifugal separator such as a cyclone, for example. Of course, both a filter 226 and a centrifugal separator 120 can be used together. The separator 120 can separate two-phase flow into gas and recovered liquid. A concentrator such as filter 250 or the device 180 can separate recovered liquid into two types of liquid, namely a filtrate and a concentrated form of the recovered liquid (which contains substantially all of the recovered contaminants, but contains less liquid).

Figure 13:
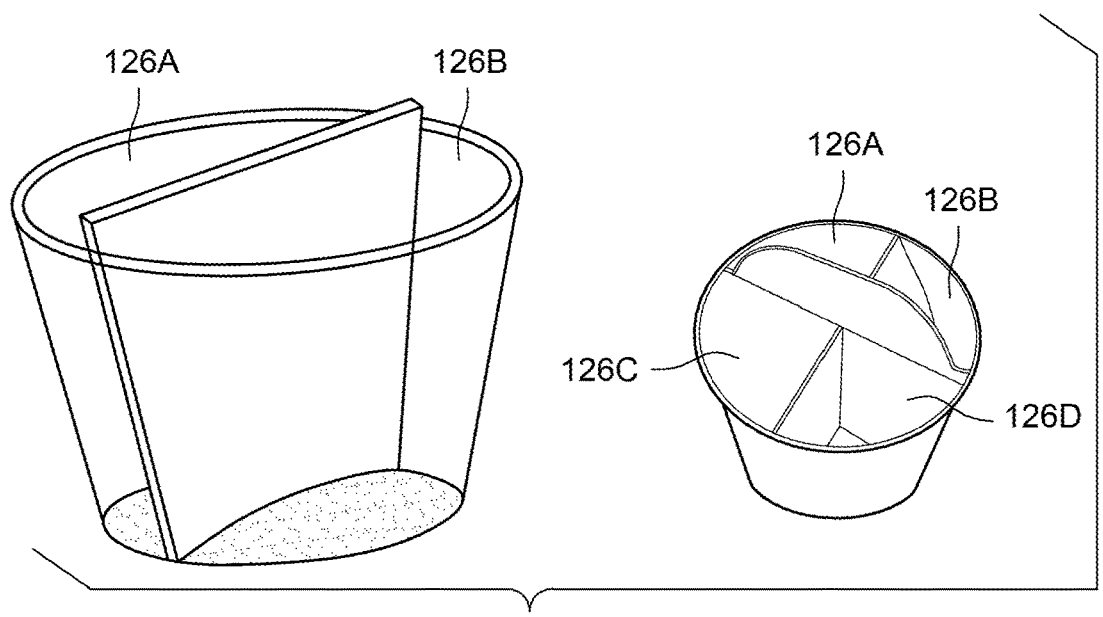
FIG. 13 shows a multi-compartment receiving container that can receive fluids that have passed through an endoscope during a sampling procedure.

Referring now to FIG. 13, it is further possible that the receiving container 126 can comprise more than one chamber 126A-D, such that each chamber 126A-D is devoted to capturing or retaining non-gaseous material that has exited from a particular channel of the endoscope. Each chamber 126A-D can comprise two respective ports, which as already discussed can be designated an inflow port and an outflow port. There can be a filter associated with each of the individual outflow ports of the chambers 126A-D of the receiving container 126. Similarly to previous discussion, a chamber 126A-D of the receiving container 126 can receive the effluent from one or from more than one of the channels of the medical device but less than all of the channels of the medical device. Such a receiving container 126 can make it possible to determine the sterility or contamination status of individual channels or sub-groups of channels of an endoscope 10. In this situation, if an endoscope 10 is found to have contamination, this system would provide at least some information about where within the device the contamination originated, rather than simply providing a general indication that contamination exists somewhere in the medical device such as an endoscope 10.

In embodiments, the receiving container 126 itself can contain a reagent that reacts with a contaminant so as to provide an indication of the presence of contamination, possibly even without further processing of the receiving container 126. Such reagent can detect the presence of adenosine triphosphate (ATP). ATP is known to be an indicator of cellular activity and of the presence of living cells. Such reagent can be located inside the receiving container 126. Other reagents can be included to preserve DNA and proteins for subsequent analyses according to embodiments of the invention. The receiving container can also include neutralizers (as known in the literature) for high-level disinfectants such as aldehydes, peracids and others, as described elsewhere herein. The neutralizers can be present to avoid compromising the viability of collected organisms. Where the ATP detection is by generating light, the receiving container can be shielded from outside light, and a photodetector can be positioned to detect the light signal.

In embodiments, the receiving container 126 can be supplied containing inside it a growth medium suitable to grow bacteria that may be received from the endoscope, even without sending the receiving container 126 to a testing laboratory, or prior to sending the receiving container 126 to a testing laboratory. Growth media are discussed in "Culture Conditions and Types of Growth Media for Mammalian Cells" by Zhanqiu Yang and Hai-Rong Xiong (Biochemistry, Genetics and Molecular Biology»"Biomedical Tissue Culture", a book edited by Luca Ceccherini-Nelli and Barbara Matteoli, ISBN 978-953-51-0788-0).

Of course, the receiving container 126 can contain both an ATP-detecting agent and a growth medium.

The receiving container 126 can simply be sent to a testing laboratory as soon as endoscope sampling is performed. Testing at a laboratory could provide a more accurate or detailed result about the extent or nature of contamination that may be contained inside the receiving container 126, compared to tests that can be performed within the receiving container itself.

The receiving container 126 can be provided in a sterile condition and can be packaged appropriately to maintain its sterility until use. Similarly, other components associated with the receiving container 126, including its filter(s), reagent if present, growth medium if present, and associated tubing valves and other components, can be provided in a sterile condition and can be packaged appropriately to maintain such sterility until the packaging is opened near the time of use.

In an embodiment of the invention, substantially the entire sample collected in the receiving container can be filtered so that all or almost all of the organisms are retained on the surface of the filter. This filter can be placed on a suitable culture media to determine the nature and amount of bioburden either in the same facility where the sample is collected or by sending it out to an outside laboratory. The filter can also be sent out in the receiving container used in the recovery in order to avoid cross-contamination or other process that can compromise the analysis.

The described components can be used in connection with a two-phase flow of liquid and gas through the channels to be tested. As one possibility, the flow of either the liquid or the gas or both can be substantially steady or can be non-steady with respect to time. Additional possibilities include pulsatile flow of either the liquid or the gas or both. In embodiments, the supply conditions of either liquid or gas can vary as a function of time. In embodiments, the ratio of liquid flow to gas flow can vary as a function of time. It is also possible that the described components and techniques can be used in combination with a flow of liquid of liquid alone along the length of the channel, or a flow of gas alone along the length of the channel, or combinations thereof.

Sampling Connectors to Endoscope

In embodiments of the invention, there can further be provided appropriate tubing sets and connectors so as to achieve the desired flow and other sampling procedures. Such components can be supplied in a sterile condition and can be packaged appropriately to maintain sterility until use.

Connectors that are supplied can be unique to a particular design of endoscope and unique to particular connection points on the endoscope. In fact, connectors can be designed so as to reduce or eliminate the possibility of incorrect connection to an endoscope, or to avoid cross contamination during the act of connecting to or disconnecting from the endoscope or medical device.

If flow of any fluid is to be supplied to a channel of a medical device, connectors can be supplied appropriate to connect to either the individual channel, or two channels, or a subset of channels, or the device as a whole. In embodiments, the supplied tubing can comprise bifurcations so that the tubing set can provide sterile sampling liquid, or two-phase flow including sampling liquid, to multiple channels simultaneously through individual connectors.

For an endoscope or similar device, one possible connection point is at the distal end of an endoscope. At the distal end, typically several channels are open, and typically the openings are located within a fairly small overall space or dimension of the distal end. Some endoscopes have an elevator channel that is open at the distal end, while other endoscopes do not have an elevator channel at all. Many endoscopes have an opening at the distal end for the suction/biopsy channel. Many endoscopes have one or more openings at the distal end for some combination of air, water, irrigation and carbon dioxide, which can combine with each other to form some smaller number of openings at the distal end of the endoscope even if the channels are separate channels within most of the endoscope.

Because of how close the various channels are to each other at the distal end of the endoscope, it can be difficult or impractical to form a fluid-tight seal to an individual channel or to more than one individual channel simultaneously. Such a connector can use a connector having a separating wall and seal between channels that are quite close to each other, and such a separating wall and seal might have some dimensions that are small and difficult to achieve or need to maintain alignments that are difficult to maintain.

Accordingly, one option is to provide simply one connector that connects to all of the openings at the distal end of the endoscope. Such a connection can, if desired, be a discharge connection for flow, with the supply connection(s) being elsewhere on the endoscope.

Alternatively, it can be possible to connect with individual channels at the distal end by providing an adaptor or distal connector 68 that is matched to only one channel and not serving any other channels. In such a situation, the rest of the interface of that connector can be used to block all other channels. Then, in order to be able to follow through and connect individually with another particular channel, it can be necessary to use an additional adapter that corresponds to that other particular channel.

It can further be noted that some channels have more connection or access points along their length than just two ends. For example, the suction/biopsy channel can be notable in this regard. The suction/biopsy channel can have (first) an opening at the distal end of the endoscope. Then (second), at the handle, there can be a place where the biopsy port joins to the channel; also at the handle, there can be (third) a valve spool access point to that channel; and (fourth), there can be an opening at the umbilical end of the endoscope. In the system of an embodiment of the invention, there can be provided fluid connection adaptors that connect to the channel at two of these locations, with one of the adaptors being a supply and the other being a return. It can be noted that for operations such as the described sterility testing/assessment, the spools of the spool valves can be removed, just as they would likely be removed during cleaning. Furthermore, there can be provided plugs or blockages that connect to others of these locations, such as whatever locations are not occupied by the supply connector and the return connector. Such plugs or blockages as used here or elsewhere can be provided in a sterile condition and can be appropriately packaged to maintain sterility until use.

Still further, it can be noted that some endoscope access points that may be in the form of spool valves that interact with more than one fluid channel of the endoscope. For example, a spool valve can interact with both the air line and the water line. For such geometries, the one-time-use kit can include plugs or blockages that are designed and dimensioned to engage with the housing of a spool valve. The plug or blockage can be designed so that it interacts as desired to block one or the other (or both) of the fluid lines that interact with that spool valve, yet it can, in some embodiments, leave another channel open if desired.

For purposes of introducing a brush or swab, in embodiments, tubing in the tube set of a one-time-use component can comprise a "Y" joint. One leg of the "Y" joint can be a fluid path, and the other leg can be a path for introducing the brush or swab.

Concentrator

In a typical sampling procedure that involves causing liquid or liquid plus gas to flow through the channel, the amount of liquid that would be collected, containing possible contaminants, can be in the range of 150 to 250 cubic centimeters (cc) or more in some endoscope models. It would be possible, in some protocols, to simply close the receiving container 126 and send the receiving container 126, containing all of that liquid, to a laboratory such as a microbiology or DNA laboratory for testing. However, there can be advantages to concentrating the collected liquid before sending the receiving container 126 to a laboratory.

If such a concentrating step is performed, the volume of fluid that would need to be sent to a laboratory for testing can be reduced by a large factor, and this can result in some financial savings on the cost of shipping, and hence the cost of the overall testing. Furthermore, there can be another advantage beyond a simple economic advantage. In embodiments, the testing procedure itself might involve using only a small amount of material for purposes of culturing microorganisms. The testing procedure very likely does not need to use all of the sampling liquid that was recovered from the endoscope, and even if concentrating is performed, the testing procedure can only use a sample of the concentrated material. Accordingly, from a sampling point of view, it is advantageous if the fluid that is used for culturing or analysis, starts out with a sample containing as large as possible a concentration of microorganisms or contaminants. For example, if the testing procedure involves culturing of cells or microorganisms, there might not be a need for as much culturing as would otherwise be the case. There is even the simple consideration that if the concentration of a contaminant or microorganism is sparse, it is possible that taking a sample for testing could fail to include any members of a species that is present in a sparse concentration, resulting in a failure to detect that species.

In embodiments of the invention, there is provided a system and method for concentrating the recovered liquid and/or solid material after the completion of the sampling process. In one such embodiment, the receiving container 126 can be suitable to be spun in a centrifuge for purposes of concentrating certain material. The receiving container 126 can have an appropriate geometry for centrifugation and can have a port or ports for removing either the concentrate or the supernatant after centrifugation, as desired.

In another embodiment, with reference to FIG. 12, there can be provided a concentrating filter 250 built into or associated with the receiving container, such that the recovered liquid can be passed through the concentrating filter 250, and the concentrating filter 250 would retain all or a large fraction of the recovered microorganisms and contaminants. For example, the concentrating filter can have a size cutoff or pore size of about 0.2 microns. In other cases, the pore size of the filter can be selected to retain viruses and this case filters with pore size of 50 nm or smaller can be used. In still other cases a filter that can retain DNA can be used so that subtyping using real-time DNA, FISH or mass spectroscopy of DNA fragments can be conducted. In this sense, the invention might not be limited to culturing bacteria or fungus, but can accommodate other testing and analysis of DNA or proteomics as needed.

Presumably the liquid and material that remains behind would contain all or almost all of the microorganisms and contaminants that were recovered from the endoscope. Material that is retained by the concentrating filter would be analyzed or cultured or sent to a laboratory. Presumably the material that passes through the concentrating filter can be substantially pure water, or can contain other contaminants that are soluble or extremely small, such as proteins, carbohydrates, hemoglobin, ATP, DNA or other substances. If necessary, such filtrate can be retained and subjected to analysis and testing such as for example to determine the level of organic soil. According to embodiments of the invention, both the concentrated material as well as the filtrate may be recovered and collected for testing as needed.

For example, it would be possible to concentrate the collected liquid by discarding 90% or 95% or 99% of the volume of the collected liquid, and retaining only 10% or 5% or 1% of the original volume. The retained liquid would still contain all or most of the contaminants/microorganisms that have been received from the endoscope.

In such a receiving container, there can be a displacement device such as a syringe that can urge liquid through the concentrating filter. There can be a pressurization port suitable for application of gas pressure to urge sampling fluid out through the concentrating filter. Suction can also be used to urge sampling fluid to flow through the concentrating filter. Although a source of pressure or suction is contemplated as the driving force for forcing liquid through the filter, it is also possible that the liquid can pass through the concentrating filter 250 simply by the action of gravity. It is contemplated that even after concentrating by filtering, some liquid can remain inside receiving container 126. In this way, as receiving container 126 is shipped to a testing laboratory, the contents inside it would not be completely dry.

In FIG. 12, it is illustrated that concentrating filter 250 can be located near the bottom of receiving container 126. However, other locations for concentrating filter 250 can be used. In FIG. 12 it is illustrated that a bottom closure cap 260 closes an exit path downstream of concentrating filter 250. However, other arrangements can be used.

FIG. 13 shows that a receiving container can contain a plurality of subcompartments 126A-D. Each subcompartment 126A-D can receive sampling fluid from a particular channel (or subset of channels) of the endoscope that is being sampled. The contamination status of each channel (or subset of channels) can be determined by biological testing of the contents of each subcompartment individually. This would permit identification of which endoscope channel (or subset of channels) is the source of contamination. For such purpose, appropriate tubing connections would have to be provided. Tubing connections can be designed, for example, so that there is only one correct or geometrically possible way of connecting the various pieces of tubing to various ports on the receiving container.

Referring now to FIGS. 14-18, with the use of some of the apparatus and methods described herein, it is possible to test all internal passageways of an endoscope by passing a sampling fluid through all of the internal passageways, and optionally also testing external features of the endoscope tip that can harbor pathogens or other foreign matter, by impinging a sampling fluid onto the external features. In such situations, the resulting volume of recovered liquid can be fairly large. Thus, the collected pathogens or foreign matter can be at a low concentration in the recovered sampling fluid.

Figure 14:
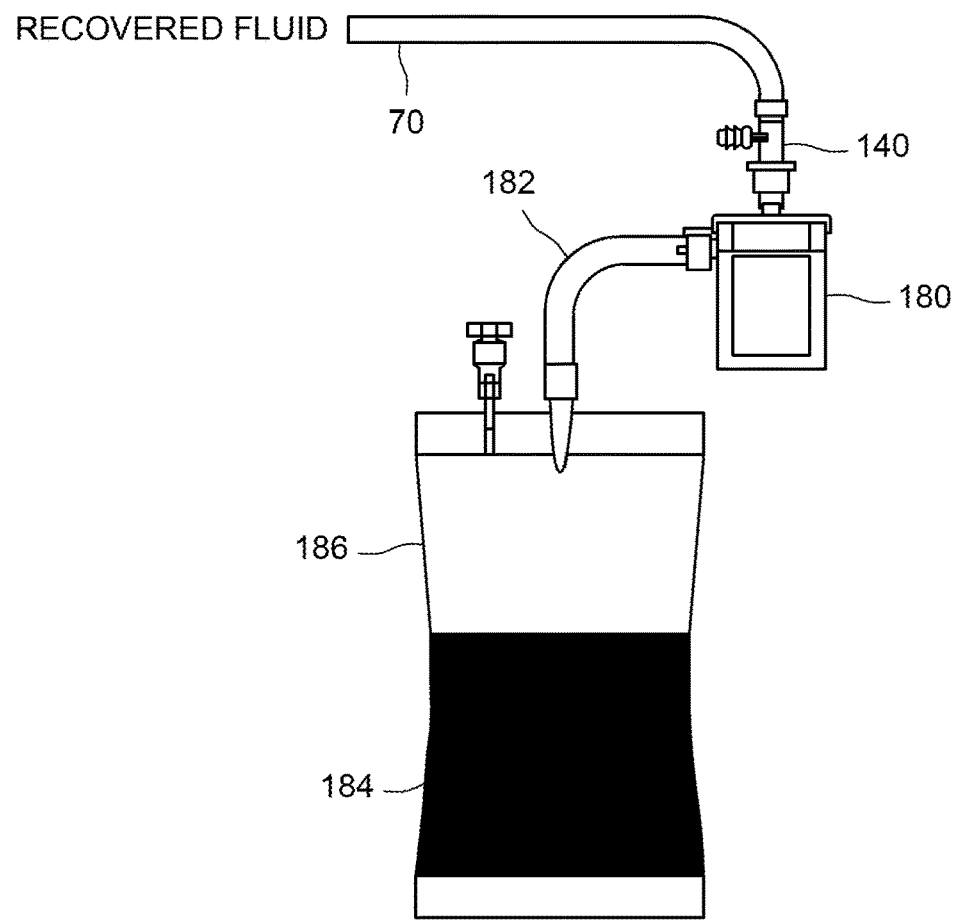
FIG. 14 is a lateral view of a portion of the third embodiment of the fluid handling portion of an endoscope test apparatus, modified to include a sample concentrator.

In FIG. 14, a portion of the fluid handling portion 54 of an endoscope test apparatus 50, as illustrated in FIG. 10, is modified to include a sample concentrator 180.

Sample fluid returned from endoscope connectivity portion 52 through sample collection tube 70 may pass through brush cut-off tube 140 (although the presence of a brush cut-off tube is optional) and may enter sample concentrator 180, wherein the sample fluid may be filtered so as to retain any pathogens and/or foreign matter. Liquid 184 that passes through the filter may then pass through concentrator overflow tube 182 into container 186.

Figure 15:
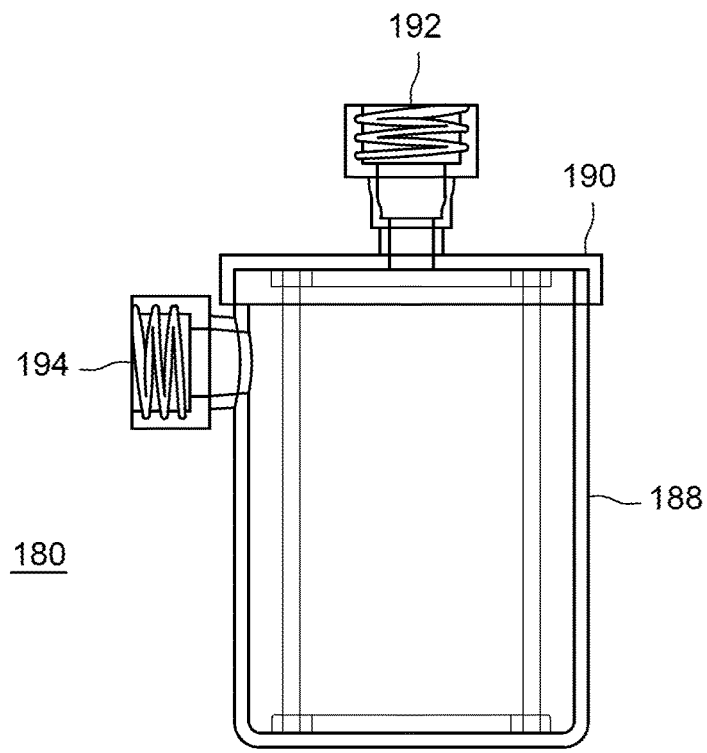
FIG. 15 is a lateral view of the sample concentrator of FIG. 14.
Figure 16:
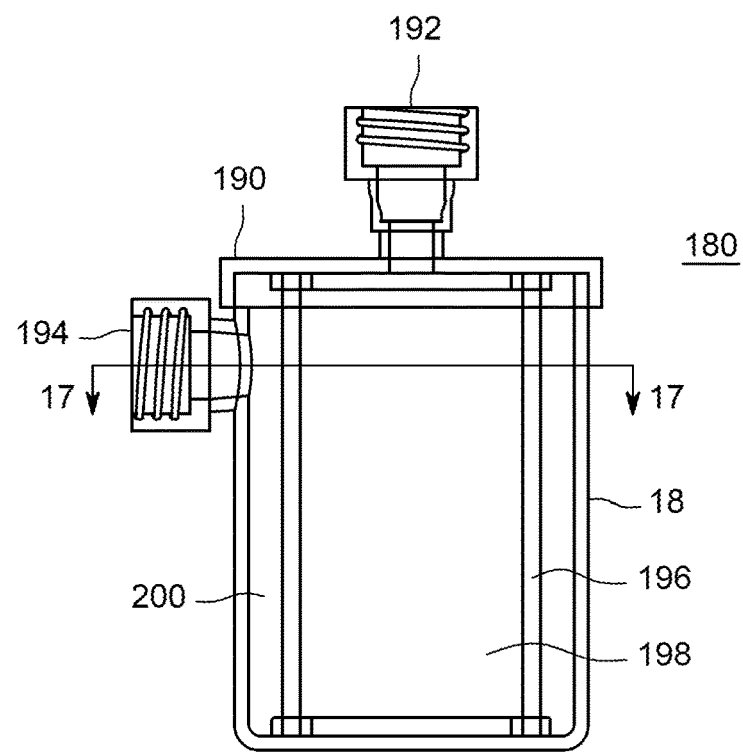
FIG. 16 is a lateral cross section view of the sample concentrator of FIG. 15.
Figure 17:
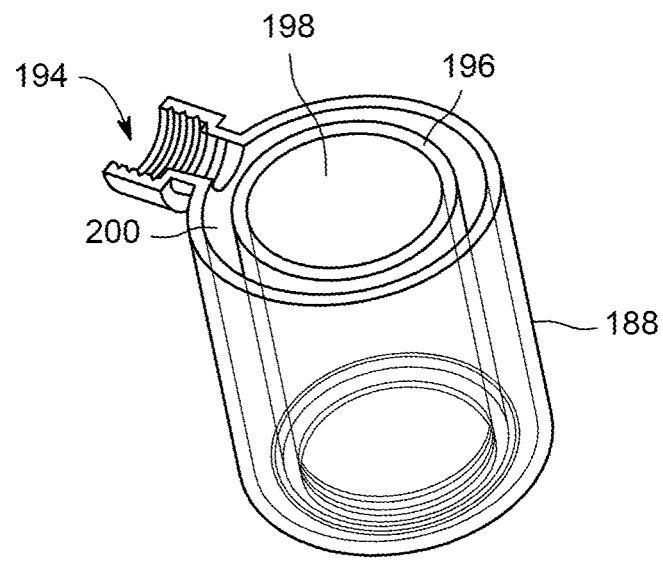
FIG. 17 is an oblique top cross-sectional view of the sample concentrator of FIG. 14.

Referring to FIGS. 15-17, sample concentrator 180 can comprise a sample concentrator bottom 188, generally in the form of an open top cylindrical container, and a sample concentrator top 190, generally in the form of a flat circular lid. A concentrator filter 196, generally in the form of a hollow cylinder, can be disposed within sample concentrator bottom 188, between the inner bottom surface of sample concentrator bottom 188, and the underside surface of sample concentrator top 190. Thus disposed concentrator filter 196 can divide the interior volume of sample concentrator 180 into a concentrator inner chamber 198, comprising the interior volume of sample concentrator 180, within the confines of concentrator filter 196, and a concentrator outer chamber 200, comprising the portion of the interior volume of sample concentrator 180 outside of concentrator filter 196.

A primary input port 192 can connect through sample concentrator top 190 with concentrator inner chamber 198, and concentrator outlet port 194 can connect through the sidewall of sample concentrator bottom 188, proximal the open top edge of sample concentrator bottom 188, to concentrator outer chamber 200.

The material and construction of concentrator filter 196 can be chosen such that concentrator filter 196 permits the relatively free passage of the liquid portion of the sample fluid, while retaining any pathogens and/or foreign matter.

The dimensions of sample concentrator 180 can be chosen such that the depth of sample concentrator bottom 188 is sufficient to receive any brush tip samples if such are produced during the test procedure, and such that the liquid volume within the sample concentrator, up to the level of concentrator outlet port 194 amounts to the desired final sample size.

During the endoscope test procedure, the entirety of the sample fluid returned through sample collection tube 70, may be passed through primary input port 192, into a concentrator inner chamber 198, from which the majority of the fluid portion of the sample fluid passes through concentrator filter 196 into concentrator outer chamber 200, and then through concentrator outlet port 194 to filtered sample container 186. Substantially all pathogens and/or foreign matter may remain within concentrator inner chamber 198.

As with any embodiment with a concentrator, at completion of the test procedure, sample concentrator 180 can be disconnected from the remainder of the test apparatus, and primary input port 192 and concentrator outlet port 194 can be capped. The sealed sample concentrator 180, containing a small portion of sample fluid, substantially all pathogens and/or foreign matter collected during the test procedure, and any brush tip samples, can then be sent to an appropriate testing facility for analysis. Indeed, this process can be done with a receiving container 126 lacking a concentrator.

While FIG. 14 illustrates the inclusion of a sample concentration device in an endoscope test apparatus that utilizes a single-phase sampling fluid, another embodiment of sample concentrator 180 can be provided for an endoscope test apparatus that utilizes a two-phase sampling fluid.

Figure 18:
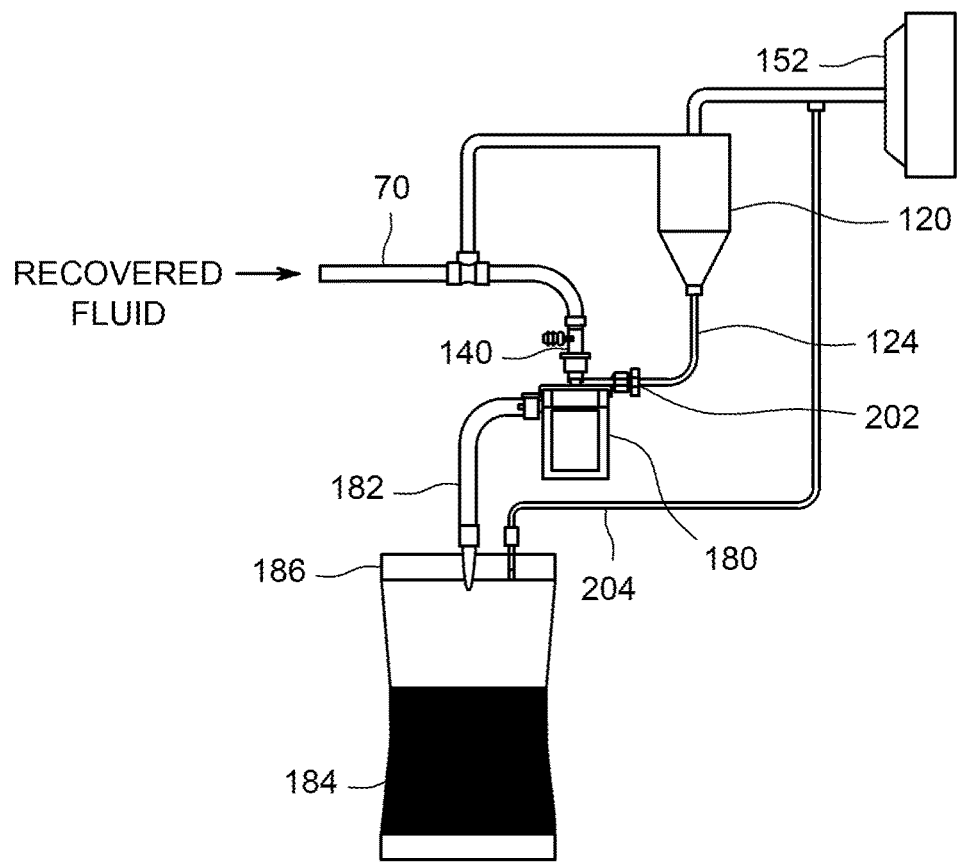
FIG. 18 is a lateral view of a portion of the second embodiment of a fluid handling portion of an endoscope test apparatus, modified to include a sample concentrator.

FIG. 18 depicts a portion of the fluid handling portion 54 of a endoscope test apparatus 50, as illustrated in FIG. 9, modified to include a second embodiment of sample concentrator 180, in which the second embodiment of sample concentrator 180 has a secondary input port 202. The secondary input port 202 can be conjoined to primary input port 192, or independently connected to concentrator inner chamber 198 of sample concentrator 180.

In FIG. 18, two-phase sample fluid returned from endoscope connectivity portion 52 enters separator 120, where the liquid portion of the two-phase fluid is separated from the air. The air can be exhausted through air discharge filter 152, and recovered liquid drained from separator 120 through sample tube 124, through secondary input port 202, into concentrator inner chamber 198 of sample concentrator 180.

As in the previous description of the operation of sample concentrator 180, substantially all of the liquid portion of the sampling fluid utilized during the endoscope testing procedure, including substantially all pathogens and/or foreign matter dislodged from the endoscope during the test procedure, and any brush tip samples generated during the test procedure, can enter concentrator inner chamber 198 of sample concentrator 180. A majority of the sample liquid entering concentrator inner chamber 198 of sample concentrator 180 can flow through concentrator filter 196, into concentrator outer chamber 200, then out through concentrator outlet port 194.

Filtered sample liquid 184, from concentrator outlet port 194 can be collected in filtered sample container 186. A filtered sample vent tube 204 can connect filtered sample container 186 to air discharge filter 152, to allow equalization of pressure within this portion of the apparatus.

Figure 19:
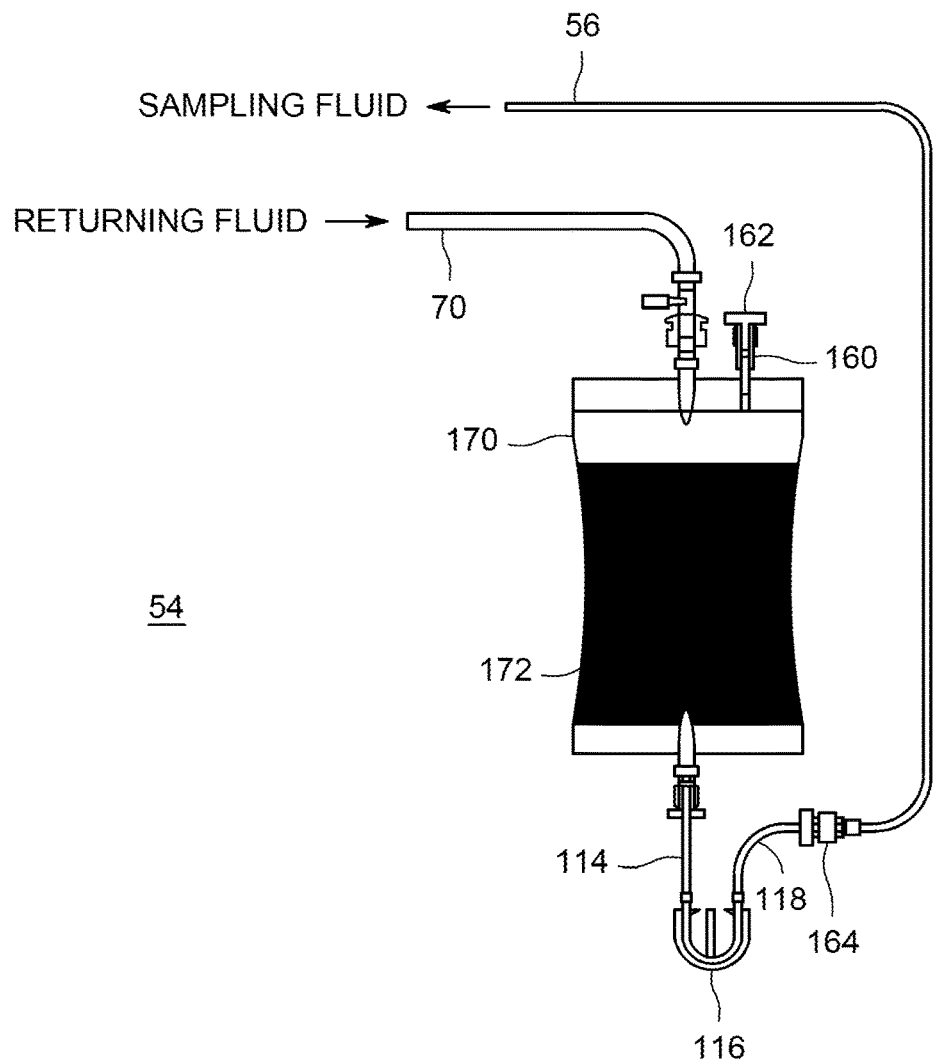
FIG. 19 is a lateral cross-sectional view of a fifth embodiment of a fluid handling portion of an endoscope test apparatus.
Figure 20:
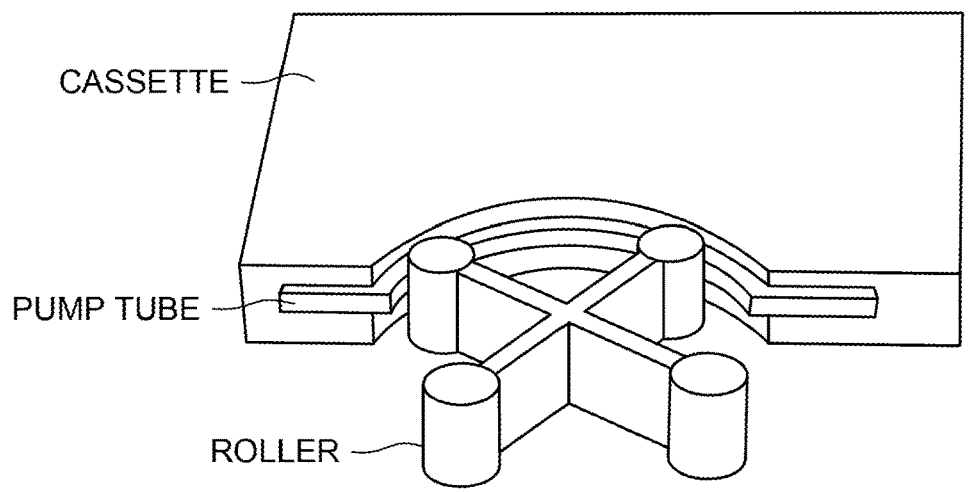
FIG. 20 shows a pump tube of a peristaltic pump contained in a cartridge.
Figure 21:
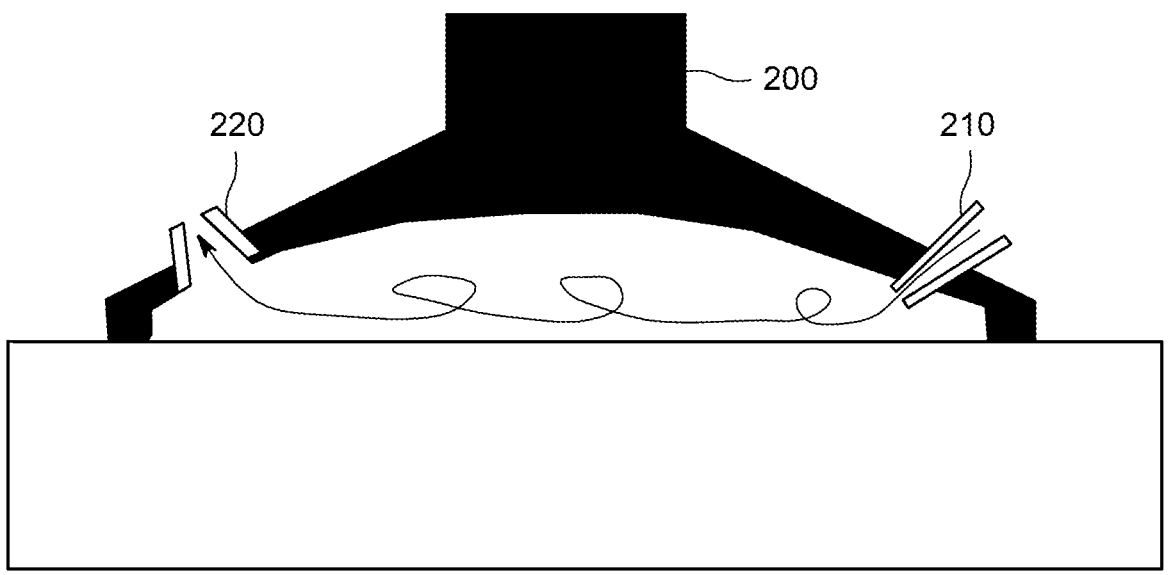
FIG. 21 shows a type of sampling device or connector or interface for a surface that is flat or nearly flat.

A fifth exemplary embodiment of a fluid handling portion 54 of an endoscope test apparatus 50 is illustrated in FIG. 19. In this embodiment, the sampling liquid can be a single-phase liquid only, and liquid pump 116 can move test solution 172 from test solution container 170, through metering pump input tube 114, and through metering pump output tube 118 to distribution tube 56 of endoscope connectivity portion 52 of endoscope test apparatus 50. In this embodiment of the invention, the liquid is circulated through the endoscope multiple times, but in between passes of the liquid the liquid is filtered through filter or concentrator 180 so as to remove the contaminants from the liquid and concentrate them. The filtration can be performed with a filter as illustrated in any of FIGS. 14-17.

Automated System

Automation can also include scheduling intervals of flow, such as two-phase flow, either before or after or both before and after brushing, for any desired duration.

Figure 24:
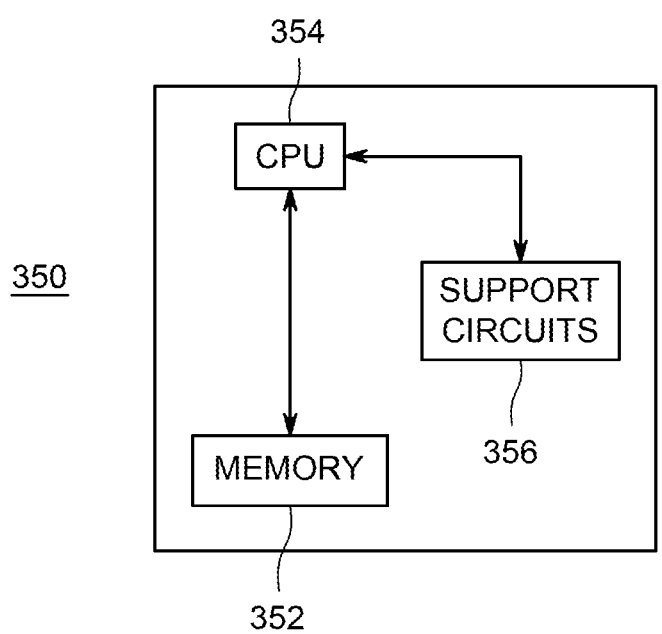
FIG. 24 illustrates a controller that can be used with the system of the invention.

The system can contain a controller 350 (FIG. 24), which comprises a central processing unit (CPU) 354, a memory 352, and support circuits 356 for the CPU 354 and is coupled to and controls the various elements of the immunization testing device or, alternatively, operates to do so in conjunction with computers (or controllers) connected to the immunization testing device. For example, another electronic device can supply software, or operations may be calculated off-sight with controller 350 coordinating off-sight operations with the local environment. The controller 350 may be one of any form of general-purpose computer processor that can be used for controlling various devices and sub-processors. The memory, or computer-readable medium, 352 of the CPU 354 may be one or more of readily available memory such as random access memory (RAM), read only memory (ROM), flash memory, floppy disk, hard disk, or any other form of digital storage, local or remote. The support circuits 356 are coupled to the CPU 354 for supporting the processor in a conventional manner. These circuits can include cache, power supplies, clock circuits, input/output circuitry and subsystems, and the like. Methods of operating the immunization testing device may be stored in the memory 352 as software routine that may be executed or invoked to control the operation of the system. The software routine may also be stored and/or executed by a second CPU (not shown) that is remotely located from the hardware being controlled by the CPU 354. While the above discussion may speak of the "controller" taking certain actions, it will be recognized that it may take such action in conjunction with connected devices.

In certain embodiments, the controller is a smart phone, tablet, PC or the like that connects to the analytical module by wire connections or wirelessly.

In certain embodiments certain of the logic circuits or algorithms may be distantly external, such as in Canada. In such embodiments the "controller" is made up of the electronic elements at or near the point-of-care that coordinate data going to such distant logic circuits and operative instructions derived from such distant logic circuits.

Data concerning pressure, flow-rate, liquid levels, optical signals of contamination, or the like can be fed into the controller. The controller can use the data to operate valves or pumps as appropriate given the status data.

Depending on what is desired, flow can be delivered to only one channel of the endoscope at a given time, or to all of the channels of the endoscope simultaneously, or to a subset of the channels of the endoscope at a given time. Such choice can be made using a manually operated system, such as by manually operated valves. Such choice can be made by an automated control system, which can be controlled by a microprocessor. If an automated control system is used, it can also incorporate programmed time durations of certain steps of the procedure. With an automated control system, operation of the system can be responsive to parameters such as pressure (which can be measured during operation).

Formulation of Sampling Liquid

It can be understood here that the term sampling liquid refers to liquid used for sampling an endoscope for the presence of contaminants, microorganisms etc., or for recovering those contaminants, microorganisms etc. In general, in embodiments of the invention, the sampling liquid that is passed through the endoscope can serve the purpose of collecting organisms, biofilms, organic soil and other contaminants that can be present in the endoscope. This can be done for purposes of assessing the presence of such organisms and contaminants in the endoscope.

Accordingly, to provide an accurate test result or representation of the condition of the endoscope, survival of such organisms is desirable and should not be materially compromised. In this described situation, any system component or chemical ingredient that kills a living organism, or in some embodiments inactivates viruses, during the collection or recovery procedure can result in false confidence in the cleanliness of the endoscope. This goal of keeping organisms alive and viable for testing (for example by culture methods) is in contrast to the situation in conventional endoscope cleaning procedures, in which it is acceptable and even desirable that the liquid be a composition that is hostile to living organisms.

Accordingly, in embodiments of the invention, the sampling liquid can have a number of properties that are either benign or favorable to the existence of microorganisms.

First of all, the sampling liquid can be prepared so as to be sterile. Initial sterility by itself does not affect the life of organisms that could be present in the endoscope, but initial sterility is important for assuring that the test results indicating contamination do indeed represent the presence of contamination that existed in the endoscope.

Additionally, the sampling liquid can be chosen to be non-toxic in its chemical composition, so as not to kill, inactivate or damage organisms that may be present.

Another property of the sampling liquid is its pH. The pH of the sampling liquid can be chosen to be in a range that is typical of physiological conditions, such as a pH range of from 6 to 7.5, and preferably about 7. This assures that if microorganisms are present, they will be just as likely to survive as the microorganisms are likely to survive in normal life, i.e., by being in conditions that are typical of the human body and living species.

Another relevant property of the sampling liquid is its osmolarity. For example, if the sampling liquid were pure water interacting with cells, there would be a tendency for water to diffuse into the cells, possibly causing the cells to swell and burst. In the other extreme, a sampling liquid that is highly osmotic could pull water out of the cells or dehydrate organisms by osmosis, which also could damage the cells or organisms. Accordingly, the sampling liquid can be chosen to be approximately isotonic or iso-osmolar. For example, the liquid may be chosen to have an osmotic pressure of about 260-320 mOsm/kg. For example, the sampling liquid can be physiological saline, or phosphate buffered saline, or equivalent. Other ingredients could also be present. In an embodiment of the invention, there can be provided a sampling liquid that has an oncotic pressure that is the same as, or nearly the same as, the oncotic pressure of human tissue and bodily fluids. A common buffer is Tris, or tris(hydroxymethyl)aminomethane, also known as tromethamine or THAM, an organic compound with the formula $(HOCH_2)_3CNH_2$.

Although it can be preferable for the sampling liquid to have a pH and osmolarity that approximate physiological conditions, in some embodiments this does not have to be done. In fact, it can even be possible to use a sampling liquid as simple as sterile pure water, such as water that has been prepared by Reverse Osmosis, if the time between sampling and culturing is short such as about an hour or less. Such water would not have the most appropriate osmolarity, but if it can be arranged that testing of the recovered liquid is performed soon after the endoscope sampling procedure, it can be acceptable to use sterile pure water. The use of the sterile reverse osmosis (SRO) water or equivalent sterile liquid such as sterile saline or buffer is preferred if the endoscope is to be used to treat patients. In other words, when the endoscope is high-level disinfected and such disinfected conditions need to be maintained, the use of SRO water or sterile saline or sterile buffer as the sampling fluid may be appropriate or desirable.

The sampling liquid can be chosen to avoid of material amounts of any additives that would compromise the viability of recovered organisms or would denature protein or hemoglobin. While there may be some denaturation or loss of viability, so long as the virus measurement is not materially impaired, and so long as protein substantially retains structure and is not lost from recovery due to denaturation, these requirements are met.

Another relevant property is the possible presence of surfactants or solvents. First of all, it is possible that the sampling liquid can be provided containing no surfactant. Alternatively, surfactants can be present as an aid to removing, detaching or dislodging organisms or biofilms for the purpose of detecting their presence. There are many known surfactants, but only a small subset of known surfactants is favored for the present recovery and sampling purposes. Most surfactants can damage the walls and membranes of cells, and even the envelope membrane of enveloped viruses. Some other surfactants are known to be biocidal, such as cationic quaternary ammonium salts known as "quats," for example. For the present purpose, surfactant and the amount thereof can be chosen so as not to damage the membranes or walls of cells or viruses so that the presence of such surfactants does not compromise the quantitation of organisms by culture methods for example. A suitable surfactant should not denature or compromise the viability of non-enveloped viruses that are of concern. A suitable surfactant can be a non-leathal or non-inactivating to bacterial species of concern, which can be defined as not killing more than about 2% of an inoculum. A surfactant can be chosen so as to not denature proteins of concern. An appropriate surfactant is one that has a Hydrophilic-Lipophilic Balance of 14 or greater (such as 15 to 20). Surfactants can be tested for biocidal activity, to avoid surfactants that have biocidal activity. An example of a suitable surfactant is the Tween family of surfactants, including Tween 80 and Tween 20. Tween 20 (also known as polysorbate 20) is $(C_{26}H_{50}O_{10})$ (2-[2-[3,4-bis(2-hydroxyethoxy)oxolan-2-yl]-2-(2-hydroxyethoxy)ethoxy]ethyl dodecanoate) (polyoxyethylene sorbitan monolaurate). Tween 80 is $(C_{32}H_{60}O_{10})$ (2-[2-[3,4-bis (2-hydroxyethoxy)oxolan-2-yl]-2-(2-hydroxyethoxy) ethoxy]ethyl octadec-9-enoate) or (2-{2-[3,4-bis(2-hydroxyethoxy)oxolan-2-YL]-2-(2-hydroxyethoxy) ethoxy}ethyl octadec-9-enoate). There are also suitable surfactants that belong to other families such as Pluronic® and others that have similar properties to Tween 80 that can be included in the sampling and recovery liquid according to the present invention. Pluronic is a Poly(Oxyethylene)-Poly (Oxypropylene)-Poly(Oxyethylene) Triblock Copolymer. The sampling liquid can be formulated to have a high wettability, which can be quantified as having a surface contact angle, with a solid surface, of less than 20 degrees. This can help to avoid injuring cells that are potentially alive. Contact angle can be measured for example with at [can we recite an instrument?].

Inclusion of surfactants in the sampling liquid, such as in the two-phase mixture, can improve the recovery rates of contaminants and residues from the channel wall. Surfactant can facilitate wetting between the liquid fraction of the two phase flow and the surface of the passageway. In additions the surfactant can increase liquid-gas interfacial surface area which can also increase the extraction/recovery of on the contaminants. As it is known in the art, surfactants can simultaneously decrease the adhesion forces between contaminants and channel walls, and thereby facilitate the recovery of adhering contaminants. Therefore, two-phase flow can also be made with surfactant solutions and this may be beneficial in the recovery of contaminants from passageways.

"Essentially free of surfactant" means that any surfactant present is not enough to materially affect surface tension.

Examples of endoscope sampling solutions include the following:

TABLE 1A

Sterile distilled water or sterile reverse osmosis (SRO) water;
Saline solution [NaCl (0.9%)];
A mixture comprising Peptone (0.01%), Tween 80 (0.1%), NaCl (0.043%), Phosphate (0.095%), balance water;
A mixture comprising Peptone (0.01%), Tween 80 (0.3%), Lecithin (0.01%), Histidin chlorhydrate (0.01%), NaCl (0.043%), KH2PO4 (0.036%), Na2HPO4, 2H2O (0.072%), balance water;
A mixture comprising Tween 80 (0.3%), Lecithin (0.03%), L-Histidin (0.01%), Sodium thiosulfate (0.05%), balance water.

Table 1B further provides some examples of sampling liquids

TABLE 1B

|  | SRO water | Pineau Neutralizer (PN) | Tween 20 Soln | Tween 20 Soln and Silica | Tween 20 Soln, Silica, and PN |
|---|---|---|---|---|---|
| sRO water | X |  |  |  |  |
| 1X PBS |  |  | X | X | X |
| Tween 20 |  |  | X, 0.075% | X, 0.075% | X, 0.075% |
| Silica |  |  |  | X, 1% | X, 1% |
| Pineau Neutralizer |  | X |  |  | X |

Some of the above formulations contain neutralizers. Lecithin and Histidin chlorhydrate are neutralizers for aldehydes. Lecithin, L-histidin and sodium thiosulfate are neutralilzers for peracids. Pineau neutralizer is described in Pineau et al., Evaluation of endoscope cleanliness after reprocessing: a clinical-use study, Central Service 2013; 1:22-27 (incorporated herein in its entirety (description: Lecithin 3 grams; Sodium thiosulfate 5 grams; L-Histidine 1 gram; Tween 80 30 mL (heated); sRO water (heated) in QS to 500 mL). Pineau neutralizer is believed to neutralize aldehydes. Neutralizers are further discussed in Sheraba N S, Yassin A S, Fahmy A, Amin M A (2012), Efficacy and toxicity of neutralizers against disinfectants and antiseptics used in vaccine production facility. Afr. J. Microbiol. Res. 6(36):6565-6571, the contents of which are incorporated herein in their entirety.

In embodiments of the invention, the sampling liquid can contain a neutralizer that neutralizes any high-level disinfectant that could remain inside or on the endoscope from a previous reprocessing. The inclusion of neutralizers can be useful for the goal of preserving the viability of organisms that may have survived high-level disinfection after reprocessing, so that such organisms can be detected during biological testing of recovered liquid such as by accepted culture methods. Such use of neutralizer could avoid having a "false negative" result. It is noted that the use of neutralizers in the sampling liquid is not the only possible place where neutralizers could be used. It is possible that the use of a neutralizer in the sampling liquid could require a rinse to remove possible leftover neutralizer, so as to avoid possible exposure of the next patient to neutralizer substance that might remain in the device. Such rinse might add an extra step to a protocol. Alternatively, it is possible that a quantity of a neutralizer substance could be provided in the receiving container. In this way, collected liquid would be protected from the effect of possible leftover high-level disinfectant collected by the sampling process, and yet it would not be necessary to perform a rinse step on the endoscope.

Yet another consideration is that sometimes polymers that are used to make medical systems such as tubing and connectors contain extractives, which are substances such as plasticizers, mold release agents or other substances that can leach out of the plastic into liquid that contacts the plastic. Such substances can be injurious to cells. For purposes of detecting organisms and contaminants, it is undesirable to have any material presence in the liquid of substances that can be injurious to cells. Therefore, components of the sampling and recovery system such as tubing and vessels can be chosen to be free or substantially free of extractable and compounds that are injurious to cells. Extractable is measured with respect to the sampling liquid. Relevant system components according to the present invention include tubing, connectors, bags, containers and other parts of the recovery kit as described elsewhere herein.

The described lack of material amounts of germ-killing leachables or organism inactivating compounds in the entire recovery kit refers to the condition of the kit material after undergoing sterilization. Maintaining the starting material free of germ-killing leachables is a first step, but it is not necessarily sufficient. Sterilization by Ethylene Oxide or steam is unlikely to change the nature of the leachables. However, it is possible that a sterilization method such as gamma irradiation or electron beam exposure could create undesirable compounds that might not have been present in the original material. The same consideration is applicable to the sampling liquid, which also typically undergoes a sterilization process. An embodiment of the invention relates to a sterile kit constructed from materials that do not materially leach compounds that can kill or inactivate recovered organism or compromise or affect the test results, even after undergoing sterilization.

Pump and Cassette Design

In embodiments of the invention, a peristaltic pump can be used to introduce liquid from the sterile reservoir into the endoscope region of the system. Peristaltic pumps are commonly used to pump small to moderate volumes of liquids and slurries against low to moderate pressure differentials. A one-time-use cassette can be provided containing some of the components of the fluid handling system in a unitary assembly. The cassette can contain an interface by which the one-time-use tubing component interfaces with the pump head of a peristaltic pump.

If the cassette has an overall proportion that can be described as a flat block, the pumptube can be mounted on one of the edges, such as one of the thinner edges, of the block. The edge can be substantially solid or at least rigid. A portion of the edge can be concave in shape, and more specifically can be a portion of a circular arc, with the pumptube being supported against this arc.

Liquid-only with Recirculation and/or with Concentration

The system of the fourth exemplary embodiment and FIG. 11 involved recirculating the liquid through the endoscope a number of times. In such a system, in the process of performing sampling, the system could spread contamination from one channel of the endoscope to other channels of the endoscope.

Accordingly, yet another embodiment of the invention is also possible. With reference now to FIG. 19, using a concentrating filter such as was illustrated in FIGS. 15-17, there can be provided a system in which such a concentrating filter is used in conjunction with a liquid-only system such as the system of the fourth embodiment that was illustrated in FIG. 11.

In the system of FIG. 19, liquid exiting the endoscope has to pass through the concentrating filter before it returns to the endoscope and flows again in another pass through the endoscope. Liquid that has passed through the concentrating filter would no longer contain biological contaminants, and so that liquid can return to the endoscope without spreading contamination to other parts of the endoscope. At the same time, there is still the benefit of passing the liquid through the endoscope multiple times, in terms of recovering more contaminants per unit of liquid used, and of reducing the total amount of liquid that must be used. Thus, the concentrating filter serves the purpose of concentrating contaminants for use during biological testing and also serves the purpose that liquid sent back to the endoscope for a subsequent pass through the endoscope is free of contaminants.

As with any of the disclosed concentrators, the concentrating filter can be a flat sheet membrane, or a hollow fiber membrane, or a tubular membrane or other configuration. The pore size of the concentrating filter can be in the range from 1 nanometer to 0.45 microns. The sample can be concentrated for example by a factor of anywhere from 10 to 10,000. The latter high concentration might be used for PCR (Polymerase Chain Reaction) or DNA analysis, and would avoid the downstream laboratory needing to further concentrate. ATP or culturing or PCR methods and techniques can be used to analyze the recovered contaminants and to identify the bacterial or virus species recovered from the endoscope or similar devices.

Enclosure for Sampling External Surface

Referring now to FIG. 21, in an embodiment of the invention, there is illustrated an enclosure apparatus 200 that is capable of conforming to or engaging with an external surface of a device being tested. This may be used so as to direct the extraction or sampling of such a surface with the two-phase flow mixture. As illustrated, the surface is a flat surface, but other shapes are also possible, possibly uniquely suited to a particular object being sampled. The enclosure apparatus 200 may include a nozzle 210 that is directed at the surface being tested, and may include a receiving duct 220 that may be shaped and located so as to receive flow that has contacted the surface after leaving the nozzle 210, i.e., the receiving duct 220 may be generally downstream of the nozzle 210. The apparatus may be soft or flexible in order to better conform to the surface of interest. Such a device may perform a similar function to the connector illustrated in FIG. 5, but for a different geometry or shape of tested surface.

It is possible to inject a two-phase flow. It is also possible to deliver the liquid to the surface with spray nozzles and the air can be injected such that residues present on the entire surface can be recovered and collected for subsequent analysis. In order to ensure sampling/recovering the entire surface, the flow can be can be applied in each of two opposite directions, and the confinement can be designed so as prevent shadowing effects.

Additional Devices for Sampling

Among the devices beyond endoscopes that can be sampled, either in internal lumens or on exterior surfaces, are without limitation Biopsy Forceps, Lumen Catheters, Trocars, Laparoscopic Devices, Surgical Robotic Arms, Reusable Lumen Surgical Devices, Surgical Suction devices, Arthroscopic Shavers, Light pipes, Insertion Devices, Tubing, and the like.

Addition of Solid Particles

In embodiments of the invention, the sampling liquid can contain solid particles. Such solid particles may be especially useful for abrading and therefore sampling biofilm that has greater mechanical strength than traditional (ordinary, e.g., Type I) biofilm. Such particles may be materially non-adsorbing with respect to contaminants of interest. It is believed that a hardness greater than 2 on the Mohs hardness scale is sufficient to abrade biofilm, even built-up biofilm. Accordingly, the solid particles may be chosen to have a hardness of greater than 2, or greater than 3, or greater than 4 on the Mohs hardness scale. Silica is an example of a suitable material. The silica that is used may be hydrophilic silica or other particles with very low capacity to adsorb organic residues.

Exemplary particles include:

| Product Description | Manufacturer |
|---|---|
| Wool CMW80<br>Dia.: 20-30 μm (>90%)<br>Length: Max: 200 μm (>95%) | Goonvean Fibres<br>(goonveanfibres.com) |
| Nylon (Polyamide) Fibre WN60<br>Dia.: 10-20 μm ± 10% (>95%)<br>Length: Max: 250 μm (>90%)<br>(Average (>50%): ~125-250 μm | Goonvean Fibres<br>(goonveanfibres.com) |
| Viscose Fibre RM60<br>Dia.: 8-25 μm ± 10% (>95%)<br>Length: Max: 250 μm (>95%)<br>(Average (>50%): ~100-225 μm | Goonvean Fibres<br>(goonveanfibres.com) |
| Olive Stone Grit EFOG<br>Max: 355 μm (>99%)<br>Passing: 200 μm (<15%)<br>Passing: 150 μm (<4%) | Goonvean Fibres<br>(goonveanfibres.com) |
| Silica Syloid EXF 150 (150 μm) | W. R. Grace Co., Columbia, MD |
| Silica Syloid EXF 350 (350 μm) | W. R. Grace Co., Columbia, MD |
| Silica Syloid EXF 500 (500 μm) | W. R. Grace Co., Columbia, MD |
| Hydrocarb 60-FL 78% 3996200 | Omya Inc., Cincinnati, OH |
| Hydrocarb PG3-FL 73% | Omya Inc., Cincinnati, OH |
| Omya Syncarb S160-HV<br>20% 4430400 | Omya Inc., Cincinnati, OH |
| Omya Syncarb S240-HV 20% | Omya Inc., Cincinnati, OH |
| Silica Gel, 200-425 mesh | Sigma-Aldrich, Inc., St. Louis, MO |
| Silica Gel, 28-200 mesh | Sigma-Aldrich, Inc., St. Louis, MO |
| Calcium Carbonate | Sigma-Aldrich, Inc., St. Louis, MO |

Further Embodiments and Parameters Automation of the sampling system, as described herein, can significantly decrease the time required to perform a sterility assessment, and increase the convenience to the user. Furthermore, the process of sterility assessment can be more reliable due to the repeatability of the automated technique and the elimination of possible variations of technique from one endoscope to the next or from one cleaning technician to another or from one procedure to another. Among the parameters that can be standardized are timing, flowrate, and number of steps and sequence of steps.

Sterilization of the system/kit or of any of its components can be performed by any typical standard or known method of sterilization. Such methods include: gamma radiation, electron beam radiation, ethylene oxide, and steam (autoclave), or other methods including chemical means such as exposure to aldehydes or peracids.

Because all of the one-time-use components of the sampling system are pre-sterilized, sterilely packaged and configured for sterile handling of the operational components, there is virtually no chance of the sterility assessment procedure introducing any contaminants or microorganisms that were not already present in the endoscope.

In places where reference is made in this disclosure to air, it would also be possible to use generally any gas. Such gas could be or could include nitrogen, and could have compositional similarities to air. References to pumps or air sources can include compressors, blowers, and other similar devices for moving a fluid.

In places where reference is made to two-phase flow or mixed-phase flow, that is intended to include the possible presence of solid particles in the liquid. References to liquid flow are intended to include the possible presence of solid particles in the liquid.

Although the ATP test described herein can provide some useful information, it can be worthwhile to note that there are a number of categories of contamination that are not measured by testing for the presence of ATP. A test for the presence of ATP can identify the presence of bacteria, but it cannot distinguish between planktonic bacteria and bacteria that are present in biofilm. In fact, if biofilm is highly adhering, the ATP method can fail to detect the biofilm-based bacteria. Also, an ATP test does not provide any information about the species of bacteria and does not quantify the presence of bacteria. It can further be noted that a test for the presence of ATP does not reveal anything about the possible presence of viruses, nor does it detect the possible presence of prions. Also, an ATP test does not detect bioburden or organic soil.

In contrast to an ATP test, the apparatus and techniques described herein, especially if they use mixed-phase flow of gas and liquid, can better remove or sample contaminants. Furthermore, if appropriate testing is done on the material recovered using the apparatus and techniques described herein, it is possible to detect many more types of contaminants. Such testing can provide much more information about the recovered contaminants than is available simply from an ATP test. Testing of the recovered material can be performed for the purposes of culturing cells, analyzing DNA, or almost any biological measurement or assay that is desired.

In embodiments, the described components and techniques are used in combination with a flow of liquid along the length of the channel, or a flow of gas along the length of the channel, or both, including two-phase flow, either separately or simultaneously. In embodiments, the flow of both the liquid and the gas can be substantially steady with respect to time. Additional possibilities include pulsatile flow of either the liquid or the gas or both. In embodiments, the supply conditions of either liquid or gas can vary as a function of time. In embodiments, the ratio of liquid flow to gas flow can vary as a function of time. In embodiments, an air flow can be provided after the two-phase flow, for purposes of removing any remaining water drops or drying out the channel.

The liquid portion of the two-phase mixture can comprise an oxidizing agent, a reducing agent, an organic solvent or a mixture of organic liquid, an enzymatic solution, or a mixture of any of these as dictated by the type of contaminants or residues to be recovered and sampled. The pH of the solution can be adjusted as required.

The recovered sample can be analyzed by many methods including: TOC; HLPC; GC; GC-MS; LC; LC-MS; MS; TLC; spectrophotometry; spectroscopy methods as required; DNA; RNA; proteomics or their combination as can be determined by a person skilled in the art.

The number of volume changes or turnover number with the two-phase flow mixture in the enclosed device such as tubing or enclosure can be more than 10 and preferably can be more than 100 to 500. In some cases this turnover number can be more than 2000 depending on the residue and the complexity of the device to be sampled. The turnover number is the volume of air flowed during a cleaning procedure, divided by the volume of the system being sampled. The turnover number can be adjusted to recover at least 75% of residue or contaminant present, or can be increased when the percent of recovery desired is higher such as more than 90% or more than 95%.

A HEPA (High Efficiency Particulate Arresting) filter used in the system can have a cutoff pore size of 0.1 micron or smaller such as 0.01 micron.

The membrane or filter used to concentrate the sample can be of any type and can be selected so as to retain the residue or contaminant of interest. Both permeate and retentate can be used to analyze for residues and contaminants depending on the pore size or molecular weight cutoff characteristics of the membrane used in concentrating the sample.

Bioburden collected in the recovered sample can be retained on appropriate flat sheet membrane/filter and then placed on top of a suitable culture media for quantitation as it is known in microbiology methods.

Hollow fiber membrane modules may be preferred and concentrate the residue, contaminants including bioburden during the recovery process. The recovered residues can be ultimately purged and collected in a small vial as desired. The volume of the final sample can be selected based on the nature and concentration of the residue or contaminant. Sample can for example be concentrated by factor 10 to 100 or even 1000 times as desired. The final sample volume can be for example about 0.1 to 5 ml and this can decrease shipping cost to an external laboratory. The air pressure used to make the two-phase mixture can be increased depending on the device and can be 80 to 100 PSI or more if the device to be sampled is capable of containing such pressure.

Embodiments of the invention also include methods of use of the described systems and apparatus and compositions, as will be understood from the descriptions herein.

In addition to being used with endoscopes as described, embodiments of the invention can be used with suction tubes and generally with any luminal medical device. Other sampling applications, such as in manufacturing, are also possible.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

Where a sentence states that its subject is found in embodiments, or in certain embodiments, or in the like, it is applicable to any embodiment in which the subject matter can be logically applied.

Specific embodiments according to the methods of the present invention will now be described in the following examples. The examples are illustrative only, and are not intended to limit the remainder of the disclosure in any way.

EXAMPLE 1

This example describes a protocol for preparing biofilm for use in the described experiments. This protocol produces what can be called traditional biofilm ("TBF").
Preliminary Steps 1. Subculture *Enterococcus faecalis* ATCC 29212 and *Pseudomonas aeruginosa* ATCC 15442 on blood agar (BA) plates. The organisms should be 24 hours old on the day of experiment.

2. Sterilize the length or lengths of PTFE tubing required for testing, in the Steris System IE (include BI and CI). Dry thoroughly. Be sure the required lengths are sterilized no more than 7 days prior to testing.

3. Prepare ATS-2015 with 20% defibrinated sheep blood (this soil can be stored up to 2 weeks in the refrigerator).
Experimental 1. On Sunday night, make appropriate soil/bug suspension (EF and PA each at ~108 cfu/mL in ATS-2015 containing 20% sheep blood) and perform an inoculum count. Feed this suspension through the appropriate length of PTFE (pre-sterilized in the Steris System 1E) while attached to a pump. Circulate the soil at pump setting 5.8 overnight (~1.2 ml/min)—but in any case adjust the flow rate so as to maintain continuous uninterrupted circulation.

2. On Monday morning, make appropriate soil/bug suspension (EF and PA each at ~105 cfu/mL in 1:10 diluted ATS-2015 containing 20% sheep blood) and perform an inoculum count. Turn pump off and expel the soil from the PTFE length while still attached to the peristaltic pump tubing and return soil to the original container. While still attached to the pump tubing, push through (slowly) 20 mL of sterile RO water+30 mL of air using a 60 cc luer lock syringe. Detach PTFE from the pump (clean the pump tubing) and bring the PTFE under the biological safety cabinet ("BSC") inside a container. Push 30 mL of sterile RO water+30 mL of air through the PTFE into a discard container. Repeat×2. Push some air through to dry the tubing. Re-soil (EF and PA each at ~105 cfu/mL in 1:10 diluted ATS-2015 containing 20% sheep blood) and attach to the pump (using new pump tubing) and circulate at pump setting 5.8 until the following morning.

3. On Tuesday through Thursday, repeat rinsing/soiling of tubing exactly as per Monday. Soil overnight using the 105 cfu/mL soil/bug suspension until Friday morning.

4. On Friday (Day 5), rinse with sRO water exactly as per previous days. Dry and perform destructive and other testing as required.

In contrast to TBF, built-up biofilm is more robust than traditional biofilm, and is designated "BBF." Built-up biofilm was grown according to a procedure described in (Ref. "Alfa et al. (A novel polytetrafluoroethylene-channel model, which simulates low levels of culturable bacteria in buildup biofilm after repeated endoscope reprocessing. Gastrointestinal endoscopy, DOI: dx.doi.org/10.1016/j.gie.2017.05.014, in press)"), which is incorporated herein in its entirety. The protocol for growing it is similar to the protocol for growing traditional biofilm, except that at several times during the protocol for growing the biofilm, the biofilm is exposed to glutaraldehyde.

EXAMPLE 2

Figure 22A:
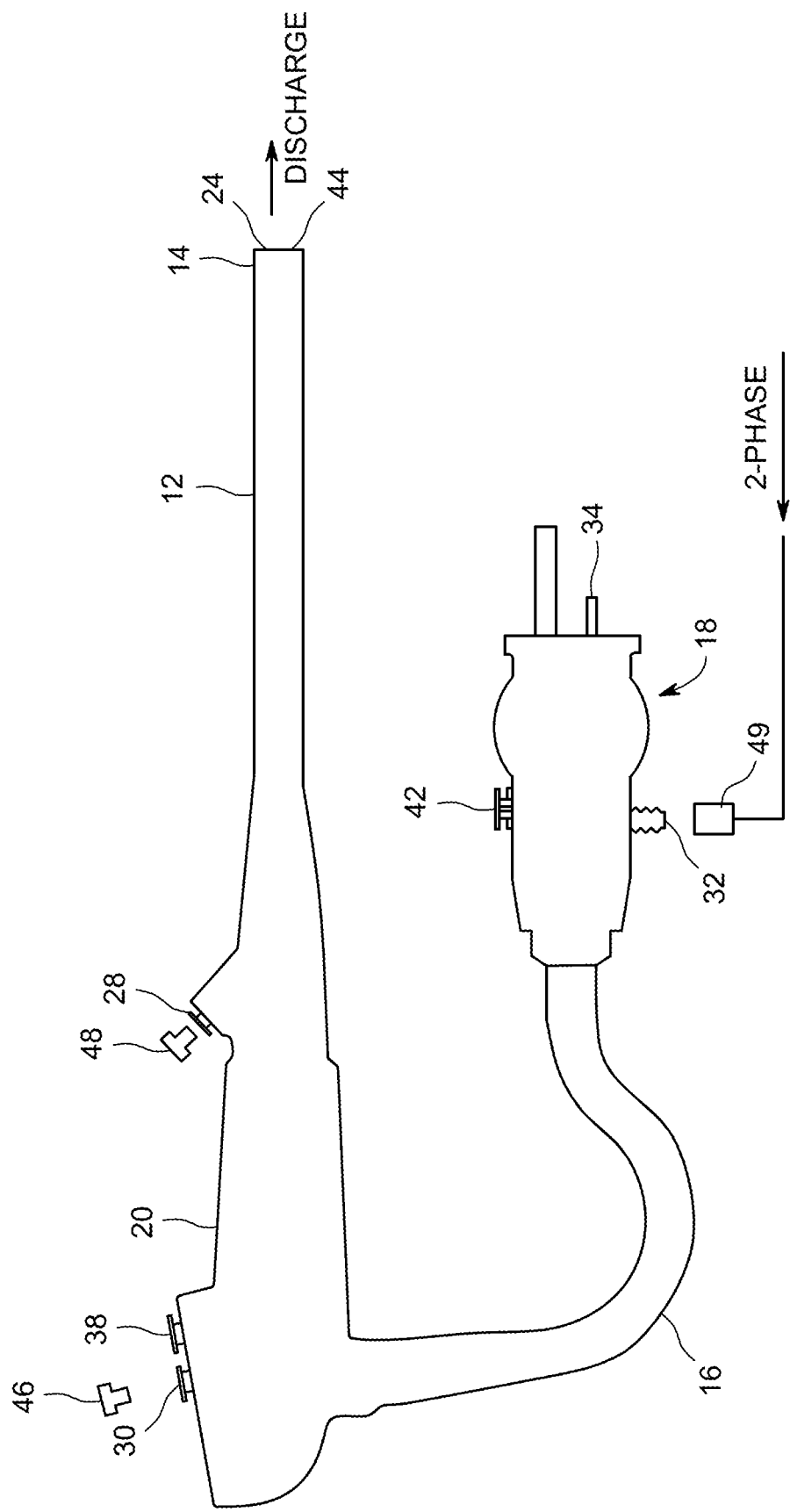
FIG. 22A shows connections to a suction channel of an endoscope for performing sampling (2-phase at e.g. 28 psi or less).
Figure 22B:
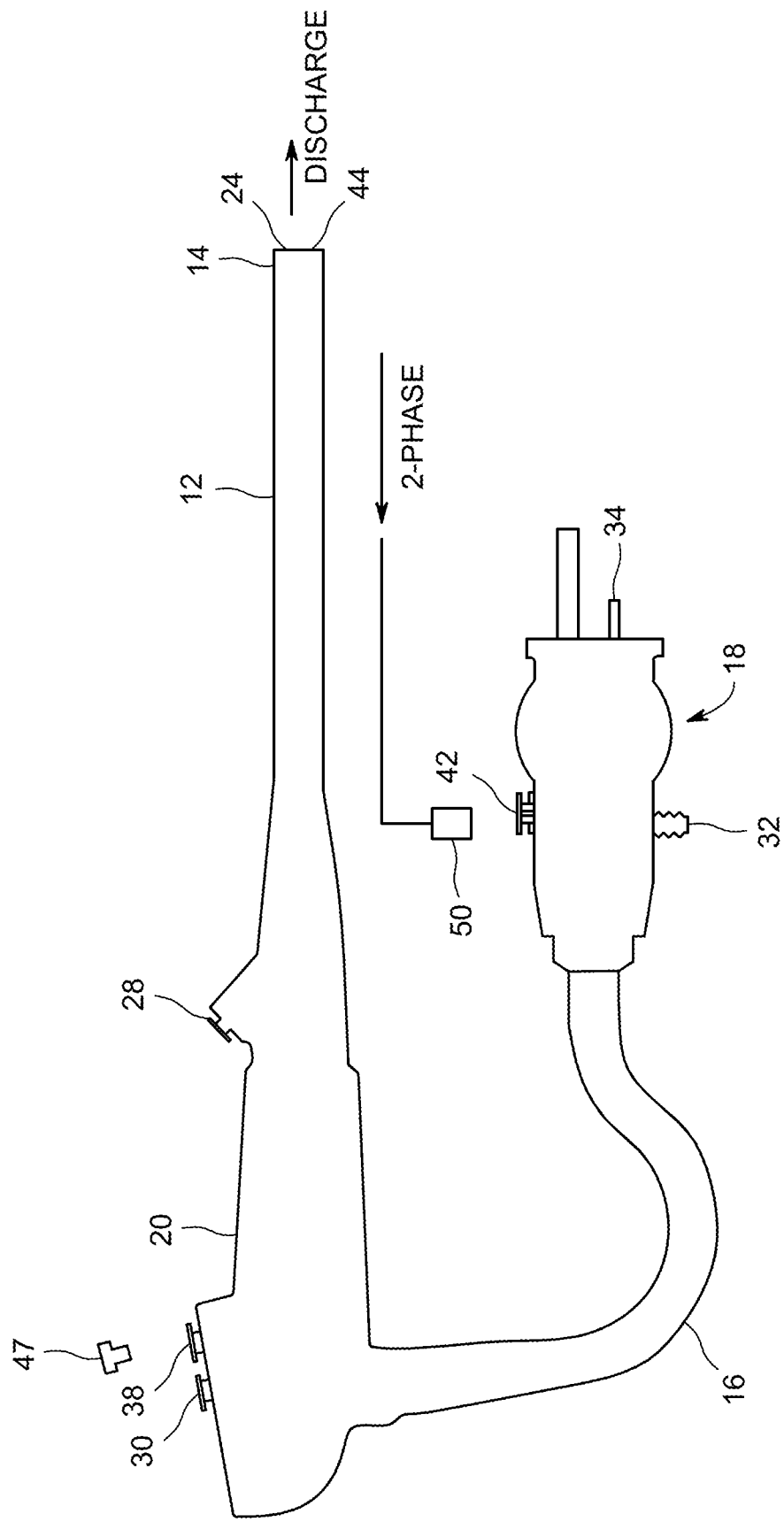
FIG. 22B shows connections to a water channel of an endoscope for performing sampling.
Figure 22C:
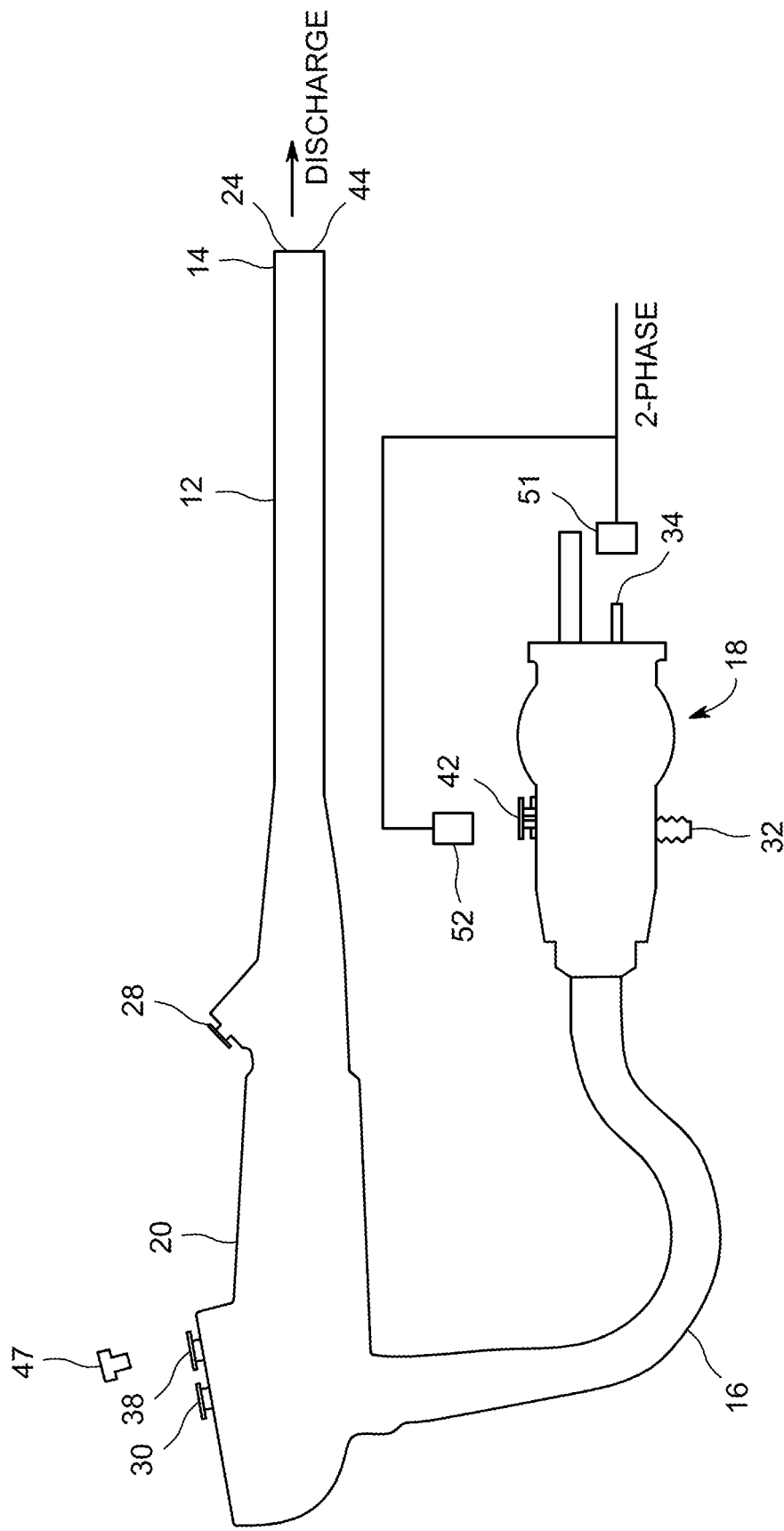
FIG. 22C show connections to an air channel of an endoscope for performing sampling.

This example describes a protocol used for sampling various channels of an endoscope.
Suction/Biopsy Channel Sampling Reference is made to FIG. 22A. To begin the suction/biopsy channel recovery, the suction cylinder 30 opening is occluded by a plug 46 and the biopsy port opening 28 is occluded by a plug 48. Then, a non-leaky adaptor 49 that is connected to a source of two-phase mixture (air+recovery liquid) is connected to the suction port on the umbilical end. The two-phase mixture is applied from the suction port through the suction channel 26 and also to the suction cylinder 30. From there, the two-phase mixture is directed to the suction/biopsy channel 26 and finally is discharged from the distal end to the sterile media bottle.
Water Channel Sampling Reference is made to FIG. 22B. A separator 47 that separates the air and water inside the air/water cylinder 38 is first inserted to the air/water cylinder 38. A non-leaky adaptor 50 that is connected to a source of two-phase mixture (air+recovery liquid) is hooked up to the water port on the umbilical end (as shown in FIG. 3). The two-phase mixture is applied from the air/water port 42 at the umbilical end. The two-phase mixture is directed to the air/water cylinder 38 through the water channel 40. From there, the two-phase-phase mixture is directed through the water channel 40 to the distal end nozzle 44 and discharged to the sterile media bottle.
Air Channel Sampling Reference is made to FIG. 22C. Using the same air/water separator 47 as mentioned in connection with water channel sampling, non-leaky adaptors 51 and 52 that are connected to a source of two-phase mixture (air+recovery liquid) are connected to the air pipe 34 and air/water port 42 on the umbilical end, respectively (as shown in FIG. 4). The two-phase mixture is applied to these two ports simultaneously. The two-phase mixture is directed to the air/water cylinder 38 through the air channel 36. From the air/water cylinder 38 the two-phase mixture is directed through the air channel 36 to the distal end nozzle 44 and discharged to the sterile media bottle.

The sampling and recovery of suction/biopsy channel 26, water channel 40 and air channel 36 can be performed either simultaneously or sequentially, because the two-phase mixture applied to each channel is supplied from a source using independent tubing and connectors. Although these tubings can be handled individually, they can be bundled as a tubing set to save installation time.

For two-phase flow for sampling, Table 3 gives the set pressure for the supplied air, and the flowrate of the sampling liquid, for two different endoscope channels: the suction/biopsy channel and the air/water channel. These parameters are for a particular model of endoscope (an Olympus Colonoscope). For other endoscopes and other channel dimensions, the parameters can be different.

TABLE 3

| Channel | Recovery Liquid Flow Rate (ml/min) | Air Pressure (psi) |
|---|---|---|
| Suction/Biopsy channel | 22 | 28 |
| Air/Water channel | 18 | 28 |

EXAMPLE 3

This Example describes a comparison between the inventive method of sampling and a form of testing referred to as destructive testing. Destructive testing involves physically cutting a short length of the passageway of a device of interest, and processing that sample by a method that is expected to provide virtually complete removal of contaminants. The destructive method involves sonication and vortexing. These methods, although they recover contaminants well, are only applicable to short samples and if the samples are from a longer or larger device, it is necessary to cut those samples out of the longer larger device. Thus, destructive testing forms a useful basis for comparison for the recovery of contaminants by the inventive method, but is not suitable for use on actual devices that have to remain intact. Tables 9A and 9B show that the results of sampling with two-phase flow are very close to the results of destructive testing.

Objective

Compare destructive testing (5 cm segments) to 2-Phase flow sample collection (1 foot length) using Suction Channels and Air/Water channel sets for extraction of: -PTFE-Traditional biofilm (TBF)

Destructive Testing

Destructive testing is conducted pursuant to the following tables:

TABLE 4

| Supplies |
|---|
| Sterile gauze |
| Sterile foil lined container |
| Scalpel with #15 blade |
| Sterile tweezers |
| 30 cm of PTFE-TBF (or PTFE-TBF) |
| Sterile ruler or pieces of sterile foil with masking tape containing the 5 × 1 cm markings (called "sterile ruler"). |

To remove pieces:

TABLE 5

| Destructive Processing |
|---|
| 1) Wear gown and sterile gloves - work under the BSC with fan on. |
| 2) Lay the PTFE-BBF (or PTFE-TBF) tubing inside the foil lined container. |
| 3) Wipe the entire exterior length of PTFE-BBF (or PTFE-TBF) with an alcohol-soaked piece of sterile gauze. Let dry then repeat twice |

TABLE 5-continued

| Destructive Processing |
|---|
| more with alcohol. This ensures the exterior surface of the PTFE has been disinfected. |
| 4) Lay a section of PTFE-BBF (or PTFE-TBF) on the sterile ruler. |
| 5) Use the scalpel to cut the PTFE-BBF (or PTFE-TBF) tubing into 5 cm lengths (x3). |
| 6) Wearing sterile gloves and working on sterile foil or inside a sterile Petri dish, use the sterile scalpel #15 to cut each entire 5 cm of PTFE lengthwise through one layer, then rotate and cut lengthwise through the second layer = 2 × 5 cm pieces. |
| 7) Now cut each of the 2 × 5 cm pieces into 5 × 1 cm pieces = TOTAL OF 10 × 1 cm pieces. |
| 8) Use sterile tweezers to transfer all 10 pieces inside a 50 mL conical tube containing 1X Pineau Neutralizer solution (i.e., 2.5 mL of sterile RO water + 2.5 mL of 2X Pineau Neutralizer) for viable counts of EF and PA. For chemistry test, use 5 mL sRO water instead of 1X Pineau Neutralizer. |

Extraction is pursuant to Table 6:

TABLE 6

| Extraction |
|---|
| 1) Place the 50 mL conical tubes in the sonicator and sonicate for 5 minutes. Note: If performing ATP testing, do so prior to this step (just vortex sample well prior to ATP testing). |
| 2) Vortex for 1 minute per tube. |
| 3) Use the liquid for viable counts and rinse 10 tubing pieces with sterile RO water for $2^{nd}$ extraction. |
| 4) Repeat extraction ($3^{rd}$ extraction). |

Two-Phase Flow Sample Collection

NOTE: The 1 foot length of PTFE-BBF (or PTFE-TBF) can be sandwiched between 2 flanking side lengths (each flanking tubing is 2.5 ft—FIG. 1) of PTFE tubing. When harvesting with 2-Phase flow, the fluid sample obtained will be added to an equal volume of 2× Pineau Neutralizer or other neutralizer for viable counts of EF and PA. The process is conducted pursuant to the following tables:

TABLE 7

Figure 23A:
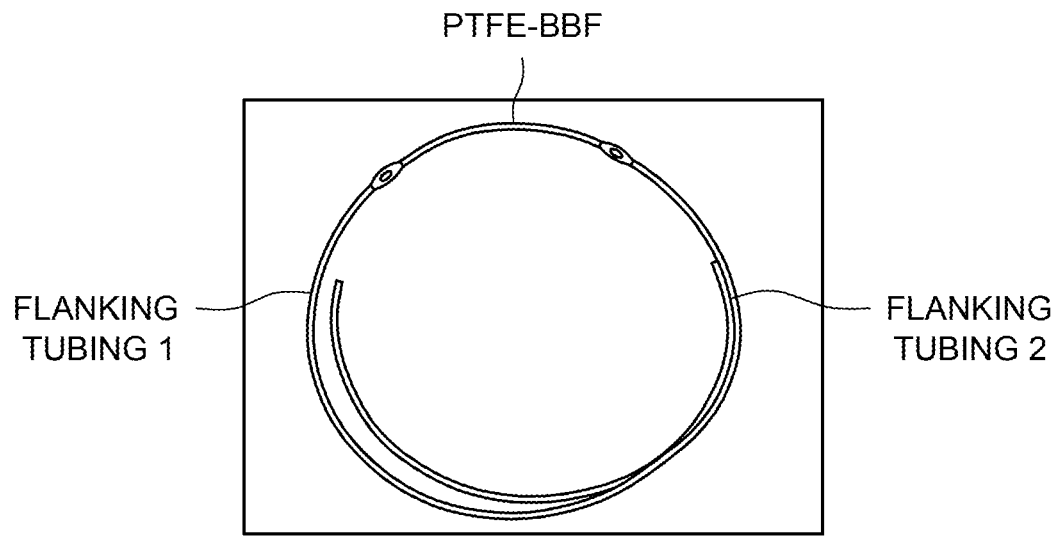
FIG. 23A shows a tubing connection for an experimental protocol.
Figure 23B:
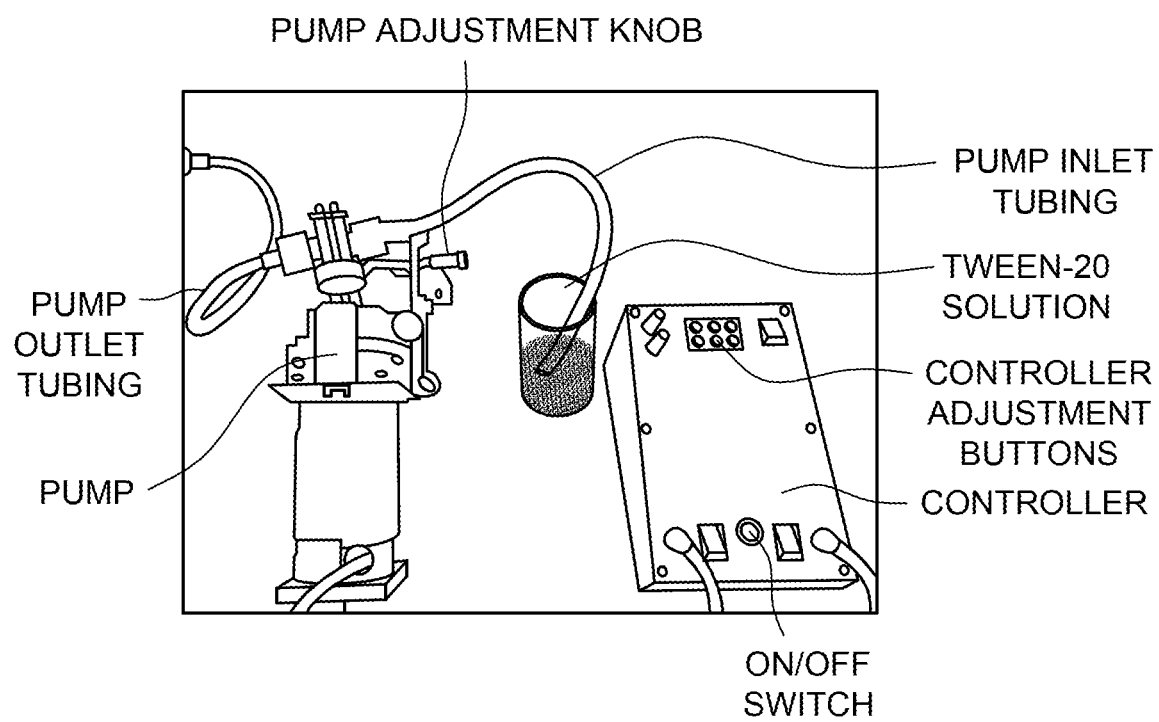
FIG. 23B shows a pump and controller and tubing connection for an experimental protocol.
Figure 23C:
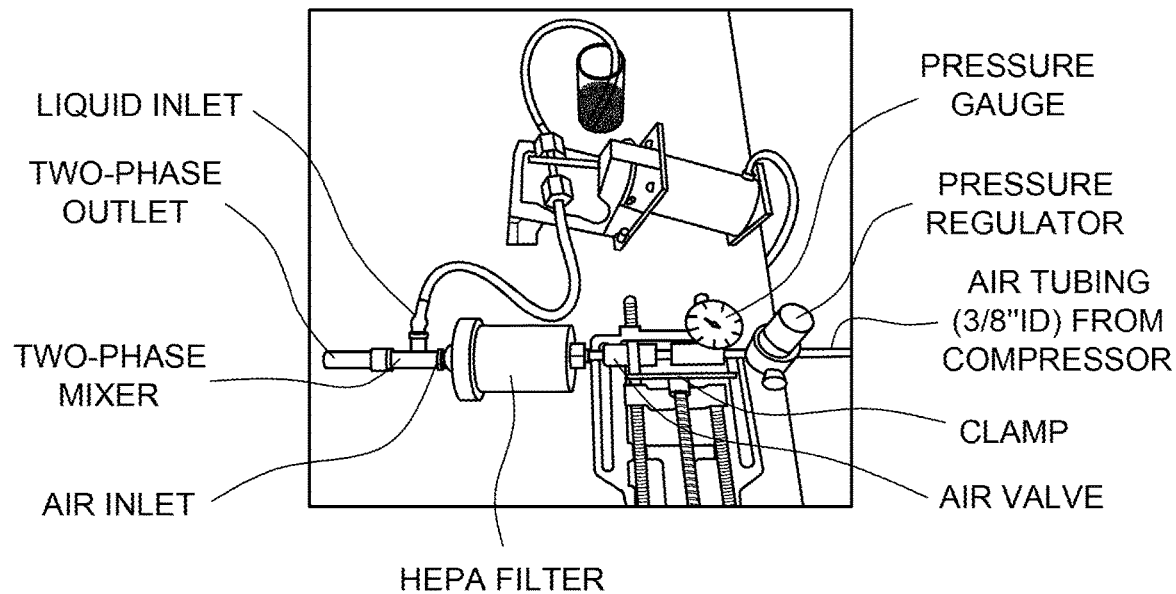
FIG. 23C shows a two-phase flow generator for an experimental protocol.
Figure 23D:
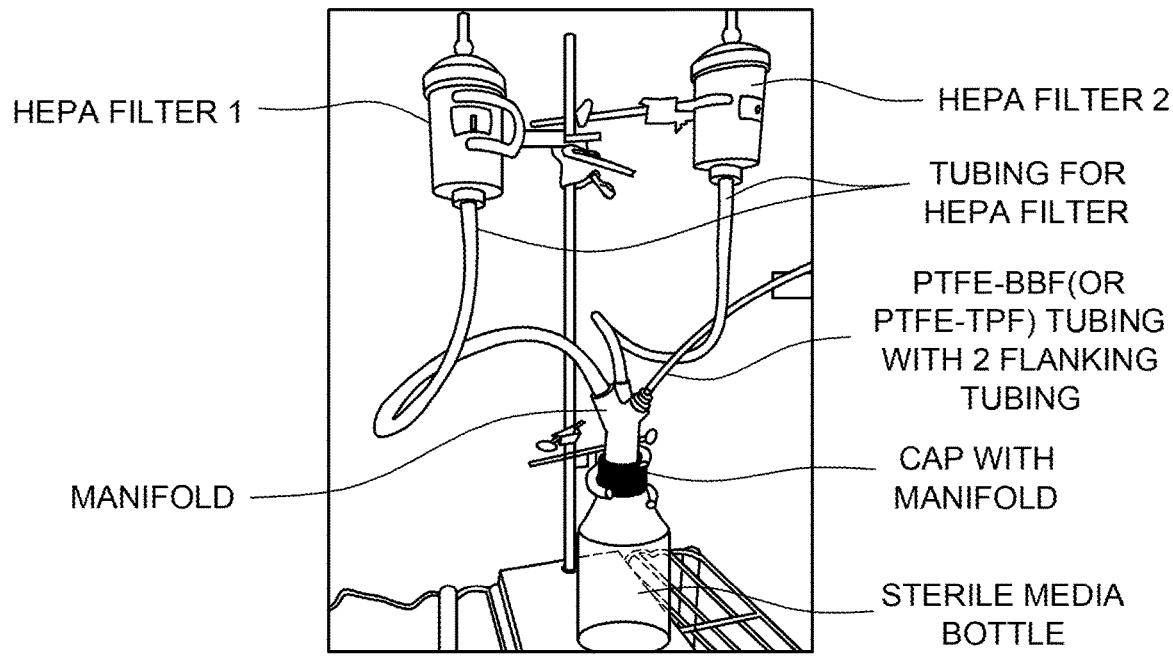
FIG. 23D shows a sterile media bottle with HEPA filters for venting.

| Supplies |
|---|
| Sterile gauze |
| Sterile foil lined container |
| Scalpel with #15 blade |
| 3 ft of PTFE-BBF (or PTFE-TBF) |
| Sterile ruler |
| Sterile media bottle, 500 mL (VWR 89132-058) |
| Cap with manifold (Kinesis BC-326) for sterile media bottle with three ports, two for HEPA filter tubing and one for PTFE tubing (see FIG. 23D) |
| Stand with three clamps, two for holding the HEPA filters and one for holding the sterile bottle cap with manifold (see FIG. 23D) |
| Pump (FMI Q1SAN) with ¼ " ID Silicon Tubing and Controller (FMI V200) - see FIG. 23B |
| Air compressor (Shulz MSV 6/30) inside a cabinet with ⅜"ID tubing |
| Two-phase flow Generator with air inlet, liquid inlet, air regulator, pressure gauge, HEPA filter, two-phase mixer, air valve and two-phase outlet (FIG. 23C) |

Processing is pursuant to the following Table 8:

TABLE 8

Two-Phase Processing

1) Wear gown and sterile gloves - work under the BSC with fan on (Steps 1 to 5 below).
2) Lay the PTFE-BBF (or PTFE-TBF) tubing inside the foil lined container.
3) Wipe the entire exterior length of PTFE-BBF (or PTFE-TBF) with an alcohol-soaked piece of sterile gauze. Let dry then repeat twice more with alcohol. This ensures the exterior surface of the PTFE has been disinfected.
4) Lay a section of PTFE-BBF (or PTFE-TBF) on the sterile ruler.
5) Use the scalpel to cut the PTFE-BBF (or PTFE-TBF) tubing into 1 foot lengths.
6) Connect 1 ft PTFE-BBF (or PTFE-TBF) tubing to two flanking PTFE tubing using push-on connectors.
7) Remove the cap from the sterile media bottle. Attach a cap with manifold to the sterile media bottle.
8) Connect the first HEPA filter tubing to HEPA Filter 1 and one of the ports on the manifold.
9) Connect the second HEPA filter tubing to HEPA Filter 2 and the other port on the manifold.
10) Connect one side of 1 ft PTFE-BBF (or PTFE-TBF) tubing with 2 flanking tubing to the push-on connector on the manifold (FIG. 23D).
11) Connect the other side of 1 ft PTFE-BBF (or PTFE-TBF) tubing with 2 flanking tubing to the push-on connector at two-phase outlet (FIG. 23C).
12) Start the compressor by turning 'ON' the 'ON/OFF' switch on the compressor cabinet.
13) Adjust the air pressure to 28 psi on the two-phase generator using the pressure regulator (FIG. 23C).
14) Adjust the pump setting to 50% on the dial by using the pump adjustment knob on the pump (FMI Q1SAN) - FIG. 23B.
15) Adjust the controller setting to 10% by using the three adjustment buttons on the controller (FMI V200) - FIG. 23B. This will provide a liquid flow rate of 22 ml/min.
16) Turn 'ON' the pump by pressing the 'ON' button on the controller - FIG. 23B.
17) Use 100 mL 0.075% Tween 20 in 1X PBS for each harvesting (Three harvests for each 1 ft tubing).
18) Turn 'ON' air by opening the air valve on the two-phase generator (FIG. 23C).
19) Once 100 mL of Tween 20 is finished, stop the pump and close the air valve on the two-phase generator.
20) Disconnect all the tubing from the manifold.
21) Remove the cap with manifold from the bottle.
22) Replace the original cap on the bottle.
23) Weigh the bottle using an analytical balance.
24) Keep ~2 mL sample for chemistry test (can be frozen for 2 weeks). Add same amount of 2X Pineau Neutralizer to the remaining sample.
For all collected sample, viable count (EF and PA) and organic residuals (protein, carbohydrate, and hemoglobin) will be tested.
For viable count: Perform serial 1:10 dilutions from $10^{-1}$ through $10^{-8}$ (50 µL sample + 450 µL sPBS) and plate 100 µL × 1 of the direct through $10^{-8}$ dilutions (9 BA per replicate). Spread inoculum, incubate overnight and count EF and PA colonies and record.

The comparative results are set forth below in Tables 9A and 9B:

TABLE 9A

Two-Phase Testing

| Sample | Protein Conc. (µg/mL) | Protein Conc. (µg/cm²) | Carbohydrate Conc. (µg/mL) | Carbohydrate Conc. (µg/cm²) | Hemoglobin Conc. (µg/cmL) | Hemoglobin Conc. (µg/cm²) |
|---|---|---|---|---|---|---|
| Harvest1 | 6.111 | 37.536 | 3.175 | 19.499 | 0.107 | 0.656 |
| Harvest2 | 0.378 | 2.389 | 0.159 | 1.004 | 0.047 | 0.300 |
| Harvest3 | 0.178 | 1.122 | 0.000 | 0.000 | 0.024 | 0.150 |

TABLE 9B

Destructive Testing

| Sample | Protein Conc. (µg/mL) | Protein Conc. (µg/cm²) | Carbohydrate Conc. (µg/mL) | Carbohydrate Conc. (µg/cm²) | Hemoglobin Conc. (µg/mL) | Hemoglobin Conc. (µg/cm²) |
|---|---|---|---|---|---|---|
| Harvest1 | 7.533 | 15.007 | 2.857 | 5.692 | 0.107 | 0.213 |
| Harvest2 | 3.044 | 6.065 | 1.111 | 2.213 | 0.012 | 0.024 |
| Harvest3 | 0.844 | 1.682 | 1.429 | 2.846 | 0.047 | 0.095 |

For organic residues, equivalent results have been obtained. This also demonstrates that testing with SRO is effective for both organisms and organic residues.

EXAMPLE 4

Recovery of organisms and molecular residues (protein, carbohydrates and hemoglobin) from endoscope suction/ biopsy PTFE tubing (3.2 mm ID) where the contaminants comprise traditional polymicrobial biofilm This example demonstrates the effectiveness of the inventive two-phase flow method and apparatus in the recovery and sampling of traditional biofilm from 3.2-mm diameter PTFE suction/biopsy endoscope channels. Polymicrobial traditional biofilm was prepared as described elsewhere herein. The recovery was performed by two methods: 1) the inventive two-phase flow method using the apparatus described elsewhere herein, and by 2) the destructive testing method as described in the published literature (Ref. "Alfa et al., cited above). The recovery was done by performing three harvestings using the same tubing with the same built-up biofilm to assess and demonstrate the effectiveness of the inventive technology. Organisms and molecular residues in the recovered samples were quantitated by culture methods for organisms and by special analysis for molecular residues, respectively, and as described elsewhere herein. The results are summarized in Tables 4A and 4B, for two-phase and destructive methods respectively.

Biofilm recovery effectiveness: For the two organisms (EF and PA) making up the built-up biofilm, the two organisms were recovered at 97.6% effectiveness in one harvesting using the inventive two-phase flow technology. This is compared to 89.7% and 91.8% for EF and PA, respectively, when the recovery is performed by destructive testing. This result supports the success and superiority of the inventive recovery and sampling techniques using the inventive two-phase flow method and apparatus according to the invention. Moreover, because the recovery with the inventive technology is not destructive, it can thus be used to recover and sample biofilms from intact endoscopes. Accordingly, the inventive technology is applicable for routine sampling to assess the cleaning effectiveness of endoscopes and to ensuring that the endoscopes are safe to use on patients. Sampling an endoscope after high-level disinfection and before it is used to perform endoscopy can also save lives by preventing fatal infections of patients undergoing invasive procedure such as ERCP or when in the endoscope is to be used in a normally sterile organ such as in the lung (bronchoscopy) and in the bladder (cystocopy). Various sterile liquids can be used to perform the recovery and sampling as summarized in Tables 1A and 1B. Selection of other sterile recovery liquids can be made as required and the invention is not meant to be limited to the list provided in Tables 1A or 1B or elsewhere herein.

Organic residues in the recovered samples are provided in Table 10A and 410B for the inventive technology and for destructive testing, respectively. The data shows that the inventive methods achieve reliable organic residues recovery when compared with destructive testing. In summary, both organism and organic residues can be effectively and noninvasively recovered and sample with the inventive technology.

TABLE 10A

| | cfu/mL | | cfu/cm$^2$ | | Protein | |
|---|---|---|---|---|---|---|
| | | | | | Conc. (µg/mL) | Conc. (µg/cm$^2$) |
| Sample | EF | PA | EF | PA | | |
| Harvest1 | 450333 | 13933333 | 1378677 | 42623586 | 4.149 | 12.723 |
| Harvest2 | 10667 | 330247 | 33142 | 1026094 | 0.000 | 0.000 |
| Harvest3 | 160 | 12333 | 508 | 39125 | 0.000 | 0.000 |

TABLE 10A-continued

| | Carbohydrate | | Hemoglobin | |
|---|---|---|---|---|
| Sample | Conc. (µg/mL) | Conc. (µg/cm$^2$) | Conc. (µg/mL) | Conc. (µg/cm$^2$) |
| Harvest1 | 3.056 | 9.374 | 1.012 | 3.093 |
| Harvest2 | 0.222 | 0.690 | 0.179 | 0.555 |
| Harvest3 | 0.111 | 0.352 | 0.119 | 0.374 |

Harvesting solution: 0.075% tween 20 in 1× PBS (R1), 0.075% tween 20 in 1× PBS with 1% Syloid EXF150 (R2, R3).

TABLE 10B

| | cfu/mL | | cfu/cm$^2$ | | Protein | |
|---|---|---|---|---|---|---|
| | | | | | Conc. (µg/mL) | Conc. (µg/cm$^2$) |
| Sample | EF | PA | EF | PA | | |
| Harvest1 | 570000 | 23726667 | 566600 | 23585156 | 14.008 | 13.924 |
| Harvest2 | 58647 | 1956667 | 58297 | 1944997 | 1.452 | 1.443 |
| Harvest3 | 13407 | 319167 | 13327 | 317263 | 1.028 | 1.021 |

| | Carbohydrate | | Hemoglobin | |
|---|---|---|---|---|
| Sample | Conc. (µg/mL) | Conc. (µg/cm$^2$) | Conc. (µg/mL) | Conc. (µg/cm$^2$) |
| Harvest1 | 7.879 | 7.832 | 0.423 | 0.420 |
| Harvest2 | 1.818 | 1.807 | 0.008 | 0.008 |
| Harvest3 | 0.202 | 0.201 | 0.008 | 0.008 |

Harvesting Solution: 1× Pineau neutralizer for bioburden and sRO water for chemistry tests.

EXAMPLE 5

Recovery of organisms and organic residues (protein, carbohydrates and hemoglobin) from narrow endoscope PTFE channels (1.6 mm ID) where the contaminants comprise traditional polymicrobial biofilm This example demonstrates the effectiveness of recovering organisms from traditional polymicrobial biofilms from the narrow endoscope channels (e.g., air, water, auxiliary channels) having diameter of about 1.6 mm inside diameter. Traditional polymicrobial biofilms were prepared as described elsewhere herein. The methods, procedures and techniques for recovering, culturing and quantitating organisms are the same as described in Example 4.

Recovery effectiveness, computed from the ratio of cfu/cm$^2$ of second harvesting to first harvesting, was found to be 99.99% for both EF and PA organisms comprising the traditional biofilm. For destructive testing, the recovery effectiveness was 85.2% for EF and 78.9% for PA, as provided in Tables 11A and 11B below. The data obtained supports the applicability and superiority of the inventive technology to recover and sample biofilm organisms from narrow lumens such as endoscopes. The effectiveness value computed here is further supported by SEM examination of the surface of the tube after the recovery and quantitating of the residual organisms remaining on the surface.

Organic residues data of recovered samples obtained by the inventive methods were found to be significantly lower than that of destructive testing, as shown Table 11A and 11B. This can be due to adsorption of organic residue on the silica gel particle used to recover the contaminants with the inventive two-phase flow methods. Although the presence of silica or like particles facilitated excellent and full recovery of biofilm from the lumens, it may compromise the recovery of organic residues. In an embodiment of the invention, we found that using recovery liquids that do not include silica particles is appropriate for recovering organic residues as described elsewhere herein. In a related embodiment, if the used of particles is deemed necessary to recover biofilms, hydrophilic silica or other particles with very low capacity to adsorb organic residues can be used in the recovery fluids.

These results are particularly important since the endoscope narrow channels such as air, water and auxiliary channels cannot be sampled by brushing due to their small inside diameters. In this context, the inventive technology provides applicable and practical methods that can used on large scale in the field, and they are safe and non-destructive to the medical device. Furthermore, the apparatus and methods of the invention are convenient and less time consuming to employ in healthcare facilities. This is important since there is an urgent need for technologies that can help to prevent infections arising from use of medical devices such as endoscopes.

TABLE 11A

| Sample | cfu/mL EF | cfu/mL PA | cfu/cm² EF | cfu/cm² PA | Protein Conc. (µg/mL) | Protein Conc. (µg/cm²) |
|---|---|---|---|---|---|---|
| Harvest1 | 523333 | 14566667 | 3576327 | 97392515 | 0.000 | 0.000 |
| Harvest2 | 113 | 570 | 719 | 3668 | 0.000 | 0.000 |
| Harvest3 | 17 | 20 | 127 | 138 | 0.000 | 0.000 |

| Sample | Carbohydrate Conc. (µg/mL) | Carbohydrate Conc. (µg/cm²) | Hemoglobin Conc. (µg/mL) | Hemoglobin Conc. (µg/cm²) |
|---|---|---|---|---|
| Harvest1 | 0.000 | 0.000 | 0.407 | 2.732 |
| Harvest2 | 0.117 | 0.759 | 0.346 | 2.233 |
| Harvest3 | 0.000 | 0.000 | 0.481 | 3.451 |

Harvesting solution: 0.075% Tween 20 in 1× PBS with 1% Syloid EXF150.

TABLE 11B

| Sample | cfu/mL EF | cfu/mL PA | cfu/cm² EF | cfu/cm² PA | Protein Conc. (µg/mL) | Protein Conc. (µg/cm²) |
|---|---|---|---|---|---|---|
| Harvest1 | 460333 | 21300000 | 916999 | 42430279 | 8.101 | 16.137 |
| Harvest2 | 68267 | 4504667 | 135989 | 8973440 | 2.238 | 4.458 |
| Harvest3 | 2647 | 62233 | 5272 | 123971 | 0.757 | 1.507 |

| Sample | Carbohydrate Conc. (µg/mL) | Carbohydrate Conc. (µg/cm²) | Hemoglobin Conc. (µg/mL) | Hemoglobin Conc. (µg/cm²) |
|---|---|---|---|---|
| Harvest1 | 3.757 | 7.483 | 0.124 | 0.248 |
| Harvest2 | 2.593 | 5.165 | 0.060 | 0.119 |
| Harvest3 | 1.640 | 3.267 | 0.037 | 0.073 |

Harvesting Solution: sRO water.

EXAMPLE 6

Recovery of organisms and molecular residues (protein, carbohydrates and hemoglobin) from endoscope suction/biopsy PTFE tubing (3.2 mm ID) where the contaminants comprising built-up polymicrobial biofilm.

The built up polymicrobial biofilm was prepared according to Alfa et al. (Alfa et al., A novel polytetrafluoroethylene-channel model, which simulates low levels of culturable bacteria in buildup biofilm after repeated endoscope reprocessing. Gastrointestinal endoscopy, DOI: http://dx.doi.org/10.1016/j.gie.2017.05.014, in press)). The same channel with the same biofilm grown within it was used to compare the recovery effectiveness of the inventive method with the published destructive test methods (Alfa et al., cited above). The methods of recovery, culturing and quantitation of organisms are the same as described in Example 4.

The effectiveness of recovering built up biofilm with the inventive technology as quantitated by the number of recovered organisms were: 1) for EF: 29% calculated based on two harvestings and 88% calculated based on three harvestings; and 2) for PA: 99.9% based on two harvestings and about 100% based on three harvestings. The results are summarized in Table 12A. In contrast, the effectiveness of recovering built-up biofilm as quantitated by the number of organisms according to published destructive methods was too low where hardly any organisms could be recovered as shown in Table 12B. Accordingly, the inventive technology is effective at sampling built-up biofilm from the 3.2 mm endoscope suction/biopsy channel. Because built-up biofilm has been recognized as a major risk in transmitting infection from endoscopy, the inventive methods and apparatus can be considered to be the only way to recover and sample this strong mature biofilm from medical devices.

TABLE 12A

| Sample | cfu/mL EF | cfu/mL PA | cfu/cm² EF | cfu/cm² PA | Protein Conc. (µg/mL) | Protein Conc. (µg/cm²) |
|---|---|---|---|---|---|---|
| Harvest1 | 2024000 | 316000 | 6111880 | 955896 | 3.085 | 9.411 |
| Harvest2 | 1435333 | 427 | 4439837 | 1319 | 0.308 | 0.952 |
| Harvest3 | 239867 | 0 | 735396 | 0 | 0.020 | 0.062 |

| Sample | Carbohydrate Conc. (µg/mL) | Carbohydrate Conc. (µg/cm²) | Hemoglobin Conc. (µg/mL) | Hemoglobin Conc. (µg/cm²) |
|---|---|---|---|---|
| Harvest1 | 0.000 | 0.000 | 5.664 | 17.252 |
| Harvest2 | 0.265 | 0.819 | 5.474 | 16.806 |
| Harvest3 | 0.000 | 0.000 | 7.525 | 23.284 |

Harvesting solution: 0.075% tween 20 in 1× PBS (R1), 0.075% tween 20 in 1× PBS with 1% syloid EXF150 (R2, R3).

TABLE 12B

| Sample | cfu/mL EF | cfu/mL PA | cfu/cm² EF | cfu/cm² PA | Protein Conc. (µg/mL) | Protein Conc. (µg/cm²) |
|---|---|---|---|---|---|---|
| Harvest1 | 63 | 22357 | 63 | 22223 | 30.346 | 30.165 |
| Harvest2 | 7 | 6673 | 7 | 6634 | 9.974 | 9.914 |
| Harvest3 | 0 | 673 | 0 | 669 | 4.288 | 4.263 |

TABLE 12B-continued

|  | Carbohydrate | | Hemoglobin | |
| --- | --- | --- | --- | --- |
| Sample | Conc. ($\mu$g/mL) | Conc. ($\mu$g/cm$^2$) | Conc. ($\mu$g/mL) | Conc. ($\mu$g/cm$^2$) |
| Harvest1 | 10.145 | 10.084 | 4.952 | 4.922 |
| Harvest2 | 3.816 | 3.794 | 0.360 | 0.358 |
| Harvest3 | 2.174 | 2.161 | 0.041 | 0.040 |

Harvesting Solution: 1× Pineau Neutralizer for bioburden, SRO water for chemistry tests.

EXAMPLE 7

Recovery of organisms and molecular residues (protein, carbohydrates and hemoglobin) from endoscope narrow PTFE channels (1.6 mm ID) where the contaminants comprise built-up polymicrobial biofilm.

The experiments were performed following the methods described in Example 4. The recovery effectiveness of the inventive technology of recovering built up biofilm from 1.6 mm channels was: 1) for EF 96.4% and 2) for PA 99.6% as shown in Table 7A. The number of organisms recovered with published destructive methods is shown in Table E8. Based on these results, the inventive technology is capable of recovering and sampling the most difficult organisms from the narrow endoscope channels (about 1.6 mm ID or smaller), including air, water and auxiliary channels.

The recovery of organic residues with the inventive technology as shown in Table 13A was lower than that of destructive testing. This may be due to the presence of silica gel particles in the recovery liquid used to make the two-phase mixture. The silica particles may adsorb some of the organic molecules as described elsewhere herein. According to an embodiment, it may be advantageous if the particles used in the recovery composition have very low or no adsorption capacity for organic residues. Examples of appropriate particles include hydrophilic silica, and polymer particles that have low protein adsorbing capacity such as polytetrafluoroethylene (Teflon®) and other inorganic particles that can be functionalized to have low adsorption for molecular residues under consideration.

TABLE 13A

|  | cfu/mL | | cfu/cm$^2$ | | Protein | |
| --- | --- | --- | --- | --- | --- | --- |
| Sample | EF | PA | EF | PA | Conc. ($\mu$g/mL) | Conc. ($\mu$g/cm$^2$) |
| Harvest1 | 953 | 21333 | 5852 | 1314291 | 0.084 | 0.525 |
| Harvest2 | 33 | 7 | 212 | 42 | 0.000 | 0.000 |
| Harvest3 | 0 | 0 | 0 | 0 | 0.000 | 0.000 |

|  | Carbohydrate | | Hemoglobin | |
| --- | --- | --- | --- | --- |
| Sample | Conc. ($\mu$g/mL) | Conc. ($\mu$g/cm$^2$) | Conc. ($\mu$g/mL) | Conc. ($\mu$g/cm$^2$) |
| Harvest1 | 0.000 | 0.000 | 0.208 | 1.288 |
| Harvest2 | 0.056 | 0.349 | 0.179 | 1.127 |
| Harvest3 | 0.000 | 0.000 | 0.198 | 1.249 |

Harvesting Solution: 0.075% Tween20 in 1× PBS with 1% Syloid EXF150.

TABLE 13B

|  | cfu/mL | | cfu/cm$^2$ | | Protein | |
| --- | --- | --- | --- | --- | --- | --- |
| Sample | EF | PA | EF | PA | Conc. ($\mu$g/mL) | Conc. ($\mu$g/cm$^2$) |
| Harvest1 | 1357 | 188667 | 2703 | 375830 | 10.996 | 21.903 |
| Harvest2 | 310 | 12357 | 618 | 24615 | 3.044 | 6.064 |
| Harvest3 | 440 | 6000 | 876 | 11952 | 0.951 | 1.894 |

|  | Carbohydrate | | Hemoglobin | |
| --- | --- | --- | --- | --- |
| Sample | Conc. ($\mu$g/mL) | Conc. ($\mu$g/cm$^2$) | Conc. ($\mu$g/mL) | Conc. ($\mu$g/cm$^2$) |
| Harvest1 | 4.444 | 8.853 | 0.217 | 0.433 |
| Harvest2 | 0.606 | 1.207 | 0.032 | 0.064 |
| Harvest3 | 0.000 | 0.000 | 0.016 | 0.032 |

Harvesting Solution: 1× Pineau Neutralizer for bioburden, SRO water for chemistry tests.

EXAMPLE 8

Recovery of a mixture of organisms and organic residues from actual endoscopes (Olympus Colonoscope CF Type Q160L)

This example demonstrates the recovery and sampling of organisms and organic residues from actual endoscopes. Three organisms are used to represent Gram positive bacteria (EF), Gram negative bacteria (PA) and yeast (CA) as is accepted in the industry for evaluating cleaning effectiveness of endoscopes. The organisms are suspended in the Artificial Testing Soil (ATS) as published by Alfa et al. (Ref "Alfa et al., 2010. EVOTECH® endoscope cleaner and reprocessor (ECR) simulated-use and clinical-use evaluation of cleaning efficacy, BMC Infectious Diseases. BMC Infectious Diseases 2010, 10:20 www.biomedcentral.com/1471-2334/10/200)"). The ATS soil was developed to mimic organic residues left in flexible endoscopes after a gastrointestinal endoscopic procedure, including protein, carbohydrate and hemoglobin. The soil-organisms mixture, referred to as the "bug mix in ATS-T", was introduced in the endoscope channels and allowed to reside there for two hours before recovery according a standard method which is widely accepted in industry. The organisms in this organic test soil are mostly in the planktonic form, in contrast with the other example above, which were focused on biofilms.

A sample for negative control was collected before soiling the endoscope. Negative control harvested sample was concentrated by ultrafiltration before viable count. The organisms used were: EF, *Enterococcus faecalis*; PA, *Pseudomonas aeruginosa*; CA, *Candida albicans*. This test was performed to determine the effectiveness of the technology in recovering the organisms and organics residues similar to other examples.

The recovery was performed three consecutive times of the same endoscope. The recovered samples are referred to as Harvest 1, 2 and 3, as shown in Table 8. The recovery/sampling liquid used in each harvest was 100 ml sterile reverse osmosis water (SRO). After completing the three recoveries or harvestings, an additional recovery was performed according to standard manual methods using flush/brush/flush for the suction/biopsy channel and flush/flush for the air/water channel and the recovered sample is referred to as Harvest 4 in Table 14. Harvest 4 was done to ensure that the recovery of endoscope channels using the inventive technology is complete and effective.

The results in Table 14 confirm the inventive technology is more than 99% effective in recovering organisms from all endoscope the channels without the need for brushing, and that one harvesting is sufficient to provide excellent sampling of actual endoscopes.

TABLE 14

|  |  | A/W, 100 mL | | | | S/B, 100 mL | | | |
| --- | --- | --- | --- | --- | --- | --- | --- | --- | --- |
|  |  | cfu/mL | cfu/CH | cfu/cm$^2$ | Log$_{10}$ cfu/cm$^2$ | cfu/mL | cfu/CH | cfu/cm$^2$ | Log$_{10}$ cfu/cm$^2$ |
| Bug Mix | EF | 440000 | 7392000 | 28591.32 | 4.456 | 480000 | 20928000 | 52505.08 | 4.720 |
|  | PA | 71666.67 | 1204000 | 4656.92 | 3.668 | 293333.3 | 12789333 | 32086.44 | 4.506 |
|  | CA | 916666.7 | 15400000 | 59565.25 | 4.775 | 473333.3 | 20637333 | 51775.84 | 4.714 |
| Negative | EF | 0 | 0 | 0 |  | 0 | 0 | 0 |  |
| Control | PA | 0 | 0 | 0 |  | 0 | 0 | 0 |  |
|  | CA | 0 | 0 | 0 |  | 0 | 0 | 0 |  |
| Harvest 1 | EF | 150666.7 | 14162667 | 54779.4 | 4.739 | 305333.3 | 41036800 | 102954.9 | 5.013 |
|  | PA | 8633.333 | 811533.3 | 3138.908 | 3.497 | 15000 | 2016000 | 5057.829 | 3.704 |
|  | CA | 137666.7 | 12940667 | 50052.86 | 4.699 | 188333.3 | 25312000 | 63503.85 | 4.803 |
| Harvest 2 | EF |  | 1228.333 | 4.751038 | 0.677 |  | 17628 | 44.2259 | 1.646 |
|  | PA |  | 42.33333 | 0.16374 | −0.786 |  | 23 | 0.057703 | −1.239 |
|  | CA |  | 1061.333 | 4.105103 | 0.613 |  | 10165 | 25.5024 | 1.407 |
| Harvest 3 | EF |  | 77.93333 | 0.301436 | −0.521 |  | 3328 | 8.349432 | 0.922 |
|  | PA |  | 26.86667 | 0.103917 | −0.983 |  | 0 | 0 |  |
|  | CA |  | 107.4 | 0.41541 | −0.382 |  | 422 | 1.058732 | 0.025 |
| Harvest 4 | EF |  |  |  |  |  | 1790 | 4.49083 | 0.652 |
|  | PA |  |  |  |  |  | 0 | 0 |  |
|  | CA |  |  |  |  |  | 1337 | 3.354324 | 0.526 |

EXAMPLE 9

Recovery and sampling of traditional biofilm form 1.6 mm ID channels using SRO as the recovery liquid This example demonstrates the effectiveness of the inventive technology in sampling endoscope channels using SRO as the recovery liquid. Using SRO as the recovery liquid is useful in order to avoid introducing other additives into the endoscope during the recovery and sampling procedures. This is particularly useful if the endoscope is already high-level disinfected (or sterilized) and is to be used on a patient. Although the inclusion of other additives in the recovery liquid may improve the effectiveness of the recovery, such additives may complicate the protocol in the clinical setting. The results of this testing are included in Tables 15A and 15B.

The results of Tables 15A and 15B show that the recovery of organisms from endoscope channels containing traditional biofilm can be performed with SRO as the only recovery liquid. When the recovery results are compared with those of destructive testing, they support the applicability and versatility of the inventive technology in sampling lumens and that this can be done without destroying the medical devices such as endoscopes.

TABLE 15A

Recovery and sampling of organisms from traditional biofilm grown in 1.6 mm ID channels with the inventive technology using sterile RO water, 100 mL, as the recovery liquid

| Sample | cfu/mL | | Log$_{10}$ cfu/mL | | cfu/cm$^2$ | | Log$_{10}$ cfu/cm$^2$ | |
| --- | --- | --- | --- | --- | --- | --- | --- | --- |
|  | EF | PA | EF | PA | EF | PA | EF | PA |
| Harvest1 | 94000 | 29000000 | 4.97 | 7.46 | 577376 | 178126632 | 5.76 | 8.25 |
| Harvest2 | 2900 | 1490000 | 3.46 | 6.17 | 18343 | 9424347 | 4.26 | 6.97 |
| Harvest3 | 90 | 154000 | 1.95 | 5.19 | 568 | 972050 | 2.75 | 5.99 |

TABLE 15B

Recovery and sampling of organisms from traditional biofilm grown in 1.6 mm ID channels with "destructive method" using sterile RO water, 100 mL, as the recovery liquid

| Sample | cfu/mL | | $Log_{10}$ cfu/mL | | cfu/cm$^2$ | | $Log_{10}$ cfu/cm$^2$ | |
|---|---|---|---|---|---|---|---|---|
| | EF | PA | EF | PA | EF | PA | EF | PA |
| Harvest1 | 50000 | 42000000 | 4.70 | 7.62 | 99602 | 83665339 | 5.00 | 7.92 |
| Harvest2 | 25900 | 7800000 | 4.41 | 6.89 | 51594 | 15537849 | 4.71 | 7.19 |
| Harvest3 | 940 | 310000 | 2.97 | 5.49 | 1873 | 617530 | 3.27 | 5.79 |

This invention described herein is of a sampling system and methods of forming and using the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. More specifically, those of skill will recognize that any embodiment described herein that those of skill would recognize could advantageously have a sub-feature of another embodiment, is described as having that subfeature.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

The invention can be described with reference to the following numbered embodiments:

Embodiment A1. A sampling system for determining an amount or type of contamination a narrow, elongated passageway in a medical device, said sampling system comprising: (a) a fluid supply system that supplies to said passageway a sampling liquid for flowing through said passageway and a gas for flowing through said passageway; and (b) a receiving container that receives liquid from said passageway, wherein said sampling liquid is sterile, wherein said sampling liquid is configured to allow recovery of viable pathogens from the passageway, and wherein said sampling liquid comprises an amount and selection of surfactant effective to enhance the dislodgement of *Enterococcus faecalis* and *Pseudomonas aeruginosa* bacteria from the narrow passageways. [The recited bacteria establish a standard for the surfactant. These bacteria may or may not be sampled in use, and other organisms may be sampled.)

Embodiment A2. The system of an A Embodiment, wherein said fluid supply system further comprises a source of pressurized gas configured with the fluid supply system to create two-phase flow of said gas and said sampling liquid in said passageway.

Embodiment A3. The system of an A Embodiment, wherein said sampling liquid has a contact angle that is less than 20 degrees.

Embodiment A4. The system of an A Embodiment, wherein said sampling liquid has an oncotic pressure equal to or approximately equal to an oncotic pressure of human tissue.

Embodiment A5. The system of an A Embodiment, wherein said sampling liquid has a pH in the range from 2 to 13.

Embodiment A6. The system of an A Embodiment, wherein said sampling liquid has a pH in the range from 6 to 7.5.

Embodiment A7. The system of an A Embodiment, wherein said surfactant has in aggregate a Hydrophilic-Lipophilic Balance of greater than 14.

Embodiment A8. The system of an A Embodiment, wherein said surfactant comprises a non-ionic surfactant.

Embodiment A9. The system of an A Embodiment, wherein said surfactant comprises a member of the Tween family of surfactants or the Pluronic family of surfactants or equivalent.

Embodiment A10. The system of an A Embodiment, wherein said surfactant and amount thereof are selected to avoid denaturing albumin.

Embodiment A12. The system of an A Embodiment, wherein said surfactant and amount there are selected to avoid inactivating HIV, HCV, or HBV virons.

Embodiment A12A. The system of an A Embodiment, wherein said sampling liquid as supplied is selected to avoid killing bacteria or inactivating HIV, HCV, or HBV virons.

Embodiment A13. The system of an A Embodiment, wherein said sampling liquid is non-immunogenic to human cell lines that normally contact said endoscope during an endoscopic procedure and does not introduce any new substance that is irritating or inflammatory to epithelial cells that line body cavity or tissue.

Embodiment A14. The system of an A Embodiment, wherein said sampling liquid further comprises solid particles effective to enhance recovery of bioburden from the passageway.

Embodiment A14A. The system of an Embodiment A14, wherein said sampling liquid further comprises solid particles that have a hardness of at least 2 on the Mohs hardness scale.

Embodiment A15. The system of an Embodiment A14, wherein said solid particles and amount thereof are selected to allow recovery of pathogens from the passageway.

Embodiment A16. The system of an A Embodiment, wherein said sampling liquid further comprises a neutralizer for neutralizing a disinfectant used in disinfecting a medical device with elongated narrow passageways.

Embodiment A17. The system of Embodiment A16, wherein said neutralizer comprises lecithin or L-histidin or sodium thiosulfate or histidine chlorhydrate.

Embodiment A18. The system of an A Embodiment, configured for the two or more narrow passageways of an endoscope and wherein the fluid supply system is automated for delivering specified flowrates at specified pressure for specified periods of time to specified ones of said narrow passageways of said endoscope.

Embodiment A19. The system of an A Embodiment 8, wherein said system is configured to receive outflow from the two or more narrow passageways of said endoscope and deliver said outflow to said collection container.

Embodiment A20. The system of an A Embodiment, wherein liquid-contacting components of said system, in a condition after sterilization, are free of leachable substances in amounts that are harmful to the measurable recovery of *Enterococcus faecalis* or *Pseudomonas aeruginosa* bacteria.

Embodiment A21. The system of an A Embodiment, wherein said receiving container contains a neutralizer used in disinfecting a medical device with elongated narrow passageways.

Embodiment A22. The system of an A Embodiment, wherein the system is configured to concentrate liquid recovered from said medical device.

Embodiment A23. The system of an A Embodiment, wherein said medical device is an endoscope.

Embodiment A24. The system of an A Embodiment, further comprising connector fittings and tubing, wherein said connector fittings and said tubing and said receiving container are sterile and packaged to retain sterility.

Embodiment B25. A method comprising: (i) providing the system of an A, D or E Embodiment; (ii) operating said system to direct two-phase flow of said gas and said sampling liquid through the narrow elongated passageway; (iii) collecting at least a representative sampling of said sampling liquid after flow through the passageway; and (iv) performing analytical testing for one or more pathogens on said representative sampling.

Embodiment B26. The method of a B Embodiment, wherein said receiving container or a provided sampling container contains neutralizer suitable to neutralize disinfectant substances that may be recovered inside said endoscope.

Embodiment B27. The method of a B Embodiment, further comprising, prior to said analytical testing, concentrating said representative sampling liquid to a smaller volume by removing some but not all water from said liquid.

Embodiment B28. The method of a B Embodiment, wherein said sampling liquid flows through said narrow elongated passageway one time and then is analyzed.

Embodiment B29. The method of a B Embodiment, wherein said sampling liquid flows through said endoscope multiple times and then is analyzed.

Embodiment B30. The method of a B Embodiment, wherein the turnover number for any said elongated narrow passageway is 100 or higher.

Embodiment C31. A method for determining an extent or nature of contamination of an endoscope having two or more narrow elongated channels, said method comprising: (A) supplying a sampling liquid for flowing through the channels of said endoscope, wherein said sampling liquid comprises a sterile aqueous composition that is essentially free of surfactant; (B) supplying clean compressed air for flowing through said channels or said interiors of said endoscope, wherein said sampling liquid flows through said channels as part of a two-phase flow; (C) collecting fluid exiting said channels in one or more receiving containers; and (D) analyzing contaminant contents of said receiving containers.

Embodiment C32. The method of Embodiment C31, further comprising: (E) separating gas from liquid and collecting said liquid as recovered liquid in respective sub-containers that are designated for particular said channels or groups of said channels of said endoscope; and (D2) (as all or part of step D) performing testing to determine the amount or type of microorganisms or organic contaminants in said recovered liquid for particular said channels or groups of channels.

Embodiment C33. The method of a C Embodiment, wherein said sampling liquid is sterile pure water or physiological saline or phosphate buffered saline.

Embodiment C34. The method of a C Embodiment, further comprising, and prior to said analyzing, concentrating said collected fluid to a smaller liquid volume by removing some but not all water from said collected fluid.

Embodiment C35. The method of a C Embodiment, wherein said one or more recovery containers contain an amount and composition of buffer suitable to bring an osmolarity of said recovered liquid closer to a physiological value.

Embodiment D36. A system for determining an extent or nature of contamination of a medical device, said sampling system comprising: (1) a flow supply system configured to supply two-phase flow; (2) a connector for interfacing with a surface of said device; (3) a nozzle for directing a flow of said two-phase flow at said surface; and (4) a receiving container for receiving flow that has been directed at said surface.

Embodiment D37. The system of a D Embodiment, wherein said flow is two-phase flow comprising a liquid and a gas.

Embodiment D38. The system of a D Embodiment, wherein said device is an endoscope comprising an elevator, and said surface is a part of said elevator, and said connector is configured to engage with a distal end of said endoscope.

Embodiment D39. The system of a D Embodiment, wherein said connector is configured to establish or identify an angular position around a rotational axis of said distal end of said endoscope, so as to ensure proper orientation of said flow with respect to said elevator.

Embodiment D40. The system of Embodiment D39 further comprising means for moving said elevator while said flow is being directed at said elevator.

Embodiment D41. The system of a D Embodiment, wherein said surface is an external surface of said device and said connector is conformable to said external surface.

Embodiment E42. A system for determining an extent or nature of contamination of an endoscope, said system comprising: (I) a flow supply system for supplying flow of a sampling fluid to said endoscope; (II) a receiving container, in fluid communication with a distal end of said endoscope, for receiving said flow of said sampling fluid from said endoscope; (III) a brush or swab for brushing an interior of a channel that can accept said brush or said swab, said brush or said swab being connected to a drive mechanism; and (IV) a mechanism for disconnecting or cutting or detaching said brush or said swab or a portion thereof from said drive mechanism while said receiving container is in fluid communication with said distal end of said endoscope, wherein said disconnected brush or the disconnected swab or portion thereof can be deposited into said receiving container while said receiving container is in fluid communication with said endoscope.

Embodiment E43. The system of an E Embodiment, wherein said flow comprises a two-phase flow comprising a liquid and a gas.

Embodiment E44. The system of an E Embodiment, wherein said flow is a single-phase flow of a liquid.

Embodiment E45. The system of an E Embodiment, wherein said brush or said swab is supplied sterile.

What is claimed is:

1. A sampling system for determining an amount or type of contamination in a narrow, elongated passageway in a medical device, said sampling system comprising:
    a fluid supply system that supplies to said passageway a sampling liquid for flowing through said passageway and a gas for flowing through said passageway, the fluid supply system configured to provide two-phase flow;
    a source of pressurization for the gas configured with the fluid supply system to create two-phase flow of said gas and said sampling liquid in said passageway;
    a receiving container that receives liquid from said passageway; and
    a filter configured to pass air from the two-phase flow from the passageway while retaining microorganisms, wherein said sampling liquid is sterile, and
    wherein said sampling liquid is configured to allow recovery of viable pathogens from the sampling liquid received from the passageway as a result of the two-phase flow.

2. The system of claim 1, wherein said sampling liquid has a contact angle that is less than 20 degrees.

3. The system of claim 1, wherein the system is configured to provide solid particles suspended in the two-phase flow effective to enhance recovery of bioburden from the passageway.

4. The system of claim 1, wherein said sampling liquid further comprises a neutralizer for neutralizing a disinfectant used in disinfecting said medical device with elongated narrow passageways.

5. The system of claim 1, configured for two or more said narrow passageways of an endoscope and wherein the fluid supply system is automated for delivering specified flow-rates at specified pressure for specified periods of time to specified ones of said narrow passageways of said endoscope.

6. The system of claim 1, wherein said system is configured to provide in the received sampling liquid a neutralizer of a disinfectant used in disinfecting a medical device with elongated narrow passageways.

7. The system of claim 1, wherein the system is configured to concentrate liquid from the two-phase flow from the passageway.

8. A method comprising:
    providing the system of claim 1;
    operating said system to direct two-phase flow of said gas and said sampling liquid through the narrow elongated passageway;
    collecting at least a representative sampling of said sampling liquid after flow through the passageway; and
    performing analytical testing for one or more pathogens on said representative sampling.

9. The method of claim 8, wherein said receiving container or a provided sampling container contains neutralizer suitable to neutralize disinfectant substances that may be recovered inside said endoscope.

10. The method of claim 8, further comprising, prior to said analytical testing, concentrating said representative sampling liquid to a smaller volume by removing some but not all water from said liquid.

11. The method of claim 8, wherein a turnover number for two-phase flow through any said elongated narrow passageway is 100 or higher.

12. The system of claim 1, wherein said sampling liquid comprises an amount and selection of surfactant effective to enhance dislodgement of *Enterococcus faecalis* and *Pseudomonas aeruginosa* bacteria from the narrow passageways.

* * * * *